(12) United States Patent
Goldberg et al.

(10) Patent No.: US 10,159,707 B2
(45) Date of Patent: *Dec. 25, 2018

(54) TREATMENT OF CANCERS WITH IMMUNOSTIMULATORY HIV TAT DERIVATIVE POLYPEPTIDES

(71) Applicant: PIN Pharma, Inc., New York, NY (US)

(72) Inventors: Joshua Goldberg, New York, NY (US); Colin Bier, New York, NY (US)

(73) Assignee: PIN Pharma, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/587,262

(22) Filed: May 4, 2017

(65) Prior Publication Data

US 2017/0274040 A1    Sep. 28, 2017

Related U.S. Application Data

(63) Continuation of application No. 14/505,977, filed on Oct. 3, 2014, now Pat. No. 9,663,556.

(Continued)

(51) Int. Cl.
*A61K 39/21* (2006.01)
*A61K 38/16* (2006.01)
(Continued)

(52) U.S. Cl.
CPC .......... *A61K 38/162* (2013.01); *A61K 31/664* (2013.01); *A61K 39/0011* (2013.01);
(Continued)

(58) Field of Classification Search
None
See application file for complete search history.

(56) References Cited

U.S. PATENT DOCUMENTS 5,585,103 A    12/1996  Raychaundhuri et al.
5,597,895 A    1/1997   Gaynor et al.
(Continued)

FOREIGN PATENT DOCUMENTS

EP    614980    9/1994
EP    673948    11/1998
(Continued)

OTHER PUBLICATIONS

Chenciner et al., Enhancement of humoral immunity to SIVenv following simultaneous inoculation of mice by three recombinant adenoviruses encoding SIVenv/poliovirus chimeras, Tat and Rev. AIDS Res. and Hum. Retroviruses 13: 801-806 (1997).

(Continued)

*Primary Examiner* — Janet L Andres
*Assistant Examiner* — Stuart W Snyder
(74) *Attorney, Agent, or Firm* — K&L Gates LLP; Louis C. Cullman; David Diamond

(57) ABSTRACT

Disclosed herein are compositions comprising a Human Immunodeficiency Virus (HIV) trans-activator of transcription (Tat) derivative polypeptide with increased immunostimulatory properties relative to the native Tat polypeptide, pharmaceutical compositions comprising the Tat derivative polypeptide, and methods of treating cancer using the Tat derivative polypeptide.

20 Claims, 15 Drawing Sheets

Specification includes a Sequence Listing.

Related U.S. Application Data

(60) Provisional application No. 61/887,166, filed on Oct. 4, 2013.

(51) Int. Cl.
  *A61K 31/664* (2006.01)
  *C07K 14/005* (2006.01)
  *A61K 39/39* (2006.01)
  *A61K 39/00* (2006.01)
  *C12N 15/63* (2006.01)

(52) U.S. Cl.
  CPC .............. *A61K 39/21* (2013.01); *A61K 39/39* (2013.01); *C07K 14/005* (2013.01); *C12N 15/63* (2013.01); *C12N 2740/16011* (2013.01); *C12N 2740/16071* (2013.01)

(56) References Cited

U.S. PATENT DOCUMENTS

| | | |
|---|---|---|
| 5,616,559 A | 4/1997 | Androphy et al. |
| 5,652,122 A | 7/1997 | Frankel et al. |
| 5,656,599 A | 8/1997 | Androphy et al. |
| 5,670,617 A | 9/1997 | Frankel et al. |
| 5,674,980 A | 10/1997 | Frankel et al. |
| 5,686,264 A | 11/1997 | Gaynor et al. |
| 5,747,641 A | 5/1998 | Frankel et al. |
| 5,804,604 A | 9/1998 | Frankel et al. |
| 5,817,308 A | 10/1998 | Scot et al. |
| 5,889,175 A | 3/1999 | Mehtali et al. |
| 5,891,994 A | 4/1999 | Goldstein |
| 5,942,401 A | 8/1999 | Van Baalen et al. |
| 5,981,258 A | 11/1999 | Mehtali et al. |
| 6,010,895 A | 1/2000 | Deacon et al. |
| 6,024,965 A | 2/2000 | Van Baalen et al. |
| 6,132,721 A | 10/2000 | Zagury et al. |
| 6,193,981 B1 | 2/2001 | Goldstein |
| 6,194,388 B1 | 2/2001 | Krieg et al. |
| 6,200,575 B1 | 3/2001 | Zagury et al. |
| 6,207,646 B1 | 3/2001 | Krieg et al. |
| 6,228,369 B1 | 5/2001 | Mehtali et al. |
| 6,239,116 B1 | 5/2001 | Krieg et al. |
| 6,270,769 B1 | 8/2001 | Raychaundhuri et al. |
| 6,284,252 B1 | 9/2001 | Mehtali et al. |
| 6,316,003 B1 | 11/2001 | Frankel et al. |
| 6,319,666 B1 | 11/2001 | Van Baalen et al. |
| 6,339,068 B1 | 1/2002 | Krieg et al. |
| 6,406,705 B1 | 6/2002 | Davis et al. |
| 6,420,141 B1 | 7/2002 | Zagury et al. |
| 6,495,347 B1 | 12/2002 | Siegel et al. |
| 6,497,880 B1 | 12/2002 | Wisniewski |
| 6,524,582 B2 | 2/2003 | Goldstein |
| 6,524,825 B1 | 2/2003 | Mizzen et al. |
| 6,525,179 B1 | 2/2003 | Goldstein |
| 6,593,292 B1 | 7/2003 | Rothbard et al. |
| 6,657,055 B2 | 12/2003 | Siegel et al. |
| 6,667,151 B1 | 12/2003 | Cohen |
| 6,686,333 B1 | 2/2004 | Kashanchi et al. |
| 6,797,491 B2 | 9/2004 | Neefe et al. |
| 7,087,377 B2 | 8/2006 | Loret |
| 7,927,580 B2 | 4/2011 | Cohen |
| 8,530,431 B2 | 9/2013 | Cohen |
| 9,663,556 B2 * | 5/2017 | Goldberg .............. A61K 31/664 |
| 2002/0091073 A1 | 7/2002 | Finkel et al. |
| 2002/0193330 A1 | 12/2002 | Hone et al. |
| 2002/0197269 A1 | 12/2002 | Lingnau et al. |
| 2003/0003160 A1 | 1/2003 | Zagury et al. |
| 2003/0091599 A1 | 5/2003 | Davis et al. |
| 2003/0099663 A1 | 5/2003 | Fleitmann et al. |
| 2003/0099664 A1 | 5/2003 | Wisniewski |
| 2003/0148456 A1 | 8/2003 | Mizzen et al. |
| 2003/0158134 A1 | 8/2003 | Voss |
| 2003/0162719 A1 | 8/2003 | Rothbard et al. |
| 2003/0166832 A1 | 9/2003 | Goldstein |
| 2003/0180326 A1 | 9/2003 | Goldstein |
| 2003/0190326 A1 | 10/2003 | Dalenccon et al. |
| 2003/0194408 A1 | 10/2003 | Goldstein |
| 2003/0215797 A1 | 11/2003 | Cohen |
| 2003/0224010 A1 | 12/2003 | Davis et al. |
| 2003/0232074 A1 | 12/2003 | Lipford et al. |
| 2004/0001852 A1 | 1/2004 | Zagury et al. |
| 2004/0005330 A1 | 1/2004 | Rappaport et al. |
| 2004/0009949 A1 | 1/2004 | Krieg et al. |
| 2004/0028652 A1 | 2/2004 | Wang et al. |
| 2004/0034209 A1 | 2/2004 | Ho et al. |
| 2004/0054137 A1 | 3/2004 | Thomson |
| 2005/0022690 A1 | 10/2005 | Cohen |
| 2005/0244434 A1 | 11/2005 | Cohen |
| 2006/0160183 A1 | 7/2006 | Cohen |
| 2007/0248618 A1 | 10/2007 | Cohen |
| 2008/0044435 A1 | 2/2008 | Cohen |
| 2008/0155703 A1 | 6/2008 | Cohen |
| 2009/0181045 A1 | 7/2009 | Cohen |
| 2009/0202585 A1 | 8/2009 | Cohen |
| 2011/0009336 A1 | 1/2011 | Cohen |
| 2011/0195078 A1 | 8/2011 | Cohen |
| 2012/0093858 A1 | 4/2012 | Cohen |
| 2012/0121636 A1 | 5/2012 | Cohen |

FOREIGN PATENT DOCUMENTS

| | | |
|---|---|---|
| EP | 814834 | 9/2000 |
| EP | 1279404 | 1/2003 |
| FR | 2631355 | 9/1996 |
| WO | 1991/015224 | 10/1991 |
| WO | 1991/018454 | 11/1991 |
| WO | 1994/015634 | 7/1994 |
| WO | 1995/031999 | 11/1995 |
| WO | 1996/027389 | 9/1996 |
| WO | 1998/014589 | 4/1998 |
| WO | 1998/017309 | 4/1998 |
| WO | 1998/043669 | 10/1998 |
| WO | 1998/046083 | 10/1998 |
| WO | 1999/002185 | 1/1999 |
| WO | 1999/016884 | 4/1999 |
| WO | 1999/027958 | 6/1999 |
| WO | 1999/033346 | 7/1999 |
| WO | 1999/033872 | 7/1999 |
| WO | 2000/003732 | 1/2000 |
| WO | 2000/059935 | 10/2000 |
| WO | 2000/078334 | 12/2000 |
| WO | 2000/078969 | 12/2000 |
| WO | 2001/000232 | 1/2001 |
| WO | 2001/024822 | 4/2001 |
| WO | 2001/043771 | 6/2001 |
| WO | 2001/078775 | 10/2001 |
| WO | 2004/108753 | 12/2004 |
| WO | 2005/030799 | 4/2005 |
| WO | 2005/097179 | 10/2005 |
| WO | 2006/033665 | 3/2006 |
| WO | 2010/111292 A1 | 9/2010 |

OTHER PUBLICATIONS

Sho et al., In virto induction of carcioembryonic antigen (CEA)-specific cytotoxic T lymphocytes by dendritic cells transduced with recombinant adenoviruses. Vaccine, vol. 22, pp. 224-236 (2003).

Cohen et al., Pronounced acute immunosuppression in vivo mediated by HIV-1 Tat challenge. Proc. Natl. Acad. Sci. USA, 96(19): 10842-10847 (1999).

Dalgleish et al., Cancer vaccines as a therapeutic modality: the long trek. Cancer Immunol. Immunother., 55: 1025-1032 (2006).

Dalyot-Herman et al., Reversal of CD8+ T cell ignorance and induction of anti-tumor immunity by peptide-pulsed APC. J. Immunol., 165: 6731-7 (2000).

Investing in HIV/AIDS, http://www.worldbank.org/html/extdr/hivaids/inv_hiv.htm (1999).

Database EMBL, Online, Nov. 1, 1998, Park et al., Tat Protein, retrieved from EBI accession No. UNIPROT Database Accession No. 090291, Abstract.

Durrant et al., Cancer vaccines entering Phase III clinical trials. Expert Opinion Emerging Drugs, vol. 8, No. 2, pp. 489-500 (2003).

(56) References Cited

OTHER PUBLICATIONS

Fanales-Belasio et al., Naïve HIV-1 Tat protein targets monocyte-derived dendritic cells and enchances their maturation, function, and antigen-specific T cell responses. J. Immunol., 168: 197-206 (2002).
Fawell et al., Tat-mediated delivery of heterologuos proteins into cells. Proc. Natl. Acad. Sci., vol. 91, pp. 664-668 (1994).
Firfer, Database [Online], New HIV vaccine concept may extend hope to those already infected, http://cnn.com/Health/Aids/9908/29/aids.vaccine (1999).
Fisher et al., Dominant interfering Fas gene mutations impair apoptosis in a human autoimmune lymphoproliferative syndrome. Cell, vol. 81, pp. 935-946 (1995).
Follen et al., Cervical cancer chemoprevention, vaccines, and surrogate endpoint biomarkers. American Cancer Society, Cancer Supplement, vol. 98, No. 9, pp. 2044-2051 (2003).
Frankel et al., Activity of synthetic peptides from the TAT protein of human immunodeficiency virus type 1. Proc. Natl. Acad. Sci., vol. 86, pp. 7397-7401 (1989).
Frankel et al., Cellular uptake of the Tat protein from human immunodeficiency virus. Cell, 55: 1189-93 (1988).
Friedman et al., Expression of a truncated viral trans-activator selectively impedes lytic infection by its cognate virus. Nature, vol. 335, pp. 452-454 (1988).
Fultz et al. "SIVsmm Infection of Macaque and Mangabey Monkeys: Correlation between in vivo and in vitro properties of different isolates." Develop. biol. Standard., vol. 72, pp. 253-258, 1990.
Gallo, RC., Tat as one key HIV-induced immune pathogenesis and Tat toxoid as an important component of a vaccine. Proc. Natl. Acad. Sci. USA, vol. 96, pp. 8324-8326 (1999).
Giannouli et al., Fusion of a tumour-associated antigen to HIV-1 Tat improves protein-based immunotherapy of cancer. Anticancer Research, vol. 23, No. 4, pp. 3523-3532 (2003).
Goldstein, G., HIV-1 Tat protein as a potential AIDS vaccine. Nature Medicine, vol. 1, No. 9, pp. 960-964 (1996).
Gringeri et al., Safety and immunogenicity of HIV-1 Tat toxoid in immunocompromised HIV-1-infected patients. Journal of Human Virology, vol. 1, No. 4, pp. 293-298 (1998).
Gringeri et al., Tat toxoid as a component of a preventive vaccine in seronegative subjects. Journal of Accquired Immune Deficiency Syndromes and Human Retrovirology, vol. 20, No. 4, pp. 371-375 (1999).
Harrop et al., Recombinant viral vectors: cancer vaccines. Adv. Drug Delivery Rev., 58: 931-947 (2006).
Heneine et al., Stepwise iodination. A general procedure for detoxification of proteins suitable for vaccine development and antiserum production. Biologicals 26, 25-32 (1998).
Hernando et al., Dendritic cell-based vaccines in breast and gynaecologic cancer. Anticancer Res., 23: 4293-4304 (2003).
Hsieh et al., Tumor-induced immunosupression: a barrier to immunotherapy of large tumors by cytokine-secreting tumor vaccine. Human Gene Therapy, vol. 11, pp. 681-692 (2000).
Ishigami et al., Tumor-associated macrophage (TAM) infiltration in gastric cancer. Anticancer Res., vol. 23, pp. 4079-4084 (2003).
Jager et al., Identification of tumor antigens as potential target antigens for immunotherapy by serological expression cloning, http://www.springerlink.com/media/gmgkwgmxxeebf3wn9h2m/Contributins/X/3/9/F/X39, pp. 1-9 (2004).
Jasinska et al., Inhibition of tumor cell growth by antibodies induced after vaccination with peptides derived from the extracellular domin of HER-2/NEU. Int. J. Cacner, vol. 107, pp. 976-983 (2003).
Jiang et al., Fas mediates apoptosis and oxidant-induced cell death in cultured hRPE cells. Invest Ophthalmol. Vis. Sci., vol. 42, No. 3, pp. 645-655 (2000).
Kanazawa et al., Effect of DC therapy combined with chemotherapy in advanced cancer cases. Jpn J. Cancer Chemother, vol. 30, No. 11, pp. 1655-1660 (2003).
Kjaergaard et al., Electrofusion of syngeneic dendritic cells and tumor generates potent therapeutic vaccine. Cellular Immunology, vol. 225, pp. 65-74 (2003).

Kuppuswamy et al., Multiple functional domains of Tat, the trans-activator of HIV-1, defined by mutational analysis. Nucleic Acids Research, vol. 17, No. 9, pp. 3551-3561 (1989).
Lane et al. "The expression and prognostic value of the guanine nucleotide exchange factors (GEFs) Trio, Vav1 and TIAM-1 in human breast cancer" BioMed Central, Oct. 2008.
Leonard et al., Periodate oxidation of sulfides to sulfoxides. Scope of the Reaction, the Journal of Organic Chemistry, vol. 27, No. 1, pp. 282-284 (1962).
Arbuckle Mi et al. "The SH3 domain of postsynaptic density 95 mediates inflammatory pain through phosphatidyinositol-3-kinase recruitment." EMBO Reports 11:473-78. 2010.
Database Query SA977698:3, Jun. 23, 2010 Accession No. P27975.
Demaria et al. "Immune-Mediated Inhibition of Metastases after Treatment with Local Radiation and CTLA-4 Blockade in a Mouse Model of Breast Cancer." Clinical Cancer Research, vol. 11, 728-734, 2005.
Dupre et al. "Microenvironment of the murine mammary carcinoma 4T1: Endogenous IFN-y affects tumor phenotype, growth and metastasis." Experimental and Molecular Pathology 85 (2008) 174-188.
Henikoff et al. "Amino acid substitution matrices from protein blocks." Proc. Natl. Acad. Sci. USA, vol. 89, pp. 10915-10919, 1992.
Hirano T "Revival of the autoantibody model of rheumatoid arthritis." Nat Immunol 3:342-44.2002.
Kamata T eta. "Src homology2 domain-containing tyrosine phosphatase SHP-1 controls the development of allergic airway inflammation," J Clin Invest 111:109-19, 2003.
Martin R et al. "Immunotherapy of multiple sclerosis: Where are we? Where should we go?" Nat Immunol 2:785-88. 2001.
Mayer BJ "SH3 domains: complexity in moderation," J Cell Sci 114:1253-63,2001.
NCBI GenBank accession No. ACN6334.1, Mar. 15, 2009.
PCT/US2013/073658 International Search Report and Written Opinion.
Pulaski et al. "Cooperativity of *Staphylococcal aureus* Enterotoxin B Superantigen, Major Histocompatibility Complex Class II, and CD80 for Immunotherapy of Advanced Spontaneous Metastases in a Clinically Relevant Postoperative Mouse Breast Cancer Model." Cancer Research 60, 2710-2715, 2000.
Ranga U et al. "Tat protein of human immunodeficiency virus type I subtype C strains is a defective chemokine," J Virol 78:2586-90, 2004.
Reebye Vet al. "A perspective on non-catalytic Src homology (SH) adaptor signalling proteins," Cellular Signalling 24:388-92, 2012.
Reske-Kunz et al. "Disproportion in T-Cell Subpopulations in Immunodeficient Mutant hr/hr Mice." J. Exp. Med. vol. 149, 1979, 228-233.
Lepple-Wienhues et al., Stimulation of CD95 (FAS) blocks T lymphocyte calcium channels through sphingomyelinase and sphingolipids. PNAS, vol. 96, No. 24, pp. 13795-13800 (1999).
Li et al., Induction of apoptosis in uninfected lymphocytes by HIV-1 Tat protein. Science, vol. 268, pp. 429-431 (1995).
Li et al., Tat protein induces self-perpetuating permissivity for productive HIV-1 infection. PNAS, vol. 94, pp. 8116-8120 (1997).
Lin et al., The macrophage growth factor CSF-1 in mammary gland development and tumor progression. Journal of Mammary Gland Biology and Neoplasia, vol. 7, No. 2, pp. 147-162 (2002).
Liu et al., Concurrent delivery of tumor antigens an activation signals to dendritic cells by irradiated CD40 ligand-transfected tumor cells resulted in efficient activation of specific CD8+ T cells. Cancer Gene Therapy, vol. 11, pp. 135-147 (2004).
Martin et al., Human embryonic stem cells express an immunogenic nonhuman sialic acid. Nat. Med. 11:228-232 (2005).
Medina et al., Regulatory role of CD95 ligation on human B cells induced in vivo capable of spontaneous and high-rate Ig secretion. Eur. J. Immunol., vol. 27, pp. 700-706 (1997).
Moy et al., Tat-mediated protein delivery can facilitate MHC class I presentation of antigens. Mol. Biotechnol. 6: 105-113 (1996).
Nagata S., Apoptosis by death factor. Cell, vol. 88, pp. 355-365 (1997).

(56) References Cited

OTHER PUBLICATIONS

Niesner et al., Quantitation of the tumor-targeting properties of antibody fragments conjugated to cell-permeating HIV-1 Tat peptdies. Biocont Chem. 13: 729-736 (2002).

Nouri-Shirazi et al., Dendritic cell based tumor vaccines. Immunology Letters, vol. 74, pp. 5-10 (2000).

Novak et al., Engagement of FceRI on human monocytes induces the production of IL-10 and prevent their differentiation in dendritic cells. J. Immunol., 167: 797-804 (2001).

Darbinian et al., Growth inhibition of glioblastoma cells by human pur alpha. Journal of Cellular Physiology, vol. 189, No. 3, pp. 334-340 (2001).

Paillard et al., Immunosupression mediated by tumor cells: a challenge for immunotherapeutic approaches. Human Gene Therapy, vol. 11, pp. 657-658 (2000).

Park et al., Mutations in both gp120 and gp41 are responsible for the broad neutralization resistance of variant human immunodeficiency virus type 1 Mn to antibodies directed at V3 and non-V3 epitopes. Journal of Virology, vol. 72, No. 9, pp. 7099-7107 (1998).

Peter et al., Resistance of cultured peripheral T cells towards activation-induced cell death involves a lack of recruitment of FLICE (MACH/caspase 8) to the CD95 death-inducing signaling complex. Eur. J. Immunol., vol. 27, pp. 1207-1212 (1997).

Phan et al., Cancer regression and autoimmunity induced by cytotoxic T lymphocyte-associated antigen 4 blockade in patients with metastatic melanoma. PNAS, 100: 8372-7 (2003).

Prive et al. "Specific peptides for the therapeutic targeting of oncogenes." Current Opinion in Genetics & Development, 2006, 16:71-77.

Quinones-Mateu et al., LATR and tat variability of HIV-1 isolates from patients with divergent rates of disease progression. Virus Research, 57, 11-20 (1998).

Rana et al., Biochemical and functional interactions between HIV-1 Tat protein and TAR RNA. Archives of Biochemistry and Biophysics, vol. 365, No. 2, pp. 175-185 (1999).

Re et al., Effect of antibody to HIV-1 Tat protein on viral replication in vitro and progression of HIV-1 disease in vivo. Journal of Acquired immune deficiency syndromes and human retrovirology, 10, 408-416 (1995).

Reinhold et al., HIV-1 Tat: immunosuppression via TFG-beta1 induction. Immunology Today, 20(8): 384 (1999).

Riffkin et al., A single amino-acid change between the antigenically different extracellular erine proteases V2 and B2 from Dichelobacter nodosus. Gene, vol. 167, pp. 279-283 (1995).

Schluesener HJ, Protection against experimental nervous system autoimmune diseases by a human immunodeficiency virus-1 Tat peptide-based polyvalent vaccine. J. Neurosci. Res. 46:258-262 (1996).

Schwarze et al., In vivo protein transduction: delivery of a biologically active protein into the mouse. Science 285: 1569-1572 (1999).

Small et al., Immunotherapy of hormone-refractory prostate cancer with antigen-loaded dendritic cells. Journal of Clinical Oncology, vol. 18, No. 23, pp. 3894-3903 (2000).

Waldmann, T.A., Immunotherapy: past, present and future. Nat. Med. 9(3): 269-277 (2003).

Wang et al., Induction of CD4+ T-cell dependent antitumor immunity by TAT-mediated tumor antigen delivery into dendritic cells. J. Clin. Invest., vol. 109, No. 11, pp. 1463-1470 (2002).

Zhang et al., Induction of specific T cell tolerance by Fas ligand-expressing antigen-presenting cells. J. Immunol., 162: 1423-1430 (1999).

Tasca et al., Escpate of monocyte-derived dendritic cells of HIV-1 infected individuals from natural killer cell-mediated lysis. AIDS, vol. 17, pp. 2291-2298 (2003).

Tosi et al., Highly stable oligomerization forms of HIV-1 Tat detected by monoclonal antibodies and requirement of monomeric forms for the transactivating function on the HIV-1 LTR. Eu.r. J. Immunol., 30: 1120-1126 (2000).

Turtle et al., Dendritic cells cells in tumor immunology and immunotherapy. Current Drug Targets, vol. 5, No. 1, pp. 17-39 (2004).

Viscidi et al., Inhibition of antigen-induced lymphocyte proliferation by Tat protein from HIV-1. Science, 246: 1606-1608 (1989).

Visscher et al., Clinicopathologic analysis of macrophage infiltrates in breast carcinoma. Path. Res. Pract. (Suppl.), vol. 191, pp. 1133-1139 (1995).

Vocero-Akbani et al., Killing HIV-infected cells by transduction with an HIV protease-activated caspase-3 protein. Nature Medicine, vol. 5, No. 1, pp. 29-33 (1999).

Von Bernstorff et al., Systemic and local immunosupression in pancreatic cancer patients. Clinical Cancer Research, vol. 7, Supplement, pp. 925s-932s (2001).

Wachsman et al., HTLV x Gene mutants exhibit novel transcriptional regulatory phenotypes. Science, vol. 235, pp. 574-677 (1987).

Wadia et al., Transmembrane delivery of protein and peptide drugs by TAT-mediated transduction in the treatment of cancer. Advanced Drug Delivery Reviews 57, 579-596 (2005).

Richardson et al. "Cellular mechanisms of neurogenic inflammation," J Pharmacol Exp Ther 302:839-45, 2002.

Seipel et al. "Tara, a novel F-actin binding protein, associates with the Trio guanine nucleotide exchange factor and regulates actin cytoskeletal organization." Research Article, Journal of Cell Science 114, 389-399, 2000.

Ohara-Imaizumi M, et al. Site of docking and fusion of insulin secretory granules in live MIN6 beta cells analyzed by TAT-conjugated anti-syntaxin 1 antibody and total internal reflection fluorescence microscopy. J Biol Chem. 2004;279(9):8403-8.

Lee TH, Sheppard HW, Reis M, Dondero D, Osmond D, Busch MP. Circulating HIV-1-infected cell burden from seroconversion to AIDS: importance of postseroconversion viral load on disease course. J Acquir Immune Defic Syndr. 1994;7(4):381-8.

Benedetto A, Garbuglia AR, Di caro A, Lo presti E, Alfani E, Delfini C. Virus-free survival and down-regulation of CD4 in C8166 cells infected with human immunodeficiency virus type 1 at low density. J Gen Virol. 1993;74 ( Pt 12):2595-601.

Wang B, Ge YC, Palasanthiran P, et al. Gene defects clustered at the C-terminus of the vpr gene of HIV-1 in long-term nonprogressing mother and child pair: in vivo evolution of vpr quasispecies in blood and plasma. Virology. 1996;223 (1):224-32.

Hofmeyer KA, Jeon H, Zang X. The PD-1/PD-L1 (B7-H1) pathway in chronic infection-induced cytotoxic T lymphocyte exhaustion. J Biomed Biotechnol. 2011;2011:451694.

Yao Y, Tao R, Wang X, Wang Y, Mao Y, Zhou LF. B7-H1 is correlated with malignancy-grade gliomas but is not expressed exclusively on tumor stem-like cells. Neuro-oncology. 2009;11(6):757-66.

Wang X, Zhang Z, Zhang S, et al. B7-H1 up-regulation impairs myeloid DC and correlates with disease progression in chronic HIV-1 infection. Eur J Immunol. 2008;38(11):3226-36.

Afreen S, Dermime S. The immunoinhibitory B7-H1 molecule as a potential target in cancer: killing many birds with one stone. Hematol Oncol Stem Cell Ther. 2014;7(1):1-17.

Keilholz U. CTLA-4: negative regulator of the immune response and a target for cancer therapy. J Immunother. 2008;31(5):431-9.

Velcheti V, Schalper KA, Carvajal DE, et al. Programmed death ligand-1 expression in non-small cell lung cancer. Lab Invest. 2014;94(1):107-16.

Agwale et al., A Tat subunit vaccine confers protective immunity against the immune-modulating activity of the human immunodeficiency virus type-1 Tat protein in mice. PNAS, 99: 10037-10041 (2002).

Arlen et al., Strategies for the development of PSA-based vaccines for the treatment of advanced prostate cancer. Expert Rev. Vaccines, vol. 2, No. 4 , pp. 483-493 (2003).

Augustine, R.L., Oxidation techniques and applications in organic synthesis, vol. 1, pp. 244-248 (1969).

Baghian et al., Protective immunity against lethal HSV-1 challenge in mice by nucleic acid-based immunization with herpes simplex virus type-1 genes specifying glycoproteins gB and gD. J. Med. Microbiol., vol. 51, pp. 350-357 (2002).

(56) References Cited

OTHER PUBLICATIONS

Banchereau et al., Dendritic cells as vectors for therapy. Cell, 106: 271-274 (2001).
Bayer et al., Structural studies of HIV-1 Tat protein. J. Mol. Biol., vol. 247, pp. 529-535 (1995).
Beissert e al., IL-10 inhibits tumor antigen presentation by epidermal antigen-presenting cells. The Journal of Immunology, vol. 154, pp. 1280-1286 (1995).
Bettelli et al., Th-17 cells in the inner circle of immunity and autoimmunity. Nat. immunol., 8(4): 345-350 (2007).
Boykins et al., Immunization with a novel HIV-1-Tat multiple-peptide conjugate induces effective immune response in mice. Peptides, vol. 21, No. 12, pp. 1839-1847 (2000).
Badley et al., Macrophage dependent apoptosis of CD4+ T lymphocytes from HIV-infected individuals is mediated by FasL and tumor necrosis factor. J. Exp. Med., vol. 185, No. 1, pp. 55-64 (1997).
Badley et al., Upregulation of Fas ligand expression by human immunodeficiency virus in human macrophages mediates apoptosis of uninfected T lymphocytes. J. Virol., 70(1): 199-206 (1996).
Le Buanec et al., A prophylactic and therapeutics AIDS vaccine containing as a component the innocuous Tat Toxoid. Biomedicine and Pharmacotheraphy, vol. 52, No. 10, pp. 431-435 (1998).
Nielsen SD, et al. Expression of the activation antigen CD69 predicts functionality of in vitro expanded peripheral blood mononuclear cells (PBMC) from healthy donors and HIV-infected patients. Clin Exp Immunol. 1998;114(1):66-72.
Caputo et al., Immunization with low doses of HIV-1 Tat DNA delivered by novel cationic block copolymers induces CTL responses against Tat Vaccine, vol. 21, pp. 1103-1111 (2003).
Caselli et al., DNA immunization with HIV-1 Tat DNA mutated in the trans activation domain induces humoral and cellular immune responses against wild-type Tat J. Immunol., 162: 5631-5638 (1999).
Cataro et al., Control of SHIV-89.6P-Infection of cynomolgus monkeys by HIV-1 tat protein vaccine. Nature Medicine, 5(16), 643-650 (1999).
Chang et al., HIV-1 Tat protein exits from cells via a leaderless secretory pathway and binds to extracellular matrix-associated heparan sulfate proteoglycans through its basic region. AIDS, vol. 11, No. 12, p. 1421-1431 (1997).
Cheadle et al., Identification of a Src SH3 domain binding motif by screening a random phage display library. The Journal of Biological Chemistry, vol. 269, No. 39, pp. 24034-24039 (1994).
Palacios R, et al. Long-term culture of lymphohematopoietic stem cells. Proc Natl Acad Sci USA. 1996;93(11):5247-52.
Zagury D, et al. Long-term cultures of HLTV-III—infected T cells: a model of cytopathology of T-cell depletion in AIDS. Science. 1986;231(4740):850-3.
Oba J, et al., To the Editor: Expression of programmed death receptor ligand 1 in melanoma may indicate tumor progression and poor patient survival. J Am Acad Dermatol. 2014; 70(5):954-955.
International Search Report and Written Opinion for PCT/US2014/059035.
Johnson et al., "tat protein [Simian immunodeficiency virus]", GenBank database [online] Mar. 5, 1996 (May 3, 1996), Accession No. AAA91909.1.
Alignment of cited sequence and NaniP-2.

\* cited by examiner

SEQUENCE LISTING

<160> NUMBER OF SEQ ID NOS: 150

<210> SEQ ID NO 1
<211> LENGTH: 101
<212> TYPE: PRT
<213> ORGANISM: Human immunodeficiency virus type 1

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala Pro Glu Asp Ser Gln Thr
    50                  55                  60

His Gln Val Ser Pro Pro Lys Gln Pro Ala Pro Gln Phe Arg Gly Asp
65                  70                  75                  80

```
Pro Thr Gly Pro Lys Glu Ser Lys Lys Val Glu Arg Glu Thr Glu
            85                  90                  95

Thr His Pro Val Asp
        100

<210> SEQ ID NO 2
<211> LENGTH: 102
<212> TYPE: PRT
<213> ORGANISM: Artificial Sequence
<220> FEATURE:
<223> OTHER INFORMATION: Tat derivative polypeptide

<400> SEQUENCE: 2

Met Glu Pro Val Asp Ala Asn Leu Glu Ala Trp Lys His Ala Gly Ser
1               5                   10                  15

Gln Pro Arg Lys Thr Ala Cys Thr Cys Tyr Cys Lys Cys Cys
            20                  25                  30

Phe His Cys Gln Val Cys Phe Thr Arg Lys Gly Leu Gly Ile Ser Tyr
                35                  40                  45

Gly Arg Lys Lys Arg Arg Gln Arg Arg Ala Pro Gln Asp Ser Gln
    50                  55                  60

Thr His Gln Ala Ser Leu Ser Lys Gln Pro Ala Ser Gln Ser Arg Gly
65                  70                  75                  80

Asp Pro Thr Gly Pro Thr Glu Ser Lys Lys Val Glu Arg Glu Thr
                85                  90                  95

Glu Thr Asp Pro Phe Asp
                100

<210> SEQ ID NO 3
<211> LENGTH: 119
<212> TYPE: PRT
<213> ORGANISM: Artificial Sequence
<220> FEATURE:
<223> OTHER INFORMATION: Tat derivative polypeptide

<400> SEQUENCE: 3

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Leu Arg Lys Gly Leu
                35                  40                  45

Gly Ile Thr Tyr His Ala Phe Arg Thr Arg Lys Lys Ile Ala Ser
    50                  55                  60

Ala Asp Arg Ile Pro Val Pro Gln Gln Ser Ile Ser Ile Arg Gly Arg
65                  70                  75                  80

Asp Ser Gln Thr Thr Gln Glu Ser Gln Lys Lys Val Glu Glu Gln Ala
                85                  90                  95

Lys Ala Asn Leu Arg Ile Ser Arg Lys Asn Leu Gly Asp Glu Thr Arg
            100                 105                 110

Gly Pro Val Gly Ala Gly Asn
        115

<210> SEQ ID NO 4
<211> LENGTH: 130
<212> TYPE: PRT
<213> ORGANISM: Artificial Sequence
<220> FEATURE:
<223> OTHER INFORMATION: Tat derivative polypeptide
```

```
<400> SEQUENCE: 4

Met Glu Thr Pro Leu Lys Glu Gln Glu Asn Ser Leu Glu Ser Cys Arg
1               5                   10                  15

Glu His Ser Ser Ser Ile Ser Glu Val Asp Val Pro Thr Pro Val Ser
                20                  25                  30

Cys Leu Arg Lys Gly Arg Cys Trp Asn Arg Cys Ile Gly Asn Thr
            35                  40                  45

Arg Gln Ile Gly Ser Cys Gly Val Pro Phe Leu Lys Cys Cys Lys Arg
        50                  55                  60

Lys Pro Phe Thr Arg Lys Gly Leu Gly Ile Ser Tyr Gly Arg Lys Lys
65                  70                  75                  80

Arg Arg Gln Arg Arg Ala Pro Gln Asp Ser Gln Thr His Gln Ala
                85                  90                  95

Ser Leu Ser Lys Gln Pro Ala Ser Gln Ser Arg Gly Asp Pro Thr Gly
                100                 105                 110

Pro Thr Glu Ser Lys Lys Lys Val Glu Arg Glu Thr Glu Thr Asp Pro
            115                 120                 125

Phe Asp
    130

<210> SEQ ID NO 5
<211> LENGTH: 136
<212> TYPE: PRT
<213> ORGANISM: Artificial Sequence
<220> FEATURE:
<223> OTHER INFORMATION: Tat derivative polypeptide

<400> SEQUENCE: 5

Met Glu Thr Pro Leu Lys Glu Gln Glu Ser Ser Leu Glu Ser Ser Arg
1               5                   10                  15

Glu His Ser Ser Ser Ile Ser Glu Val Asp Ala Asp Thr Pro Glu Ser
                20                  25                  30

Ala Ser Leu Glu Glu Glu Ile Leu Ser Gln Leu Tyr Arg Pro Leu Glu
            35                  40                  45

Thr Cys Asn Asn Thr Cys Tyr Cys Lys Glu Cys Cys Tyr His Cys Gln
        50                  55                  60

Leu Cys Phe Leu Asn Lys Gly Leu Gly Ile Trp Tyr Asp Arg Lys Gly
65                  70                  75                  80

Arg Arg Arg Arg Ser Pro Lys Lys Ile Lys Ala His Ser Ser Ser Ala
                85                  90                  95

Ser Asp Lys Ser Ile Ser Thr Arg Thr Arg Asn Ser Gln Pro Glu Glu
            100                 105                 110

Lys Gln Lys Lys Thr Leu Glu Thr Thr Leu Gly Thr Asp Cys Gly Pro
            115                 120                 125

Gly Arg Ser His Ile Tyr Ile Ser
    130                 135

<210> SEQ ID NO 6
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 6

Met Asp Ala Gly Lys Ala Val Ser Asp Lys Lys Glu Gly Asp Val Thr
1               5                   10                  15
```

```
Pro Tyr Asp Pro Phe Arg Asp Arg Thr Thr Pro Leu Glu Thr Cys Asn
            20                  25                  30

Asn Thr Cys Tyr Cys Lys Glu Cys Cys Tyr His Cys Gln Leu Cys Phe
        35                  40                  45

Leu Asn Lys Gly Leu Gly Ile Trp Tyr Asp Arg Lys Gly Arg Arg Arg
    50                  55                  60

Arg Ser Pro Lys Lys Ile Lys Ala His Ser Ser Ala Ser Asp Lys
65                  70                  75                  80

Ser Ile Ser Thr Arg Thr Arg Asn Ser Gln Pro Glu Glu Lys Gln Lys
                85                  90                  95

Lys Thr Leu Glu Thr Thr Leu Gly Thr Asp Cys Gly Pro Gly Arg Ser
            100                 105                 110

His Ile Tyr Ile Ser Ala
        115

<210> SEQ ID NO 7
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 7

Met Asp Lys Gly Glu Glu Glu Arg Thr Val Leu His Gln Asp Leu Ile
1               5                   10                  15

Arg Gln Tyr Lys Lys Pro Arg Thr Ala Cys Asn Asn Cys Tyr Cys Lys
            20                  25                  30

Lys Cys Cys Phe His Cys Tyr Ala Cys Phe Leu Arg Lys Gly Leu Gly
        35                  40                  45

Ile Thr Tyr His Ala Phe Arg Thr Arg Arg Lys Lys Ile Ala Ser Ala
    50                  55                  60

Asp Arg Ile Pro Val Pro Gln Gln Ser Ile Ser Ile Arg Gly Arg Asp
65                  70                  75                  80

Ser Gln Thr Thr Gln Glu Ser Gln Lys Lys Val Glu Glu Gln Ala Lys
                85                  90                  95

Ala Asn Leu Arg Ile Ser Arg Lys Asn Leu Gly Asp Glu Thr Arg Gly
            100                 105                 110

Pro Val Gly Ala Gly Asn
        115

<210> SEQ ID NO 8
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 8

Met Asp Lys Gly Glu Glu Glu Arg Thr Val Leu His Gln Asp Leu Ile
1               5                   10                  15

Arg Gln Tyr Lys Lys Pro Arg Thr Ala Cys Asn Asn Cys Tyr Cys Lys
            20                  25                  30

Lys Cys Cys Phe His Cys Tyr Ala Cys Phe Leu Arg Lys Gly Leu Gly
        35                  40                  45

Ile Thr Tyr His Ala Phe Arg Thr Arg Arg Lys Lys Ile Ala Ser Ala
    50                  55                  60

Asp Arg Ile Pro Val Pro Gln Gln Ser Ile Ser Ile Arg Gly Arg Asp
```

```
                65                  70                  75                  80
Ser Gln Thr Thr Gln Glu Ser Gln Lys Lys Val Glu Glu Gln Ala Lys
                85                  90                  95

Ala Asn Leu Arg Ile Ser Arg Lys Asn Leu Gly Asp Glu Thr Arg Gly
               100                 105                 110

Pro Val Gly Ala Gly Asn
       115

<210> SEQ ID NO 9
<211> LENGTH: 125
<212> TYPE: PRT
<213> ORGANISM: Artificial Sequence
<220> FEATURE:
<223> OTHER INFORMATION: Tat derivative polypeptide

<400> SEQUENCE: 9

Met Asp Pro Lys Gly Glu Glu Asp Gln Asp Val Ser His Gln Asp Leu
1               5                  10                  15

Ile Lys Gln Tyr Arg Lys Pro Arg Thr Ala Cys Asn Asn Cys Tyr Cys
                20                  25                  30

Lys Lys Cys Cys Phe His Cys Tyr Ala Cys Phe His Cys Tyr Ala Cys
            35                  40                  45

Phe Leu Gln Lys Gly Leu Gly Val Thr Tyr His Ala Pro Arg Thr Arg
50                  55                  60

Arg Lys Lys Ser Val Gln Pro Asn Arg Leu Ser Gln Gln Asp Gln Ser
65                  70                  75                  80

Ile Ser Thr Arg Gly Arg Asp Gly Gln Ala Thr Gln Glu Ser Gln Lys
                85                  90                  95

Lys Val Glu Arg Glu Thr Thr Thr Ala Gln Ile Leu Gly Arg Lys Asp
               100                 105                 110

Leu Glu Arg Asp Lys Arg Glu Ala Val Gly Ala Asn Ala
           115                 120                 125

<210> SEQ ID NO 10
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 10

Met Asp Gln Glu Gln Glu Ala Arg Pro Gln Val Trp Glu Glu Leu Gln
1               5                  10                  15

Glu Glu Leu His Arg Pro Arg Thr Ala Cys Asn Asn Cys Tyr Cys Lys
                20                  25                  30

Lys Cys Cys Phe His Cys Tyr Ala Cys Phe Leu Arg Lys Gly Leu Gly
            35                  40                  45

Ile Thr Tyr His Ala Phe Arg Thr Arg Arg Lys Lys Ile Ala Ser Ala
       50                  55                  60

Asp Arg Ile Pro Val Pro Gln Gln Ser Ile Ser Ile Arg Gly Arg Asp
65                  70                  75                  80

Ser Gln Thr Thr Gln Glu Ser Gln Lys Lys Val Glu Glu Gln Ala Lys
                85                  90                  95

Ala Asn Leu Arg Ile Ser Arg Lys Asn Leu Gly Asp Glu Thr Arg Gly
               100                 105                 110

Pro Val Gly Ala Gly Asn
       115
```

<210> SEQ ID NO 11
<211> LENGTH: 73
<212> TYPE: PRT
<213> ORGANISM: Artificial Sequence
<220> FEATURE:
<223> OTHER INFORMATION: Tat derivative polypeptide

<400> SEQUENCE: 11

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe His Lys Lys Ala Leu
        35                  40                  45

Gly Ile Arg Tyr Tyr Val Pro Arg Pro Arg Arg Ala Ser Lys Lys Ile
    50                  55                  60

Ser His Asn Gln Val Ser Leu His Asn
65                  70

<210> SEQ ID NO 12
<211> LENGTH: 115
<212> TYPE: PRT
<213> ORGANISM: Artificial Sequence
<220> FEATURE:
<223> OTHER INFORMATION: Tat derivative polypeptide

<400> SEQUENCE: 12

Met Glu Ser Glu Gly Asp Gly Met Ala Glu Ser Leu Leu Gln Asp Leu
1               5                   10                  15

His Arg Pro Arg Thr Ala Cys Asn Asn Cys Tyr Cys Lys Lys Cys Cys
            20                  25                  30

Phe His Cys Tyr Ala Cys Phe Leu Arg Lys Gly Leu Gly Ile Thr Tyr
        35                  40                  45

His Ala Phe Arg Thr Arg Arg Lys Lys Ile Ala Ser Ala Asp Arg Ile
    50                  55                  60

Pro Val Pro Gln Gln Ser Ile Ser Ile Arg Gly Arg Asp Ser Gln Thr
65                  70                  75                  80

Thr Gln Glu Ser Gln Lys Lys Val Glu Glu Gln Ala Lys Ala Asn Leu
                85                  90                  95

Arg Ile Ser Arg Lys Asn Leu Gly Asp Glu Thr Arg Gly Pro Val Gly
            100                 105                 110

Ala Gly Asn
        115

<210> SEQ ID NO 13
<211> LENGTH: 110
<212> TYPE: PRT
<213> ORGANISM: Artificial Sequence
<220> FEATURE:
<223> OTHER INFORMATION: Tat derivative polypeptide

<400> SEQUENCE: 13

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe His Cys Tyr Ala Cys
        35                  40                  45

Phe Leu Gln Lys Gly Leu Gly Ile Thr Tyr His Val Ser Arg Ile Arg

```
                    50                  55                  60
Arg Pro Lys Lys Asn His Ser Asn His Gln Asn Leu Val Ser Gln Gln
 65                  70                  75                  80

Ser Ile Ser Ala Trp Gly Gly Asn Ser Gln Thr Thr Gln Glu Glu Lys
                     85                  90                  95

Thr Lys Ile Pro Ala Ala Ala Glu Thr Ser Arg Arg Pro Gln
                100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 14

Met Asp Lys Gly Glu Ala Glu Gln Ile Val Ser His Gln Asp Leu Ser
 1               5                  10                  15

Glu Asp Tyr Gln Lys Pro Arg Thr Ala Cys Asn Asn Cys Tyr Cys Lys
                 20                  25                  30

Lys Cys Cys Phe His Cys Tyr Ala Cys Phe Leu Arg Lys Gly Leu Gly
             35                  40                  45

Ile Thr Tyr His Ala Phe Arg Thr Arg Lys Lys Ile Ala Ser Ala
         50                  55                  60

Asp Arg Ile Pro Val Pro Gln Gln Ser Ile Ser Ile Arg Gly Arg Asp
 65                  70                  75                  80

Ser Gln Thr Thr Gln Glu Ser Gln Lys Lys Val Glu Glu Gln Ala Lys
                 85                  90                  95

Ala Asn Leu Arg Ile Ser Arg Lys Asn Leu Gly Asp Glu Thr Arg Gly
                100                 105                 110

Pro Val Gly Ala Gly Asn
            115

<210> SEQ ID NO 15
<211> LENGTH: 100
<212> TYPE: PRT
<213> ORGANISM: Artificial Sequence
<220> FEATURE:
<223> OTHER INFORMATION: Tat derivative polypeptide

<400> SEQUENCE: 15

Met Asp Pro Lys Gly Glu Glu Asp Gln Asp Val Ser His Gln Asp Leu
 1               5                  10                  15

Ile Lys Gln Tyr Arg Lys Pro Arg Thr Ala Cys Asn Asn Cys Tyr Cys
                 20                  25                  30

Lys Lys Cys Cys Phe His Cys Tyr Ala Cys Phe Leu Gln Lys Gly Leu
             35                  40                  45

Gly Val Thr Tyr His Ala Pro Arg Thr Arg Lys Lys Ile Arg Ser
         50                  55                  60

Leu Asn Leu Ala Pro Leu Gln His Gln Ser Ile Ser Thr Lys Trp Gly
 65                  70                  75                  80

Arg Asp Gly Gln Thr Thr Pro Thr Ser Gln Glu Lys Val Glu Thr Thr
                 85                  90                  95

Ala Gly Ser Asn
            100

<210> SEQ ID NO 16
<211> LENGTH: 116
```

```
<212> TYPE: PRT
<213> ORGANISM: Artificial Sequence
<220> FEATURE:
<223> OTHER INFORMATION: Tat derivative polypeptide

<400> SEQUENCE: 16

Met Asp Lys Glu Glu Pro His Pro Leu Leu Gln Asp Leu His Arg
1               5                   10                  15

Pro Leu Gln Pro Arg Thr Ala Cys Asn Asn Cys Tyr Cys Lys Lys Cys
                20                  25                  30

Cys Phe His Cys Tyr Ala Cys Phe Leu Arg Lys Gly Leu Gly Ile Thr
            35                  40                  45

Tyr His Ala Phe Arg Thr Arg Arg Lys Lys Ile Ala Ser Ala Asp Arg
        50                  55                  60

Ile Pro Val Pro Gln Gln Ser Ile Ser Ile Arg Gly Arg Asp Ser Gln
65                  70                  75                  80

Thr Thr Gln Glu Ser Gln Lys Lys Val Glu Glu Gln Ala Lys Ala Asn
                85                  90                  95

Leu Arg Ile Ser Arg Lys Asn Leu Gly Asp Glu Thr Arg Gly Pro Val
            100                 105                 110

Gly Ala Gly Asn
        115

<210> SEQ ID NO 17
<211> LENGTH: 99
<212> TYPE: PRT
<213> ORGANISM: Artificial Sequence
<220> FEATURE:
<223> OTHER INFORMATION: Tat derivative polypeptide

<400> SEQUENCE: 17

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
                20                  25                  30

Lys Lys Cys Cys Phe His Cys Tyr Ala Cys Phe Leu Gln Lys Gly Leu
            35                  40                  45

Gly Val Arg Tyr His Val Ser Arg Lys Arg Arg Lys Thr Ser Thr Gln
        50                  55                  60

Asp Asn Gln Asp Pro Ile Arg Gln Gln Ser Ile Ser Thr Val Gln Arg
65                  70                  75                  80

Asn Gly Gln Thr Thr Glu Glu Gly Lys Thr Glu Val Glu Lys Ala Ala
                85                  90                  95

Ala Ala Asn

<210> SEQ ID NO 18
<211> LENGTH: 116
<212> TYPE: PRT
<213> ORGANISM: Artificial Sequence
<220> FEATURE:
<223> OTHER INFORMATION: Tat derivative polypeptide

<400> SEQUENCE: 18

Met Ala Gln Glu Glu Gly Leu Gln Val Trp Glu Glu Leu Gln Glu Glu
1               5                   10                  15

Leu Gln Arg Pro Arg Thr Ala Cys Asn Asn Cys Tyr Cys Lys Lys Cys
                20                  25                  30

Cys Phe His Cys Tyr Ala Cys Phe Leu Arg Lys Gly Leu Gly Ile Thr
            35                  40                  45
```

```
Tyr His Ala Phe Arg Thr Arg Arg Lys Lys Ile Ala Ser Ala Asp Arg
        50                  55                  60

Ile Pro Val Pro Gln Gln Ser Ile Ser Ile Arg Gly Arg Asp Ser Gln
65                  70                  75                  80

Thr Thr Gln Glu Ser Gln Lys Lys Val Glu Glu Gln Ala Lys Ala Asn
                85                  90                  95

Leu Arg Ile Ser Arg Lys Asn Leu Gly Asp Glu Thr Arg Gly Pro Val
            100                 105                 110

Gly Ala Gly Asn
            115

<210> SEQ ID NO 19
<211> LENGTH: 108
<212> TYPE: PRT
<213> ORGANISM: Artificial Sequence
<220> FEATURE:
<223> OTHER INFORMATION: Tat derivative polypeptide

<400> SEQUENCE: 19

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
                20                  25                  30

Lys Lys Cys Cys Phe His Cys Tyr Ala Cys Phe Thr Gln Lys Gly Leu
            35                  40                  45

Gly Ile Ala Tyr Tyr Val Pro Arg Thr Arg Arg Thr Val Lys Lys Ile
        50                  55                  60

Gln Asn Asn Gln Val Pro Ile His Asn Gln Ser Ile Ser Thr Trp Thr
65                  70                  75                  80

Arg Asn Ser Gln Ala Glu Lys Lys Ser Gln Thr Lys Val Gly Gln Ala
                85                  90                  95

Ala Thr Ala Asp His Thr Pro Gly Arg Lys Asn Ser
            100                 105

<210> SEQ ID NO 20
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 20

Met Asp Lys Gly Glu Asp Glu Gln Gly Ala Tyr His Gln Asp Leu Ile
1               5                   10                  15

Glu Gln Leu Lys Ala Pro Arg Thr Ala Cys Asn Asn Cys Tyr Cys Lys
                20                  25                  30

Lys Cys Cys Phe His Cys Tyr Ala Cys Phe Leu Arg Lys Gly Leu Gly
            35                  40                  45

Ile Thr Tyr His Ala Phe Arg Thr Arg Arg Lys Lys Ile Ala Ser Ala
        50                  55                  60

Asp Arg Ile Pro Val Pro Gln Gln Ser Ile Ser Ile Arg Gly Arg Asp
65                  70                  75                  80

Ser Gln Thr Thr Gln Glu Ser Gln Lys Lys Val Glu Glu Gln Ala Lys
                85                  90                  95

Ala Asn Leu Arg Ile Ser Arg Lys Asn Leu Gly Asp Glu Thr Arg Gly
            100                 105                 110

Pro Val Gly Ala Gly Asn
```

-continued

```
                115

<210> SEQ ID NO 21
<211> LENGTH: 120
<212> TYPE: PRT
<213> ORGANISM: Artificial Sequence
<220> FEATURE:
<223> OTHER INFORMATION: Tat derivative polypeptide

<400> SEQUENCE: 21

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Phe Leu Gln Lys Gly
        35                  40                  45

Leu Gly Val Thr Tyr His Ala Pro Arg Ile Arg Arg Lys Lys Ile Ala
    50                  55                  60

Pro Leu Asp Arg Phe Pro Glu Gln Lys Gln Ser Ile Ser Thr Arg Gly
65                  70                  75                  80

Arg Asp Ser Gln Thr Thr Gln Lys Gly Gln Glu Lys Val Glu Thr Ser
                85                  90                  95

Ala Arg Thr Ala Pro Ser Leu Gly Arg Lys Asn Leu Ala Gln Gln Ser
            100                 105                 110

Gly Arg Ala Thr Gly Ala Ser Asp
        115                 120

<210> SEQ ID NO 22
<211> LENGTH: 103
<212> TYPE: PRT
<213> ORGANISM: Artificial Sequence
<220> FEATURE:
<223> OTHER INFORMATION: Tat derivative polypeptide

<400> SEQUENCE: 22

Met Asp Val Arg Ala Val Gly Ser Glu Arg Ile Glu Glu Glu Thr Leu
1               5                   10                  15

Tyr Asn Pro Arg Lys Thr Ala Cys Thr Thr Cys Tyr Cys Lys Lys Cys
            20                  25                  30

Cys Phe His Cys Gln Val Cys Phe Thr Arg Lys Gly Leu Gly Ile Ser
        35                  40                  45

Tyr Gly Arg Lys Lys Arg Arg Gln Arg Arg Ala Pro Gln Asp Ser
    50                  55                  60

Gln Thr His Gln Ala Ser Leu Ser Lys Gln Pro Ala Ser Gln Ser Arg
65                  70                  75                  80

Gly Asp Pro Thr Gly Pro Thr Glu Ser Lys Lys Val Glu Arg Glu
                85                  90                  95

Thr Glu Thr Asp Pro Phe Asp
            100

<210> SEQ ID NO 23
<211> LENGTH: 115
<212> TYPE: PRT
<213> ORGANISM: Artificial Sequence
<220> FEATURE:
<223> OTHER INFORMATION: Tat derivative polypeptide

<400> SEQUENCE: 23

Met Asp Val Arg Ala Val Gly Ser Glu Arg Ile Glu Glu Glu Thr Leu
1               5                   10                  15
```

```
Tyr Asn Pro Arg Thr Ala Cys Asn Asn Cys Tyr Cys Lys Lys Cys Cys
            20                  25                  30

Phe His Cys Tyr Ala Cys Phe Leu Arg Lys Gly Leu Gly Ile Thr Tyr
        35                  40                  45

His Ala Phe Arg Thr Arg Lys Lys Ile Ala Ser Ala Asp Arg Ile
50                  55                  60

Pro Val Pro Gln Gln Ser Ile Ser Ile Arg Gly Arg Asp Ser Gln Thr
65                  70                  75                  80

Thr Gln Glu Ser Gln Lys Lys Val Glu Glu Gln Ala Lys Ala Asn Leu
                85                  90                  95

Arg Ile Ser Arg Lys Asn Leu Gly Asp Glu Thr Arg Gly Pro Val Gly
                100                 105                 110

Ala Gly Asn
        115

<210> SEQ ID NO 24
<211> LENGTH: 109
<212> TYPE: PRT
<213> ORGANISM: Artificial Sequence
<220> FEATURE:
<223> OTHER INFORMATION: Tat derivative polypeptide

<400> SEQUENCE: 24

Met Asp Val Arg Ala Val Gly Ser Glu Arg Ile Glu Glu Glu Thr Leu
1               5                   10                  15

Tyr Asn Pro Leu Glu Thr Cys Asn Asn Thr Cys Tyr Cys Lys Glu Cys
            20                  25                  30

Cys Tyr His Cys Gln Leu Cys Phe Leu Asn Lys Gly Leu Gly Ile Trp
        35                  40                  45

Tyr Asp Arg Lys Gly Arg Arg Arg Ser Pro Lys Lys Ile Lys Ala
50                  55                  60

His Ser Ser Ser Ala Ser Asp Lys Ser Ile Ser Thr Arg Thr Arg Asn
65                  70                  75                  80

Ser Gln Pro Glu Glu Lys Gln Lys Lys Thr Leu Glu Thr Thr Leu Gly
                85                  90                  95

Thr Asp Cys Gly Pro Gly Arg Ser His Ile Tyr Ile Ser
                100                 105

<210> SEQ ID NO 25
<211> LENGTH: 102
<212> TYPE: PRT
<213> ORGANISM: Artificial Sequence
<220> FEATURE:
<223> OTHER INFORMATION: Tat derivative polypeptide

<400> SEQUENCE: 25

Met Asp Val Arg Ala Val Gly Ser Glu Arg Ile Glu Glu Glu Thr Leu
1               5                   10                  15

Tyr Asn Pro Thr Thr Ala Cys Ser Lys Cys Tyr Cys Lys Met Cys Cys
            20                  25                  30

Trp His Cys Gln Leu Cys Phe Leu Asn Lys Gly Leu Gly Ile Ser Tyr
        35                  40                  45

Gly Arg Lys Lys Arg Lys Arg Arg Gly Thr Pro Gln Ser Arg Gln
50                  55                  60

Asp His Gln Asn Pro Val Pro Lys Gln Pro Leu Pro Thr Thr Arg Gly
65                  70                  75                  80

Asn Pro Thr Asn Pro Lys Glu Ser Lys Lys Glu Val Ala Ser Lys Thr
```

Glu Thr Asn Gln Cys Asp
                100

<210> SEQ ID NO 26
<211> LENGTH: 114
<212> TYPE: PRT
<213> ORGANISM: Artificial Sequence
<220> FEATURE:
<223> OTHER INFORMATION: Tat derivative polypeptide

<400> SEQUENCE: 26

Met Ser Ser Thr Asp Gln Ile Cys Gln Thr Gln Arg Val Pro Pro Ser
1               5                   10                  15

Phe Leu Glu Gly Thr Phe Leu Glu Lys Gly Pro Pro Thr Pro Arg Lys
            20                  25                  30

Thr Ala Cys Thr Thr Cys Tyr Cys Lys Lys Cys Cys Phe His Cys Gln
        35                  40                  45

Val Cys Phe Thr Arg Lys Gly Leu Gly Ile Ser Tyr Gly Arg Lys Lys
    50                  55                  60

Arg Arg Gln Arg Arg Ala Pro Gln Asp Ser Gln Thr His Gln Ala
65                  70                  75                  80

Ser Leu Ser Lys Gln Pro Ala Ser Gln Ser Arg Gly Asp Pro Thr Gly
                85                  90                  95

Pro Thr Glu Ser Lys Lys Lys Val Glu Arg Glu Thr Glu Thr Asp Pro
                100                 105                 110

Phe Asp

<210> SEQ ID NO 27
<211> LENGTH: 126
<212> TYPE: PRT
<213> ORGANISM: Artificial Sequence
<220> FEATURE:
<223> OTHER INFORMATION: Tat derivative polypeptide

<400> SEQUENCE: 27

Met Ser Ser Thr Asp Gln Ile Cys Gln Thr Gln Arg Val Pro Pro Ser
1               5                   10                  15

Phe Leu Glu Gly Thr Phe Leu Glu Lys Gly Pro Pro Thr Pro Arg Thr
            20                  25                  30

Ala Cys Asn Asn Cys Tyr Cys Lys Cys Cys Phe His Cys Tyr Ala
        35                  40                  45

Cys Phe Leu Arg Lys Gly Leu Gly Ile Thr Tyr His Ala Phe Arg Thr
    50                  55                  60

Arg Arg Lys Lys Ile Ala Ser Ala Asp Arg Ile Pro Val Pro Gln Gln
65                  70                  75                  80

Ser Ile Ser Ile Arg Gly Arg Asp Ser Gln Thr Thr Gln Glu Ser Gln
                85                  90                  95

Lys Lys Val Glu Glu Gln Ala Lys Ala Asn Leu Arg Ile Ser Arg Lys
                100                 105                 110

Asn Leu Gly Asp Glu Thr Arg Gly Pro Val Gly Ala Gly Asn
                115                 120                 125

<210> SEQ ID NO 28
<211> LENGTH: 120
<212> TYPE: PRT
<213> ORGANISM: Artificial Sequence
<220> FEATURE:
<223> OTHER INFORMATION: Tat derivative polypeptide

<400> SEQUENCE: 28

Met Ser Ser Thr Asp Gln Ile Cys Gln Thr Gln Arg Val Pro Pro Ser
1               5                   10                  15

Phe Leu Glu Gly Thr Phe Leu Glu Lys Gly Pro Pro Thr Pro Leu Glu
            20                  25                  30

Thr Cys Asn Asn Thr Cys Tyr Cys Lys Glu Cys Cys Tyr His Cys Gln
            35                  40                  45

Leu Cys Phe Leu Asn Lys Gly Leu Gly Ile Trp Tyr Asp Arg Lys Gly
        50                  55                  60

Arg Arg Arg Arg Ser Pro Lys Lys Ile Lys Ala His Ser Ser Ser Ala
65                  70                  75                  80

Ser Asp Lys Ser Ile Ser Thr Arg Thr Arg Asn Ser Gln Pro Glu Glu
                85                  90                  95

Lys Gln Lys Lys Thr Leu Glu Thr Thr Leu Gly Thr Asp Cys Gly Pro
                100                 105                 110

Gly Arg Ser His Ile Tyr Ile Ser
            115                 120

<210> SEQ ID NO 29
<211> LENGTH: 113
<212> TYPE: PRT
<213> ORGANISM: Artificial Sequence
<220> FEATURE:
<223> OTHER INFORMATION: Tat derivative polypeptide

<400> SEQUENCE: 29

Met Ser Ser Thr Asp Gln Ile Cys Gln Thr Gln Arg Val Pro Pro Ser
1               5                   10                  15

Phe Leu Glu Gly Thr Phe Leu Glu Lys Gly Pro Pro Thr Pro Thr Thr
            20                  25                  30

Ala Cys Ser Lys Cys Tyr Cys Lys Met Cys Cys Trp His Cys Gln Leu
            35                  40                  45

Cys Phe Leu Asn Lys Gly Leu Gly Ile Ser Tyr Gly Arg Lys Lys Arg
        50                  55                  60

Lys Arg Arg Arg Gly Thr Pro Gln Ser Arg Gln Asp His Gln Asn Pro
65                  70                  75                  80

Val Pro Lys Gln Pro Leu Pro Thr Thr Arg Gly Asn Pro Thr Asn Pro
                85                  90                  95

Lys Glu Ser Lys Lys Glu Val Ala Ser Lys Thr Glu Thr Asn Gln Cys
                100                 105                 110

Asp

<210> SEQ ID NO 30
<211> LENGTH: 110
<212> TYPE: PRT
<213> ORGANISM: Artificial Sequence
<220> FEATURE:
<223> OTHER INFORMATION: Tat derivative polypeptide

<400> SEQUENCE: 30

Met Asp Gly Gln Glu Ala Gly Leu Glu Arg Gln Glu Glu Thr Leu
1               5                   10                  15

Tyr Asn Pro Phe Gln Ser Val Glu Thr Pro Arg Lys Thr Ala Cys Thr
            20                  25                  30

Thr Cys Tyr Cys Lys Lys Cys Cys Phe His Cys Gln Val Cys Phe Thr
            35                  40                  45

Arg Lys Gly Leu Gly Ile Ser Tyr Gly Arg Lys Arg Gln Arg
    50                  55                  60

Arg Arg Ala Pro Gln Asp Ser Gln Thr His Gln Ala Ser Leu Ser Lys
65              70                  75                  80

Gln Pro Ala Ser Gln Ser Arg Gly Asp Pro Thr Gly Pro Thr Glu Ser
                85                  90                  95

Lys Lys Lys Val Glu Arg Glu Thr Glu Thr Asp Pro Phe Asp
            100                 105                 110

<210> SEQ ID NO 31
<211> LENGTH: 122
<212> TYPE: PRT
<213> ORGANISM: Artificial Sequence
<220> FEATURE:
<223> OTHER INFORMATION: Tat derivative polypeptide

<400> SEQUENCE: 31

Met Asp Gly Gln Glu Ala Gly Leu Glu Arg Gln Glu Glu Glu Thr Leu
1               5                   10                  15

Tyr Asn Pro Phe Gln Ser Val Glu Thr Pro Arg Thr Ala Cys Asn Asn
                20                  25                  30

Cys Tyr Cys Lys Lys Cys Cys Phe His Cys Tyr Ala Cys Phe Leu Arg
            35                  40                  45

Lys Gly Leu Gly Ile Thr Tyr His Ala Phe Arg Thr Arg Arg Lys Lys
    50                  55                  60

Ile Ala Ser Ala Asp Arg Ile Pro Val Pro Gln Gln Ser Ile Ser Ile
65              70                  75                  80

Arg Gly Arg Asp Ser Gln Thr Thr Gln Glu Ser Gln Lys Lys Val Glu
                85                  90                  95

Glu Gln Ala Lys Ala Asn Leu Arg Ile Ser Arg Lys Asn Leu Gly Asp
            100                 105                 110

Glu Thr Arg Gly Pro Val Gly Ala Gly Asn
        115                 120

<210> SEQ ID NO 32
<211> LENGTH: 116
<212> TYPE: PRT
<213> ORGANISM: Artificial Sequence
<220> FEATURE:
<223> OTHER INFORMATION: Tat derivative polypeptide

<400> SEQUENCE: 32

Met Asp Gly Gln Glu Ala Gly Leu Glu Arg Gln Glu Glu Glu Thr Leu
1               5                   10                  15

Tyr Asn Pro Phe Gln Ser Val Glu Thr Pro Leu Glu Thr Cys Asn Asn
                20                  25                  30

Thr Cys Tyr Cys Lys Glu Cys Cys Tyr His Cys Gln Leu Cys Phe Leu
            35                  40                  45

Asn Lys Gly Leu Gly Ile Trp Tyr Asp Arg Lys Gly Arg Arg Arg Arg
    50                  55                  60

Ser Pro Lys Lys Ile Lys Ala His Ser Ser Ala Ser Asp Lys Ser
65              70                  75                  80

Ile Ser Thr Arg Thr Arg Asn Ser Gln Pro Glu Glu Lys Gln Lys Lys
                85                  90                  95

Thr Leu Glu Thr Thr Leu Gly Thr Asp Cys Gly Pro Gly Arg Ser His
            100                 105                 110

Ile Tyr Ile Ser
    115

<210> SEQ ID NO 33
<211> LENGTH: 109
<212> TYPE: PRT
<213> ORGANISM: Artificial Sequence
<220> FEATURE:
<223> OTHER INFORMATION: Tat derivative polypeptide

<400> SEQUENCE: 33

```
Met Asp Gly Gln Glu Ala Gly Leu Glu Arg Gln Glu Glu Thr Leu
1               5                   10                  15

Tyr Asn Pro Phe Gln Ser Val Glu Thr Pro Thr Thr Ala Cys Ser Lys
                20                  25                  30

Cys Tyr Cys Lys Met Cys Cys Trp His Cys Gln Leu Cys Phe Leu Asn
                35                  40                  45

Lys Gly Leu Gly Ile Ser Tyr Gly Arg Lys Lys Arg Lys Arg Arg
            50                  55                  60

Gly Thr Pro Gln Ser Arg Gln Asp His Gln Asn Pro Val Pro Lys Gln
65                  70                  75                  80

Pro Leu Pro Thr Thr Arg Gly Asn Pro Thr Asn Pro Lys Glu Ser Lys
                85                  90                  95

Lys Glu Val Ala Ser Lys Thr Glu Thr Asn Gln Cys Asp
                100                 105
```

<210> SEQ ID NO 34
<211> LENGTH: 112
<212> TYPE: PRT
<213> ORGANISM: Artificial Sequence
<220> FEATURE:
<223> OTHER INFORMATION: Tat derivative polypeptide

<400> SEQUENCE: 34

```
Met Ser Thr Gln Gly His Gln Gln Asp Gln Asp Gly Lys Gly Thr
1               5                   10                  15

Leu Glu Glu Ala Tyr Lys Thr Asn Leu Glu Ala Pro Arg Lys Thr Ala
                20                  25                  30

Cys Thr Thr Cys Tyr Cys Lys Lys Cys Cys Phe His Cys Gln Val Cys
                35                  40                  45

Phe Thr Arg Lys Gly Leu Gly Ile Ser Tyr Gly Arg Lys Lys Arg Arg
            50                  55                  60

Gln Arg Arg Arg Ala Pro Gln Asp Ser Gln Thr His Gln Ala Ser Leu
65                  70                  75                  80

Ser Lys Gln Pro Ala Ser Gln Ser Arg Gly Asp Pro Thr Gly Pro Thr
                85                  90                  95

Glu Ser Lys Lys Lys Val Glu Arg Glu Thr Glu Thr Asp Pro Phe Asp
                100                 105                 110
```

<210> SEQ ID NO 35
<211> LENGTH: 124
<212> TYPE: PRT
<213> ORGANISM: Artificial Sequence
<220> FEATURE:
<223> OTHER INFORMATION: Tat derivative polypeptide

<400> SEQUENCE: 35

```
Met Ser Thr Gln Gly His Gln Gln Asp Gln Asp Gly Lys Gly Thr
1               5                   10                  15

Leu Glu Glu Ala Tyr Lys Thr Asn Leu Glu Ala Pro Arg Thr Ala Cys
                20                  25                  30
```

Asn Asn Cys Tyr Cys Lys Lys Cys Phe His Cys Tyr Ala Cys Phe
            35                  40                  45

Leu Arg Lys Gly Leu Gly Ile Thr Tyr His Ala Phe Arg Thr Arg Arg
 50                  55                  60

Lys Lys Ile Ala Ser Ala Asp Arg Ile Pro Val Pro Gln Gln Ser Ile
 65                  70                  75                  80

Ser Ile Arg Gly Arg Asp Ser Gln Thr Thr Gln Glu Ser Gln Lys Lys
                 85                  90                  95

Val Glu Glu Gln Ala Lys Ala Asn Leu Arg Ile Ser Arg Lys Asn Leu
                100                 105                 110

Gly Asp Glu Thr Arg Gly Pro Val Gly Ala Gly Asn
            115                 120

<210> SEQ ID NO 36
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 36

Met Ser Thr Gln Gly His Gln Gln Asp Gln Asp Gln Gly Lys Gly Thr
 1               5                  10                  15

Leu Glu Glu Ala Tyr Lys Thr Asn Leu Glu Ala Pro Leu Glu Thr Cys
                 20                  25                  30

Asn Asn Thr Cys Tyr Cys Lys Glu Cys Cys Tyr His Cys Gln Leu Cys
            35                  40                  45

Phe Leu Asn Lys Gly Leu Gly Ile Trp Tyr Asp Arg Lys Gly Arg Arg
 50                  55                  60

Arg Arg Ser Pro Lys Lys Ile Lys Ala His Ser Ser Ser Ala Ser Asp
 65                  70                  75                  80

Lys Ser Ile Ser Thr Arg Thr Arg Asn Ser Gln Pro Glu Glu Lys Gln
                 85                  90                  95

Lys Lys Thr Leu Glu Thr Thr Leu Gly Thr Asp Cys Gly Pro Gly Arg
                100                 105                 110

Ser His Ile Tyr Ile Ser
            115

<210> SEQ ID NO 37
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 37

Met Ser Thr Gln Gly His Gln Gln Asp Gln Asp Gln Gly Lys Gly Thr
 1               5                  10                  15

Leu Glu Glu Ala Tyr Lys Thr Asn Leu Glu Ala Pro Thr Thr Ala Cys
                 20                  25                  30

Ser Lys Cys Tyr Cys Lys Met Cys Cys Trp His Cys Gln Leu Cys Phe
            35                  40                  45

Leu Asn Lys Gly Leu Gly Ile Ser Tyr Gly Arg Lys Lys Arg Lys Arg
 50                  55                  60

Arg Arg Gly Thr Pro Gln Ser Arg Gln Asp His Gln Asn Pro Val Pro
 65                  70                  75                  80

Lys Gln Pro Leu Pro Thr Thr Arg Gly Asn Pro Thr Asn Pro Lys Glu
                 85                  90                  95

```
Ser Lys Lys Glu Val Ala Ser Lys Thr Glu Thr Asn Gln Cys Asp
            100                 105                 110
```

```
<210> SEQ ID NO 38
<211> LENGTH: 114
<212> TYPE: PRT
<213> ORGANISM: Artificial Sequence
<220> FEATURE:
<223> OTHER INFORMATION: Tat derivative polypeptide

<400> SEQUENCE: 38

Met Gln Gln Pro Glu Gln Glu Gln His Thr Gln Gln Lys Gln His Leu
1               5                   10                  15

Asp Gln Leu Glu Glu Ile Tyr Lys Glu Ala Ile Thr Asp Pro Arg Lys
            20                  25                  30

Thr Ala Cys Thr Thr Cys Tyr Cys Lys Lys Cys Cys Phe His Cys Gln
        35                  40                  45

Val Cys Phe Thr Arg Lys Gly Leu Gly Ile Ser Tyr Gly Arg Lys Lys
    50                  55                  60

Arg Arg Gln Arg Arg Ala Pro Gln Asp Ser Gln Thr His Gln Ala
65                  70                  75                  80

Ser Leu Ser Lys Gln Pro Ala Ser Gln Ser Arg Gly Asp Pro Thr Gly
                85                  90                  95

Pro Thr Glu Ser Lys Lys Val Glu Arg Glu Thr Glu Thr Asp Pro
            100                 105                 110

Phe Asp
```

```
<210> SEQ ID NO 39
<211> LENGTH: 126
<212> TYPE: PRT
<213> ORGANISM: Artificial Sequence
<220> FEATURE:
<223> OTHER INFORMATION: Tat derivative polypeptide

<400> SEQUENCE: 39

Met Gln Gln Pro Glu Gln Glu Gln His Thr Gln Gln Lys Gln His Leu
1               5                   10                  15

Asp Gln Leu Glu Glu Ile Tyr Lys Glu Ala Ile Thr Asp Pro Arg Thr
            20                  25                  30

Ala Cys Asn Asn Cys Tyr Cys Lys Lys Cys Cys Phe His Cys Tyr Ala
        35                  40                  45

Cys Phe Leu Arg Lys Gly Leu Gly Ile Thr Tyr His Ala Phe Arg Thr
    50                  55                  60

Arg Arg Lys Lys Ile Ala Ser Ala Asp Arg Ile Pro Val Pro Gln Gln
65                  70                  75                  80

Ser Ile Ser Ile Arg Gly Arg Asp Ser Gln Thr Thr Gln Glu Ser Gln
                85                  90                  95

Lys Lys Val Glu Glu Gln Ala Lys Ala Asn Leu Arg Ile Ser Arg Lys
            100                 105                 110

Asn Leu Gly Asp Glu Thr Arg Gly Pro Val Gly Ala Gly Asn
        115                 120                 125
```

```
<210> SEQ ID NO 40
<211> LENGTH: 120
<212> TYPE: PRT
<213> ORGANISM: Artificial Sequence
<220> FEATURE:
<223> OTHER INFORMATION: Tat derivative polypeptide
```

-continued

<400> SEQUENCE: 40

Met Gln Gln Pro Glu Gln Glu Gln His Thr Gln Gln Lys Gln His Leu
1               5                   10                  15

Asp Gln Leu Glu Glu Ile Tyr Lys Glu Ala Ile Thr Asp Pro Leu Glu
            20                  25                  30

Thr Cys Asn Asn Thr Cys Tyr Cys Lys Glu Cys Cys Tyr His Cys Gln
        35                  40                  45

Leu Cys Phe Leu Asn Lys Gly Leu Gly Ile Trp Tyr Asp Arg Lys Gly
    50                  55                  60

Arg Arg Arg Arg Ser Pro Lys Lys Ile Lys Ala His Ser Ser Ser Ala
65                  70                  75                  80

Ser Asp Lys Ser Ile Ser Thr Arg Thr Arg Asn Ser Gln Pro Glu Glu
                85                  90                  95

Lys Gln Lys Lys Thr Leu Glu Thr Thr Leu Gly Thr Asp Cys Gly Pro
            100                 105                 110

Gly Arg Ser His Ile Tyr Ile Ser
            115                 120

<210> SEQ ID NO 41
<211> LENGTH: 113
<212> TYPE: PRT
<213> ORGANISM: Artificial Sequence
<220> FEATURE:
<223> OTHER INFORMATION: Tat derivative polypeptide

<400> SEQUENCE: 41

Met Gln Gln Pro Glu Gln Glu Gln His Thr Gln Gln Lys Gln His Leu
1               5                   10                  15

Asp Gln Leu Glu Glu Ile Tyr Lys Glu Ala Ile Thr Asp Pro Thr Thr
            20                  25                  30

Ala Cys Ser Lys Cys Tyr Cys Lys Met Cys Cys Trp His Cys Gln Leu
        35                  40                  45

Cys Phe Leu Asn Lys Gly Leu Gly Ile Ser Tyr Gly Arg Lys Lys Arg
    50                  55                  60

Lys Arg Arg Arg Gly Thr Pro Gln Ser Arg Gln Asp His Gln Asn Pro
65                  70                  75                  80

Val Pro Lys Gln Pro Leu Pro Thr Thr Arg Gly Asn Pro Thr Asn Pro
                85                  90                  95

Lys Glu Ser Lys Lys Glu Val Ala Ser Lys Thr Glu Thr Asn Gln Cys
            100                 105                 110

Asp

<210> SEQ ID NO 42
<211> LENGTH: 130
<212> TYPE: PRT
<213> ORGANISM: Artificial Sequence
<220> FEATURE:
<223> OTHER INFORMATION: Tat derivative polypeptide

<400> SEQUENCE: 42

Met Glu Thr Pro Leu Lys Glu Gln Glu Ser Ser Leu Arg Ser Ser
1               5                   10                  15

Glu Pro Ser Ser Cys Thr Ser Glu Ala Val Ala Ala Thr Pro Gly Leu
            20                  25                  30

Ala Asn Gln Glu Glu Glu Ile Leu Trp Gln Leu Tyr Arg Pro Arg Lys
        35                  40                  45

Thr Ala Cys Thr Thr Cys Tyr Cys Lys Lys Cys Cys Phe His Cys Gln

```
                50                  55                  60
Val Cys Phe Thr Arg Lys Gly Leu Gly Ile Ser Tyr Gly Arg Lys Lys
 65                  70                  75                  80

Arg Arg Gln Arg Arg Ala Pro Gln Asp Ser Gln Thr His Gln Ala
                 85                  90                  95

Ser Leu Ser Lys Gln Pro Ala Ser Gln Ser Arg Gly Asp Thr Gly
                100                 105                 110

Pro Thr Glu Ser Lys Lys Val Glu Arg Glu Thr Glu Thr Asp Pro
            115                 120                 125

Phe Asp
    130

<210> SEQ ID NO 43
<211> LENGTH: 142
<212> TYPE: PRT
<213> ORGANISM: Artificial Sequence
<220> FEATURE:
<223> OTHER INFORMATION: Tat derivative polypeptide

<400> SEQUENCE: 43

Met Glu Thr Pro Leu Lys Glu Gln Glu Ser Ser Leu Arg Ser Ser Ser
  1               5                  10                  15

Glu Pro Ser Ser Cys Thr Ser Glu Ala Val Ala Ala Thr Pro Gly Leu
                 20                  25                  30

Ala Asn Gln Glu Glu Glu Ile Leu Trp Gln Leu Tyr Arg Pro Arg Thr
             35                  40                  45

Ala Cys Asn Asn Cys Tyr Cys Lys Lys Cys Cys Phe His Cys Tyr Ala
 50                  55                  60

Cys Phe Leu Arg Lys Gly Leu Gly Ile Thr Tyr His Ala Phe Arg Thr
 65                  70                  75                  80

Arg Arg Lys Lys Ile Ala Ser Ala Asp Arg Ile Pro Val Pro Gln Gln
                 85                  90                  95

Ser Ile Ser Ile Arg Gly Arg Asp Ser Gln Thr Thr Gln Glu Ser Gln
                100                 105                 110

Lys Lys Val Glu Glu Gln Ala Lys Ala Asn Leu Arg Ile Ser Arg Lys
            115                 120                 125

Asn Leu Gly Asp Glu Thr Arg Gly Pro Val Gly Ala Gly Asn
        130                 135                 140

<210> SEQ ID NO 44
<211> LENGTH: 136
<212> TYPE: PRT
<213> ORGANISM: Artificial Sequence
<220> FEATURE:
<223> OTHER INFORMATION: Tat derivative polypeptide

<400> SEQUENCE: 44

Met Glu Thr Pro Leu Lys Glu Gln Glu Ser Ser Leu Arg Ser Ser Ser
  1               5                  10                  15

Glu Pro Ser Ser Cys Thr Ser Glu Ala Val Ala Ala Thr Pro Gly Leu
                 20                  25                  30

Ala Asn Gln Glu Glu Glu Ile Leu Trp Gln Leu Tyr Arg Pro Leu Glu
             35                  40                  45

Thr Cys Asn Asn Thr Cys Tyr Cys Lys Glu Cys Cys Tyr His Cys Gln
 50                  55                  60

Leu Cys Phe Leu Asn Lys Gly Leu Gly Ile Trp Tyr Asp Arg Lys Gly
 65                  70                  75                  80
```

```
Arg Arg Arg Arg Ser Pro Lys Lys Ile Lys Ala His Ser Ser Ser Ala
            85                  90                  95

Ser Asp Lys Ser Ile Ser Thr Arg Thr Arg Asn Ser Gln Pro Glu Glu
        100                 105                 110

Lys Gln Lys Lys Thr Leu Glu Thr Thr Leu Gly Thr Asp Cys Gly Pro
        115                 120                 125

Gly Arg Ser His Ile Tyr Ile Ser
        130                 135

<210> SEQ ID NO 45
<211> LENGTH: 129
<212> TYPE: PRT
<213> ORGANISM: Artificial Sequence
<220> FEATURE:
<223> OTHER INFORMATION: Tat derivative polypeptide

<400> SEQUENCE: 45

Met Glu Thr Pro Leu Lys Glu Gln Glu Ser Ser Leu Arg Ser Ser Ser
1               5                   10                  15

Glu Pro Ser Ser Cys Thr Ser Glu Ala Val Ala Ala Thr Pro Gly Leu
            20                  25                  30

Ala Asn Gln Glu Glu Glu Ile Leu Trp Gln Leu Tyr Arg Pro Thr Thr
        35                  40                  45

Ala Cys Ser Lys Cys Tyr Cys Lys Met Cys Cys Trp His Cys Gln Leu
50                  55                  60

Cys Phe Leu Asn Lys Gly Leu Gly Ile Ser Tyr Gly Arg Lys Lys Arg
65                  70                  75                  80

Lys Arg Arg Arg Gly Thr Pro Gln Ser Arg Gln Asp His Gln Asn Pro
                85                  90                  95

Val Pro Lys Gln Pro Leu Pro Thr Thr Arg Gly Asn Pro Thr Asn Pro
            100                 105                 110

Lys Glu Ser Lys Lys Glu Val Ala Ser Lys Thr Glu Thr Asn Gln Cys
        115                 120                 125

Asp

<210> SEQ ID NO 46
<211> LENGTH: 106
<212> TYPE: PRT
<213> ORGANISM: Artificial Sequence
<220> FEATURE:
<223> OTHER INFORMATION: Tat derivative polypeptide

<400> SEQUENCE: 46

Met Asp Lys Gly Glu Glu Glu Arg Thr Val Leu His Gln Asp Leu Ile
1               5                   10                  15

Arg Gln Tyr Lys Lys Pro Arg Lys Leu Thr Ala Cys Thr Cys Tyr Cys
            20                  25                  30

Lys Lys Cys Cys Phe His Cys Gln Val Cys Phe Thr Arg Lys Gly Leu
        35                  40                  45

Gly Ile Ser Tyr Gly Arg Lys Lys Arg Arg Gln Arg Arg Arg Ala Pro
50                  55                  60

Gln Asp Ser Gln Thr His Gln Ala Ser Leu Ser Lys Gln Pro Ala Ser
65                  70                  75                  80

Gln Ser Arg Gly Asp Pro Thr Gly Pro Thr Glu Ser Lys Lys Lys Val
            85                  90                  95

Glu Arg Glu Thr Glu Thr Asp Pro Phe Asp
            100                 105
```

<210> SEQ ID NO 47
<211> LENGTH: 118
<212> TYPE: PRT
<213> ORGANISM: Artificial Sequence
<220> FEATURE:
<223> OTHER INFORMATION: Tat derivative polypeptide

<400> SEQUENCE: 47

```
Met Asp Lys Gly Glu Glu Glu Arg Thr Val Leu His Gln Asp Leu Ile
1               5                   10                  15

Arg Gln Tyr Lys Lys Pro Arg Thr Ala Cys Asn Asn Cys Tyr Cys Lys
            20                  25                  30

Lys Cys Cys Phe His Cys Tyr Ala Cys Phe Leu Arg Lys Gly Leu Gly
        35                  40                  45

Ile Thr Tyr His Ala Phe Arg Thr Arg Lys Lys Ile Ala Ser Ala
    50                  55                  60

Asp Arg Ile Pro Val Pro Gln Gln Ser Ile Ser Ile Arg Gly Arg Asp
65                  70                  75                  80

Ser Gln Thr Thr Gln Glu Ser Gln Lys Lys Val Glu Glu Gln Ala Lys
                85                  90                  95

Ala Asn Leu Arg Ile Ser Arg Lys Asn Leu Gly Asp Glu Thr Arg Gly
            100                 105                 110

Pro Val Gly Ala Gly Asn
        115
```

<210> SEQ ID NO 48
<211> LENGTH: 112
<212> TYPE: PRT
<213> ORGANISM: Artificial Sequence
<220> FEATURE:
<223> OTHER INFORMATION: Tat derivative polypeptide

<400> SEQUENCE: 48

```
Met Asp Lys Gly Glu Glu Glu Arg Thr Val Leu His Gln Asp Leu Ile
1               5                   10                  15

Arg Gln Tyr Lys Lys Pro Leu Glu Thr Cys Asn Asn Thr Cys Tyr Cys
            20                  25                  30

Lys Glu Cys Cys Tyr His Cys Gln Leu Cys Phe Leu Asn Lys Gly Leu
        35                  40                  45

Gly Ile Trp Tyr Asp Arg Lys Gly Arg Arg Arg Ser Pro Lys Lys
    50                  55                  60

Ile Lys Ala His Ser Ser Ser Ala Ser Asp Lys Ser Ile Ser Thr Arg
65                  70                  75                  80

Thr Arg Asn Ser Gln Pro Glu Glu Lys Gln Lys Lys Thr Leu Glu Thr
                85                  90                  95

Thr Leu Gly Thr Asp Cys Gly Pro Gly Arg Ser His Ile Tyr Ile Ser
            100                 105                 110
```

<210> SEQ ID NO 49
<211> LENGTH: 105
<212> TYPE: PRT
<213> ORGANISM: Artificial Sequence
<220> FEATURE:
<223> OTHER INFORMATION: Tat derivative polypeptide

<400> SEQUENCE: 49

```
Met Asp Lys Gly Glu Glu Glu Arg Thr Val Leu His Gln Asp Leu Ile
1               5                   10                  15

Arg Gln Tyr Lys Lys Pro Thr Thr Ala Cys Ser Lys Cys Tyr Cys Lys
```

-continued

```
                20                  25                  30
Met Cys Cys Trp His Cys Gln Leu Cys Phe Leu Asn Lys Gly Leu Gly
            35                  40                  45
Ile Ser Tyr Gly Arg Lys Lys Arg Arg Arg Arg Gly Thr Pro Gln
 50                  55                  60
Ser Arg Gln Asp His Gln Asn Pro Val Pro Lys Gln Pro Leu Pro Thr
 65                  70                  75                  80
Thr Arg Gly Asn Pro Thr Asn Pro Lys Glu Ser Lys Lys Glu Val Ala
                85                  90                  95
Ser Lys Thr Glu Thr Asn Gln Cys Asp
            100                 105

<210> SEQ ID NO 50
<211> LENGTH: 105
<212> TYPE: PRT
<213> ORGANISM: Artificial Sequence
<220> FEATURE:
<223> OTHER INFORMATION: Tat derivative polypeptide

<400> SEQUENCE: 50

Met Gln Pro Leu Gln Asn Arg Pro Asp Leu Gly Glu Glu Ile Leu Ser
 1               5                  10                  15
Gln Leu Tyr Arg Pro Arg Lys Thr Ala Cys Thr Thr Cys Tyr Cys Lys
                20                  25                  30
Lys Cys Cys Phe His Cys Gln Val Cys Phe Thr Arg Lys Gly Leu Gly
            35                  40                  45
Ile Ser Tyr Gly Arg Lys Lys Arg Arg Gln Arg Arg Ala Pro Gln
 50                  55                  60
Asp Ser Gln Thr His Gln Ala Ser Leu Ser Lys Gln Pro Ala Ser Gln
 65                  70                  75                  80
Ser Arg Gly Asp Pro Thr Gly Pro Thr Glu Ser Lys Lys Lys Val Glu
                85                  90                  95
Arg Glu Thr Glu Thr Asp Pro Phe Asp
            100                 105

<210> SEQ ID NO 51
<211> LENGTH: 117
<212> TYPE: PRT
<213> ORGANISM: Artificial Sequence
<220> FEATURE:
<223> OTHER INFORMATION: Tat derivative polypeptide

<400> SEQUENCE: 51

Met Gln Pro Leu Gln Asn Arg Pro Asp Leu Gly Glu Glu Ile Leu Ser
 1               5                  10                  15
Gln Leu Tyr Arg Pro Arg Thr Ala Cys Asn Asn Cys Tyr Cys Lys Lys
                20                  25                  30
Cys Cys Phe His Cys Tyr Ala Cys Phe Leu Arg Lys Gly Leu Gly Ile
            35                  40                  45
Thr Tyr His Ala Phe Arg Thr Arg Arg Lys Lys Ile Ala Ser Ala Asp
         50                  55                  60
Arg Ile Pro Val Pro Gln Gln Ser Ile Ser Ile Arg Gly Arg Asp Ser
 65                  70                  75                  80
Gln Thr Thr Gln Glu Ser Gln Lys Lys Val Glu Glu Gln Ala Lys Ala
                85                  90                  95
Asn Leu Arg Ile Ser Arg Lys Asn Leu Gly Asp Glu Thr Arg Gly Pro
            100                 105                 110
```

Val Gly Ala Gly Asn
        115

<210> SEQ ID NO 52
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 52

Met Gln Pro Leu Gln Asn Arg Pro Asp Leu Gly Glu Glu Ile Leu Ser
1               5                   10                  15

Gln Leu Tyr Arg Pro Leu Glu Thr Cys Asn Asn Thr Cys Tyr Cys Lys
            20                  25                  30

Glu Cys Cys Tyr His Cys Gln Leu Cys Phe Leu Asn Lys Gly Leu Gly
        35                  40                  45

Ile Trp Tyr Asp Arg Lys Gly Arg Arg Arg Ser Pro Lys Lys Ile
    50                  55                  60

Lys Ala His Ser Ser Ser Ala Ser Asp Lys Ser Ile Ser Thr Arg Thr
65                  70                  75                  80

Arg Asn Ser Gln Pro Glu Glu Lys Gln Lys Thr Leu Glu Thr Thr
                85                  90                  95

Leu Gly Thr Asp Cys Gly Pro Gly Arg Ser His Ile Tyr Ile Ser
            100                 105                 110

<210> SEQ ID NO 53
<211> LENGTH: 104
<212> TYPE: PRT
<213> ORGANISM: Artificial Sequence
<220> FEATURE:
<223> OTHER INFORMATION: Tat derivative polypeptide

<400> SEQUENCE: 53

Met Gln Pro Leu Gln Asn Arg Pro Asp Leu Gly Glu Glu Ile Leu Ser
1               5                   10                  15

Gln Leu Tyr Arg Pro Thr Thr Ala Cys Ser Lys Cys Tyr Cys Lys Met
            20                  25                  30

Cys Cys Trp His Cys Gln Leu Cys Phe Leu Asn Lys Gly Leu Gly Ile
        35                  40                  45

Ser Tyr Gly Arg Lys Lys Arg Lys Arg Arg Gly Thr Pro Gln Ser
    50                  55                  60

Arg Gln Asp His Gln Asn Pro Val Pro Lys Gln Pro Leu Pro Thr Thr
65                  70                  75                  80

Arg Gly Asn Pro Thr Asn Pro Lys Glu Ser Lys Lys Glu Val Ala Ser
                85                  90                  95

Lys Thr Glu Thr Asn Gln Cys Asp
            100

<210> SEQ ID NO 54
<211> LENGTH: 130
<212> TYPE: PRT
<213> ORGANISM: Artificial Sequence
<220> FEATURE:
<223> OTHER INFORMATION: Tat derivative polypeptide

<400> SEQUENCE: 54

Met Glu Thr Pro Leu Lys Glu Gln Glu Ser Ser Leu Glu Ser Ser Arg
1               5                   10                  15

Glu His Ser Ser Ser Ile Ser Glu Val Asp Ala Asp Thr Pro Glu Ser

```
                20                  25                  30
Ala Ser Leu Glu Glu Glu Ile Leu Ser Gln Leu Tyr Arg Pro Arg Lys
                35                  40                  45

Thr Ala Cys Thr Thr Cys Tyr Cys Lys Lys Cys Cys Phe His Cys Gln
            50                  55                  60

Val Cys Phe Thr Arg Lys Gly Leu Gly Ile Ser Tyr Gly Arg Lys Lys
 65                 70                  75                  80

Arg Arg Gln Arg Arg Ala Pro Gln Asp Ser Gln Thr His Gln Ala
                85                  90                  95

Ser Leu Ser Lys Gln Pro Ala Ser Gln Ser Arg Gly Asp Pro Thr Gly
                100                 105                 110

Pro Thr Glu Ser Lys Lys Lys Val Glu Arg Glu Thr Glu Thr Asp Pro
                115                 120                 125

Phe Asp
    130
```

<210> SEQ ID NO 55
<211> LENGTH: 142
<212> TYPE: PRT
<213> ORGANISM: Artificial Sequence
<220> FEATURE:
<223> OTHER INFORMATION: Tat derivative polypeptide

<400> SEQUENCE: 55

```
Met Glu Thr Pro Leu Lys Glu Gln Glu Ser Ser Leu Glu Ser Ser Arg
 1               5                  10                  15

Glu His Ser Ser Ser Ile Ser Glu Val Asp Ala Asp Thr Pro Glu Ser
                20                  25                  30

Ala Ser Leu Glu Glu Glu Ile Leu Ser Gln Leu Tyr Arg Pro Arg Thr
                35                  40                  45

Ala Cys Asn Asn Cys Tyr Cys Lys Lys Cys Cys Phe His Cys Tyr Ala
            50                  55                  60

Cys Phe Leu Arg Lys Gly Leu Gly Ile Thr Tyr His Ala Phe Arg Thr
 65                 70                  75                  80

Arg Arg Lys Lys Ile Ala Ser Ala Asp Arg Ile Pro Val Pro Gln Gln
                85                  90                  95

Ser Ile Ser Ile Arg Gly Arg Asp Ser Gln Thr Thr Gln Glu Ser Gln
                100                 105                 110

Lys Lys Val Glu Glu Gln Ala Lys Ala Asn Leu Arg Ile Ser Arg Lys
                115                 120                 125

Asn Leu Gly Asp Glu Thr Arg Gly Pro Val Gly Ala Gly Asn
            130                 135                 140
```

<210> SEQ ID NO 56
<211> LENGTH: 129
<212> TYPE: PRT
<213> ORGANISM: Artificial Sequence
<220> FEATURE:
<223> OTHER INFORMATION: Tat derivative polypeptide

<400> SEQUENCE: 56

```
Met Glu Thr Pro Leu Lys Glu Gln Glu Ser Ser Leu Glu Ser Ser Arg
 1               5                  10                  15

Glu His Ser Ser Ser Ile Ser Glu Val Asp Ala Asp Thr Pro Glu Ser
                20                  25                  30

Ala Ser Leu Glu Glu Glu Ile Leu Ser Gln Leu Tyr Arg Pro Thr Thr
                35                  40                  45
```

```
Ala Cys Ser Lys Cys Tyr Cys Lys Met Cys Cys Trp His Cys Gln Leu
    50              55                  60
Cys Phe Leu Asn Lys Gly Leu Gly Ile Ser Tyr Gly Arg Lys Lys Arg
65              70                  75                  80
Lys Arg Arg Arg Gly Thr Pro Gln Ser Arg Gln Asp His Gln Asn Pro
                85                  90                  95
Val Pro Lys Gln Pro Leu Pro Thr Thr Arg Gly Asn Pro Thr Asn Pro
            100                 105                 110
Lys Glu Ser Lys Lys Glu Val Ala Ser Lys Thr Glu Thr Asn Gln Cys
            115                 120                 125
Asp
```

<210> SEQ ID NO 57
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 57

```
Met Asp Ala Gly Lys Ala Val Ser Asp Lys Lys Glu Gly Asp Val Thr
1               5                   10                  15
Pro Tyr Asp Pro Phe Arg Asp Arg Thr Thr Pro Arg Lys Thr Ala Cys
                20                  25                  30
Thr Thr Cys Tyr Cys Lys Lys Cys Cys Phe His Cys Gln Val Cys Phe
                35                  40                  45
Thr Arg Lys Gly Leu Gly Ile Ser Tyr Gly Arg Lys Lys Arg Arg Gln
            50                  55                  60
Arg Arg Arg Ala Pro Gln Asp Ser Gln Thr His Gln Ala Ser Leu Ser
65              70                  75                  80
Lys Gln Pro Ala Ser Gln Ser Arg Gly Asp Pro Thr Gly Pro Thr Glu
                85                  90                  95
Ser Lys Lys Lys Val Glu Arg Glu Thr Glu Thr Asp Pro Phe Asp
                100                 105                 110
```

<210> SEQ ID NO 58
<211> LENGTH: 123
<212> TYPE: PRT
<213> ORGANISM: Artificial Sequence
<220> FEATURE:
<223> OTHER INFORMATION: Tat derivative polypeptide

<400> SEQUENCE: 58

```
Met Asp Ala Gly Lys Ala Val Ser Asp Lys Lys Glu Gly Asp Val Thr
1               5                   10                  15
Pro Tyr Asp Pro Phe Arg Asp Arg Thr Thr Pro Arg Thr Ala Cys Asn
                20                  25                  30
Asn Cys Tyr Cys Lys Lys Cys Cys Phe His Cys Tyr Ala Cys Phe Leu
            35                  40                  45
Arg Lys Gly Leu Gly Ile Thr Tyr His Ala Phe Arg Thr Arg Arg Lys
        50                  55                  60
Lys Ile Ala Ser Ala Asp Arg Ile Pro Val Pro Gln Gln Ser Ile Ser
65              70                  75                  80
Ile Arg Gly Arg Asp Ser Gln Thr Thr Gln Glu Ser Gln Lys Lys Val
                85                  90                  95
Glu Glu Gln Ala Lys Ala Asn Leu Arg Ile Ser Arg Lys Asn Leu Gly
                100                 105                 110
```

```
Asp Glu Thr Arg Gly Pro Val Gly Ala Gly Asn
        115                 120

<210> SEQ ID NO 59
<211> LENGTH: 110
<212> TYPE: PRT
<213> ORGANISM: Artificial Sequence
<220> FEATURE:
<223> OTHER INFORMATION: Tat derivative polypeptide

<400> SEQUENCE: 59

Met Asp Ala Gly Lys Ala Val Ser Asp Lys Lys Glu Gly Asp Val Thr
1               5                   10                  15

Pro Tyr Asp Pro Phe Arg Asp Arg Thr Thr Pro Thr Thr Ala Cys Ser
            20                  25                  30

Lys Cys Tyr Cys Lys Met Cys Cys Trp His Cys Gln Leu Cys Phe Leu
        35                  40                  45

Asn Lys Gly Leu Gly Ile Ser Tyr Gly Arg Lys Lys Arg Lys Arg Arg
    50                  55                  60

Arg Gly Thr Pro Gln Ser Arg Gln Asp His Gln Asn Pro Val Pro Lys
65                  70                  75                  80

Gln Pro Leu Pro Thr Thr Arg Gly Asn Pro Thr Asn Pro Lys Glu Ser
                85                  90                  95

Lys Lys Glu Val Ala Ser Lys Thr Glu Thr Asn Gln Cys Asp
            100                 105                 110

<210> SEQ ID NO 60
<211> LENGTH: 117
<212> TYPE: PRT
<213> ORGANISM: Artificial Sequence
<220> FEATURE:
<223> OTHER INFORMATION: Tat derivative polypeptide

<400> SEQUENCE: 60

Met Glu Pro Ser Gly Lys Glu Asp His Asn Cys Pro Pro Gln Asp Ser
1               5                   10                  15

Gly Gln Glu Glu Ile Asp Tyr Lys Gln Leu Leu Glu Glu Tyr Tyr Gln
            20                  25                  30

Pro Arg Lys Thr Ala Cys Thr Thr Cys Tyr Cys Lys Lys Cys Cys Phe
        35                  40                  45

His Cys Gln Val Cys Phe Thr Arg Lys Gly Leu Gly Ile Ser Tyr Gly
    50                  55                  60

Arg Lys Lys Arg Arg Gln Arg Arg Ala Pro Gln Asp Ser Gln Thr
65                  70                  75                  80

His Gln Ala Ser Leu Ser Lys Gln Pro Ala Ser Gln Ser Arg Gly Asp
                85                  90                  95

Pro Thr Gly Pro Thr Glu Ser Lys Lys Val Glu Arg Glu Thr Glu
            100                 105                 110

Thr Asp Pro Phe Asp
        115

<210> SEQ ID NO 61
<211> LENGTH: 129
<212> TYPE: PRT
<213> ORGANISM: Artificial Sequence
<220> FEATURE:
<223> OTHER INFORMATION: Tat derivative polypeptide

<400> SEQUENCE: 61

Met Glu Pro Ser Gly Lys Glu Asp His Asn Cys Pro Pro Gln Asp Ser
```

```
1               5                   10                  15
Gly Gln Glu Glu Ile Asp Tyr Lys Gln Leu Leu Glu Glu Tyr Tyr Gln
                20                  25                  30

Pro Arg Thr Ala Cys Asn Asn Cys Tyr Cys Lys Lys Cys Cys Phe His
            35                  40                  45

Cys Tyr Ala Cys Phe Leu Arg Lys Gly Leu Gly Ile Thr Tyr His Ala
        50                  55                  60

Phe Arg Thr Arg Lys Lys Ile Ala Ser Ala Asp Arg Ile Pro Val
65                  70                  75                  80

Pro Gln Gln Ser Ile Ser Ile Arg Gly Arg Asp Ser Gln Thr Thr Gln
                85                  90                  95

Glu Ser Gln Lys Lys Val Glu Glu Gln Ala Lys Ala Asn Leu Arg Ile
                100                 105                 110

Ser Arg Lys Asn Leu Gly Asp Glu Thr Arg Gly Pro Val Gly Ala Gly
                115                 120                 125

Asn
```

<210> SEQ ID NO 62
<211> LENGTH: 123
<212> TYPE: PRT
<213> ORGANISM: Artificial Sequence
<220> FEATURE:
<223> OTHER INFORMATION: Tat derivative polypeptide

<400> SEQUENCE: 62

```
Met Glu Pro Ser Gly Lys Glu Asp His Asn Cys Pro Pro Gln Asp Ser
1               5                   10                  15

Gly Gln Glu Glu Ile Asp Tyr Lys Gln Leu Leu Glu Glu Tyr Tyr Gln
                20                  25                  30

Pro Leu Glu Thr Cys Asn Asn Thr Cys Tyr Cys Lys Glu Cys Cys Tyr
            35                  40                  45

His Cys Gln Leu Cys Phe Leu Asn Lys Gly Leu Gly Ile Trp Tyr Asp
        50                  55                  60

Arg Lys Gly Arg Arg Arg Ser Pro Lys Lys Ile Lys Ala His Ser
65                  70                  75                  80

Ser Ser Ala Ser Asp Lys Ser Ile Ser Thr Arg Thr Arg Asn Ser Gln
                85                  90                  95

Pro Glu Leu Lys Gln Lys Lys Thr Leu Glu Thr Thr Leu Gly Thr Asp
                100                 105                 110

Cys Gly Pro Gly Arg Ser His Ile Tyr Ile Ser
            115                 120
```

<210> SEQ ID NO 63
<211> LENGTH: 116
<212> TYPE: PRT
<213> ORGANISM: Artificial Sequence
<220> FEATURE:
<223> OTHER INFORMATION: Tat derivative polypeptide

<400> SEQUENCE: 63

```
Met Glu Pro Ser Gly Lys Glu Asp His Asn Cys Pro Pro Gln Asp Ser
1               5                   10                  15

Gly Gln Glu Glu Ile Asp Tyr Lys Gln Leu Leu Glu Glu Tyr Tyr Gln
                20                  25                  30

Pro Thr Thr Ala Cys Ser Lys Cys Tyr Cys Lys Met Cys Cys Trp His
            35                  40                  45

Cys Gln Leu Cys Phe Leu Asn Lys Gly Leu Gly Ile Ser Tyr Gly Arg
```

-continued

```
                        50                  55                  60
Lys Lys Arg Lys Arg Arg Gly Thr Pro Gln Ser Arg Gln Asp His
 65                  70                  75                  80

Gln Asn Pro Val Pro Lys Gln Pro Leu Pro Thr Arg Gly Asn Pro
                     85                  90                  95

Thr Asn Pro Lys Glu Ser Lys Lys Glu Val Ala Ser Lys Thr Glu Thr
                100                 105                 110

Asn Gln Cys Asp
        115
```

<210> SEQ ID NO 64
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 64

```
Met Asp Val Gly Glu Val Ala Ser Asp Lys Lys Glu Glu Asp Ile Thr
 1               5                  10                  15

His Phe Asp Pro Phe Arg Ala Arg Thr Thr Pro Arg Lys Thr Ala Cys
                20                  25                  30

Thr Thr Cys Tyr Cys Lys Lys Cys Cys Phe His Cys Gln Val Cys Phe
            35                  40                  45

Thr Arg Lys Gly Leu Gly Ile Ser Tyr Gly Arg Lys Lys Arg Arg Gln
        50                  55                  60

Arg Arg Arg Ala Pro Gln Asp Ser Gln Thr His Gln Ala Ser Leu Ser
 65                  70                  75                  80

Lys Gln Pro Ala Ser Gln Ser Arg Gly Asp Pro Thr Gly Pro Thr Glu
                85                  90                  95

Ser Lys Lys Lys Val Glu Arg Glu Thr Glu Thr Asp Pro Phe Asp
                100                 105                 110
```

<210> SEQ ID NO 65
<211> LENGTH: 123
<212> TYPE: PRT
<213> ORGANISM: Artificial Sequence
<220> FEATURE:
<223> OTHER INFORMATION: Tat derivative polypeptide

<400> SEQUENCE: 65

```
Met Asp Val Gly Glu Val Ala Ser Asp Lys Lys Glu Glu Asp Ile Thr
 1               5                  10                  15

His Phe Asp Pro Phe Arg Ala Arg Thr Thr Pro Arg Thr Ala Cys Asn
                20                  25                  30

Asn Cys Tyr Cys Lys Lys Cys Cys Phe His Cys Tyr Ala Cys Phe Leu
            35                  40                  45

Arg Lys Gly Leu Gly Ile Thr Tyr His Ala Phe Arg Thr Arg Arg Lys
        50                  55                  60

Lys Ile Ala Ser Ala Asp Arg Ile Pro Val Pro Gln Gln Ser Ile Ser
 65                  70                  75                  80

Ile Arg Gly Arg Asp Ser Gln Thr Thr Gln Glu Ser Gln Lys Lys Val
                85                  90                  95

Glu Glu Gln Ala Lys Ala Asn Leu Arg Ile Ser Arg Lys Asn Leu Gly
                100                 105                 110

Asp Glu Thr Arg Gly Pro Val Gly Ala Gly Asn
        115                 120
```

<210> SEQ ID NO 66
<211> LENGTH: 117
<212> TYPE: PRT
<213> ORGANISM: Artificial Sequence
<220> FEATURE:
<223> OTHER INFORMATION: Tat derivative polypeptide

<400> SEQUENCE: 66

```
Met Asp Val Gly Glu Val Ala Ser Asp Lys Lys Glu Glu Asp Ile Thr
1               5                   10                  15

His Phe Asp Pro Phe Arg Ala Arg Thr Thr Pro Leu Glu Thr Cys Asn
            20                  25                  30

Asn Thr Cys Tyr Cys Lys Glu Cys Cys Tyr His Cys Gln Leu Cys Phe
        35                  40                  45

Leu Asn Lys Gly Leu Gly Ile Trp Tyr Asp Arg Lys Gly Arg Arg Arg
    50                  55                  60

Arg Ser Pro Lys Lys Ile Lys Ala His Ser Ser Ser Ala Ser Asp Lys
65                  70                  75                  80

Ser Ile Ser Thr Arg Thr Arg Asn Ser Gln Pro Glu Lys Gln Lys
                85                  90                  95

Lys Thr Leu Glu Thr Thr Leu Gly Thr Asp Cys Gly Pro Gly Arg Ser
            100                 105                 110

His Ile Tyr Ile Ser
        115
```

<210> SEQ ID NO 67
<211> LENGTH: 110
<212> TYPE: PRT
<213> ORGANISM: Artificial Sequence
<220> FEATURE:
<223> OTHER INFORMATION: Tat derivative polypeptide

<400> SEQUENCE: 67

```
Met Asp Val Gly Glu Val Ala Ser Asp Lys Lys Glu Glu Asp Ile Thr
1               5                   10                  15

His Phe Asp Pro Phe Arg Ala Arg Thr Thr Pro Thr Thr Ala Cys Ser
            20                  25                  30

Lys Cys Tyr Cys Lys Met Cys Cys Trp His Cys Gln Leu Cys Phe Leu
        35                  40                  45

Asn Lys Gly Leu Gly Ile Ser Tyr Gly Arg Lys Lys Arg Lys Arg Arg
    50                  55                  60

Arg Gly Thr Pro Gln Ser Arg Gln Asp His Gln Asn Pro Val Pro Lys
65                  70                  75                  80

Gln Pro Leu Pro Thr Thr Arg Gly Asn Pro Thr Asn Pro Lys Glu Ser
                85                  90                  95

Lys Lys Glu Val Ala Ser Lys Thr Glu Thr Asn Gln Cys Asp
            100                 105                 110
```

<210> SEQ ID NO 68
<211> LENGTH: 103
<212> TYPE: PRT
<213> ORGANISM: Artificial Sequence
<220> FEATURE:
<223> OTHER INFORMATION: Tat derivative polypeptide

<400> SEQUENCE: 68

```
Met Asp Ala Arg Lys Val Asp Leu Asp Gln Gln Asp Ala Gly Thr His
1               5                   10                  15

Phe Glu Pro Arg Lys Thr Ala Cys Thr Thr Cys Tyr Cys Lys Lys Cys
```

```
                    20                  25                  30

Cys Phe His Cys Gln Val Cys Phe Thr Arg Lys Gly Leu Gly Ile Ser
            35                  40                  45

Tyr Gly Arg Lys Lys Arg Gln Arg Arg Ala Pro Gln Asp Ser
        50                  55                  60

Gln Thr His Gln Ala Ser Leu Ser Lys Gln Pro Ala Ser Gln Ser Arg
65                  70                  75                  80

Gly Asp Pro Thr Gly Pro Thr Glu Ser Lys Lys Val Glu Arg Glu
                85                  90                  95

Thr Glu Thr Asp Pro Phe Asp
                100

<210> SEQ ID NO 69
<211> LENGTH: 115
<212> TYPE: PRT
<213> ORGANISM: Artificial Sequence
<220> FEATURE:
<223> OTHER INFORMATION: Tat derivative polypeptide

<400> SEQUENCE: 69

Met Asp Ala Arg Lys Val Asp Leu Asp Gln Gln Asp Ala Gly Thr His
1               5                   10                  15

Phe Glu Pro Arg Thr Ala Cys Asn Asn Cys Tyr Cys Lys Lys Cys Cys
                20                  25                  30

Phe His Cys Tyr Ala Cys Phe Leu Arg Lys Gly Leu Gly Ile Thr Tyr
            35                  40                  45

His Ala Phe Arg Thr Arg Lys Lys Ile Ala Ser Ala Asp Arg Ile
        50                  55                  60

Pro Val Pro Gln Gln Ser Ile Ser Ile Arg Gly Arg Asp Ser Gln Thr
65                  70                  75                  80

Thr Gln Glu Ser Gln Lys Lys Val Glu Glu Gln Ala Lys Ala Asn Leu
                85                  90                  95

Arg Ile Ser Arg Lys Asn Leu Gly Asp Glu Thr Arg Gly Pro Val Gly
                100                 105                 110

Ala Gly Asn
        115

<210> SEQ ID NO 70
<211> LENGTH: 109
<212> TYPE: PRT
<213> ORGANISM: Artificial Sequence
<220> FEATURE:
<223> OTHER INFORMATION: Tat derivative polypeptide

<400> SEQUENCE: 70

Met Asp Ala Arg Lys Val Asp Leu Asp Gln Gln Asp Ala Gly Thr His
1               5                   10                  15

Phe Glu Pro Leu Glu Thr Cys Asn Asn Thr Cys Tyr Cys Lys Glu Cys
                20                  25                  30

Cys Tyr His Cys Gln Leu Cys Phe Leu Asn Lys Gly Leu Gly Ile Trp
            35                  40                  45

Tyr Asp Arg Lys Gly Arg Arg Arg Ser Pro Lys Lys Ile Lys Ala
        50                  55                  60

His Ser Ser Ser Ala Ser Asp Lys Ser Ile Ser Thr Arg Thr Arg Asn
65                  70                  75                  80

Ser Gln Pro Glu Glu Lys Gln Lys Lys Thr Leu Glu Thr Thr Leu Gly
                85                  90                  95
```

```
Thr Asp Cys Gly Pro Gly Arg Ser His Ile Tyr Ile Ser
            100                 105
```

<210> SEQ ID NO 71
<211> LENGTH: 102
<212> TYPE: PRT
<213> ORGANISM: Artificial Sequence
<220> FEATURE:
<223> OTHER INFORMATION: Tat derivative polypeptide

<400> SEQUENCE: 71

```
Met Asp Ala Arg Lys Val Asp Leu Asp Gln Gln Asp Ala Gly Thr His
1               5                   10                  15

Phe Glu Pro Thr Thr Ala Cys Ser Lys Cys Tyr Cys Lys Met Cys Cys
            20                  25                  30

Trp His Cys Gln Leu Cys Phe Leu Asn Lys Gly Leu Gly Ile Ser Tyr
        35                  40                  45

Gly Arg Lys Lys Arg Lys Arg Arg Gly Thr Pro Gln Ser Arg Gln
    50                  55                  60

Asp His Gln Asn Pro Val Pro Lys Gln Pro Leu Pro Thr Thr Arg Gly
65                  70                  75                  80

Asn Pro Thr Asn Pro Lys Glu Ser Lys Lys Glu Val Ala Ser Lys Thr
                85                  90                  95

Glu Thr Asn Gln Cys Asp
            100
```

<210> SEQ ID NO 72
<211> LENGTH: 107
<212> TYPE: PRT
<213> ORGANISM: Artificial Sequence
<220> FEATURE:
<223> OTHER INFORMATION: Tat derivative polypeptide

<400> SEQUENCE: 72

```
Met Ser Ser Lys Glu Glu Leu Arg Thr Thr Pro Ile Ser Asp Pro Phe
1               5                   10                  15

Gln Glu Glu Gly Arg Gly Pro Arg Lys Thr Ala Cys Thr Thr Cys Tyr
            20                  25                  30

Cys Lys Lys Cys Cys Phe His Cys Gln Val Cys Phe Thr Arg Lys Gly
        35                  40                  45

Leu Gly Ile Ser Tyr Gly Arg Lys Lys Arg Arg Gln Arg Arg Ala
    50                  55                  60

Pro Gln Asp Ser Gln Thr His Gln Ala Ser Leu Ser Lys Gln Pro Ala
65                  70                  75                  80

Ser Gln Ser Arg Gly Asp Pro Thr Gly Pro Thr Glu Ser Lys Lys Lys
                85                  90                  95

Val Glu Arg Glu Thr Glu Thr Asp Pro Phe Asp
            100                 105
```

<210> SEQ ID NO 73
<211> LENGTH: 119
<212> TYPE: PRT
<213> ORGANISM: Artificial Sequence
<220> FEATURE:
<223> OTHER INFORMATION: Tat derivative polypeptide

<400> SEQUENCE: 73

```
Met Ser Ser Lys Glu Glu Leu Arg Thr Thr Pro Ile Ser Asp Pro Phe
1               5                   10                  15

Gln Glu Glu Gly Arg Gly Pro Arg Thr Ala Cys Asn Asn Cys Tyr Cys
```

```
                    20                  25                  30

Lys Lys Cys Cys Phe His Cys Tyr Ala Cys Phe Leu Arg Lys Gly Leu
            35                  40                  45

Gly Ile Thr Tyr His Ala Phe Arg Thr Arg Arg Lys Lys Ile Ala Ser
        50                  55                  60

Ala Asp Arg Ile Pro Val Pro Gln Gln Ser Ile Ser Ile Arg Gly Arg
65                  70                  75                  80

Asp Ser Gln Thr Thr Gln Glu Ser Gln Lys Lys Val Glu Gln Ala
                85                  90                  95

Lys Ala Asn Leu Arg Ile Ser Arg Lys Asn Leu Gly Asp Glu Thr Arg
                100                 105                 110

Gly Pro Val Gly Ala Gly Asn
            115

<210> SEQ ID NO 74
<211> LENGTH: 113
<212> TYPE: PRT
<213> ORGANISM: Artificial Sequence
<220> FEATURE:
<223> OTHER INFORMATION: Tat derivative polypeptide

<400> SEQUENCE: 74

Met Ser Ser Lys Glu Glu Leu Arg Thr Thr Pro Ile Ser Asp Pro Phe
1               5                   10                  15

Gln Glu Glu Gly Arg Gly Pro Leu Glu Thr Cys Asn Asn Thr Cys Tyr
                20                  25                  30

Cys Lys Glu Cys Cys Tyr His Cys Gln Leu Cys Phe Leu Asn Lys Gly
            35                  40                  45

Leu Gly Ile Trp Tyr Asp Arg Lys Gly Arg Arg Arg Ser Pro Lys
    50                  55                  60

Lys Ile Lys Ala His Ser Ser Ala Ser Asp Lys Ser Ile Ser Thr
65                  70                  75                  80

Arg Thr Arg Asn Ser Gln Pro Glu Glu Lys Lys Lys Thr Leu Glu
                85                  90                  95

Thr Thr Leu Gly Thr Asp Cys Gly Pro Gly Arg Ser His Ile Tyr Ile
                100                 105                 110

Ser

<210> SEQ ID NO 75
<211> LENGTH: 106
<212> TYPE: PRT
<213> ORGANISM: Artificial Sequence
<220> FEATURE:
<223> OTHER INFORMATION: Tat derivative polypeptide

<400> SEQUENCE: 75

Met Ser Ser Lys Glu Glu Leu Arg Thr Thr Pro Ile Ser Asp Pro Phe
1               5                   10                  15

Gln Glu Glu Gly Arg Gly Pro Thr Thr Ala Cys Ser Lys Cys Tyr Cys
                20                  25                  30

Lys Met Cys Cys Trp His Cys Gln Leu Cys Phe Leu Asn Lys Gly Leu
            35                  40                  45

Gly Ile Ser Tyr Gly Arg Lys Lys Arg Lys Arg Arg Gly Thr Pro
    50                  55                  60

Gln Ser Arg Gln Asp His Gln Asn Pro Val Pro Lys Gln Pro Leu Pro
65                  70                  75                  80

Thr Thr Arg Gly Asn Pro Thr Asn Pro Lys Glu Ser Lys Lys Glu Val
```

```
                    85                  90                  95

Ala Ser Lys Thr Glu Thr Asn Gln Cys Asp
            100                 105

<210> SEQ ID NO 76
<211> LENGTH: 105
<212> TYPE: PRT
<213> ORGANISM: Artificial Sequence
<220> FEATURE:
<223> OTHER INFORMATION: Tat derivative polypeptide

<400> SEQUENCE: 76

Met Asp Pro Ser Val Glu Glu Leu Pro Lys Glu Gln Arg Pro Gly Ala
1               5                   10                  15

Ala Pro Ala Thr Pro Arg Lys Thr Ala Cys Thr Thr Cys Tyr Cys Lys
            20                  25                  30

Lys Cys Cys Phe His Cys Gln Val Cys Phe Thr Arg Lys Gly Leu Gly
        35                  40                  45

Ile Ser Tyr Gly Arg Lys Lys Arg Arg Gln Arg Arg Ala Pro Gln
    50                  55                  60

Asp Ser Gln Thr His Gln Ala Ser Leu Ser Lys Gln Pro Ala Ser Gln
65                  70                  75                  80

Ser Arg Gly Asp Pro Thr Gly Pro Thr Glu Ser Lys Lys Val Glu
                85                  90                  95

Arg Glu Thr Glu Thr Asp Pro Phe Asp
            100                 105

<210> SEQ ID NO 77
<211> LENGTH: 117
<212> TYPE: PRT
<213> ORGANISM: Artificial Sequence
<220> FEATURE:
<223> OTHER INFORMATION: Tat derivative polypeptide

<400> SEQUENCE: 77

Met Asp Pro Ser Val Glu Glu Leu Pro Lys Glu Gln Arg Pro Gly Ala
1               5                   10                  15

Ala Pro Ala Thr Pro Arg Thr Ala Cys Asn Asn Cys Tyr Cys Lys Lys
            20                  25                  30

Cys Cys Phe His Cys Tyr Ala Cys Phe Leu Arg Lys Gly Leu Gly Ile
        35                  40                  45

Thr Tyr His Ala Phe Arg Thr Arg Lys Lys Ile Ala Ser Ala Asp
    50                  55                  60

Arg Ile Pro Val Pro Gln Ser Ile Ser Ile Arg Gly Arg Asp Ser
65                  70                  75                  80

Gln Thr Thr Gln Glu Ser Gln Lys Lys Val Glu Glu Gln Ala Lys Ala
                85                  90                  95

Asn Leu Arg Ile Ser Arg Lys Asn Leu Gly Asp Glu Thr Arg Gly Pro
            100                 105                 110

Val Gly Ala Gly Asn
        115

<210> SEQ ID NO 78
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 78
```

Met Asp Pro Ser Val Glu Glu Leu Pro Lys Glu Gln Arg Pro Gly Ala
1               5                   10                  15

Ala Pro Ala Thr Pro Leu Glu Thr Cys Asn Asn Thr Cys Tyr Cys Lys
            20                  25                  30

Glu Cys Cys Tyr His Cys Gln Leu Cys Phe Leu Asn Lys Gly Leu Gly
        35                  40                  45

Ile Trp Tyr Asp Arg Lys Gly Arg Arg Arg Ser Pro Lys Lys Ile
    50                  55                  60

Lys Ala His Ser Ser Ser Ala Ser Asp Lys Ser Ile Ser Thr Arg Thr
65              70                  75                  80

Arg Asn Ser Gln Pro Glu Glu Lys Gln Lys Thr Leu Glu Thr Thr
            85                  90                  95

Leu Gly Thr Asp Cys Gly Pro Gly Arg Ser His Ile Tyr Ile Ser
            100                 105                 110

<210> SEQ ID NO 79
<211> LENGTH: 104
<212> TYPE: PRT
<213> ORGANISM: Artificial Sequence
<220> FEATURE:
<223> OTHER INFORMATION: Tat derivative polypeptide

<400> SEQUENCE: 79

Met Asp Pro Ser Val Glu Glu Leu Pro Lys Glu Gln Arg Pro Gly Ala
1               5                   10                  15

Ala Pro Ala Thr Pro Thr Thr Ala Cys Ser Lys Cys Tyr Cys Lys Met
            20                  25                  30

Cys Cys Trp His Cys Gln Leu Cys Phe Leu Asn Lys Gly Leu Gly Ile
        35                  40                  45

Ser Tyr Gly Arg Lys Lys Arg Lys Arg Arg Gly Thr Pro Gln Ser
    50                  55                  60

Arg Gln Asp His Gln Asn Pro Val Pro Lys Gln Pro Leu Pro Thr Thr
65              70                  75                  80

Arg Gly Asn Pro Thr Asn Pro Lys Glu Ser Lys Lys Glu Val Ala Ser
            85                  90                  95

Lys Thr Glu Thr Asn Gln Cys Asp
            100

<210> SEQ ID NO 80
<211> LENGTH: 103
<212> TYPE: PRT
<213> ORGANISM: Artificial Sequence
<220> FEATURE:
<223> OTHER INFORMATION: Tat derivative polypeptide

<400> SEQUENCE: 80

Met Glu Glu Glu Met Asp Leu Phe Gln Gly Arg Gly Arg Gly Glu Ala
1               5                   10                  15

Asn His Pro Arg Lys Thr Ala Cys Thr Thr Cys Tyr Cys Lys Lys Cys
            20                  25                  30

Cys Phe His Cys Gln Val Cys Phe Thr Arg Lys Gly Leu Gly Ile Ser
        35                  40                  45

Tyr Gly Arg Lys Lys Arg Arg Gln Arg Arg Ala Pro Gln Asp Ser
    50                  55                  60

Gln Thr His Gln Ala Ser Leu Ser Lys Gln Pro Ala Ser Gln Ser Arg
65              70                  75                  80

Gly Asp Pro Thr Gly Pro Thr Glu Ser Lys Lys Lys Val Glu Arg Glu

Thr Glu Thr Asp Pro Phe Asp
            100

<210> SEQ ID NO 81
<211> LENGTH: 115
<212> TYPE: PRT
<213> ORGANISM: Artificial Sequence
<220> FEATURE:
<223> OTHER INFORMATION: Tat derivative polypeptide

<400> SEQUENCE: 81

Met Glu Glu Met Asp Leu Phe Gln Gly Arg Gly Arg Gly Glu Ala
1               5                   10                  15

Asn His Pro Arg Thr Ala Cys Asn Asn Cys Tyr Cys Lys Lys Cys
                20                  25                  30

Phe His Cys Tyr Ala Cys Phe Leu Arg Lys Gly Leu Gly Ile Thr Tyr
                35                  40                  45

His Ala Phe Arg Thr Arg Arg Lys Lys Ile Ala Ser Ala Asp Arg Ile
        50                  55                  60

Pro Val Pro Gln Gln Ser Ile Ser Ile Arg Gly Arg Asp Ser Gln Thr
65                  70                  75                  80

Thr Gln Glu Ser Gln Lys Lys Val Glu Glu Gln Ala Lys Ala Asn Leu
                85                  90                  95

Arg Ile Ser Arg Lys Asn Leu Gly Asp Glu Thr Arg Gly Pro Val Gly
                100                 105                 110

Ala Gly Asn
        115

<210> SEQ ID NO 82
<211> LENGTH: 109
<212> TYPE: PRT
<213> ORGANISM: Artificial Sequence
<220> FEATURE:
<223> OTHER INFORMATION: Tat derivative polypeptide

<400> SEQUENCE: 82

Met Glu Glu Met Asp Leu Phe Gln Gly Arg Gly Arg Gly Glu Ala
1               5                   10                  15

Asn His Pro Leu Glu Thr Cys Asn Asn Thr Cys Tyr Cys Lys Glu Cys
                20                  25                  30

Cys Tyr His Cys Gln Leu Cys Phe Leu Asn Lys Gly Leu Gly Ile Trp
        35                  40                  45

Tyr Asp Arg Lys Gly Arg Arg Arg Ser Pro Lys Lys Ile Lys Ala
        50                  55                  60

His Ser Ser Ser Ala Ser Asp Lys Ser Ile Ser Thr Arg Thr Arg Asn
65                  70                  75                  80

Ser Gln Pro Glu Glu Lys Gln Lys Thr Leu Glu Thr Thr Leu Gly
                85                  90                  95

Thr Asp Cys Gly Pro Gly Arg Ser His Ile Tyr Ile Ser
        100                 105

<210> SEQ ID NO 83
<211> LENGTH: 102
<212> TYPE: PRT
<213> ORGANISM: Artificial Sequence
<220> FEATURE:
<223> OTHER INFORMATION: Tat derivative polypeptide

<400> SEQUENCE: 83

```
Met Glu Glu Met Asp Leu Phe Gln Gly Arg Gly Arg Gly Glu Ala
1               5                   10                  15

Asn His Pro Thr Thr Ala Cys Ser Lys Cys Tyr Cys Lys Met Cys Cys
            20                  25                  30

Trp His Cys Gln Leu Cys Phe Leu Asn Lys Gly Leu Gly Ile Ser Tyr
            35                  40                  45

Gly Arg Lys Lys Arg Lys Arg Arg Gly Thr Pro Gln Ser Arg Gln
    50                  55                  60

Asp His Gln Asn Pro Val Pro Lys Gln Pro Leu Pro Thr Thr Arg Gly
65              70                  75                  80

Asn Pro Thr Asn Pro Lys Glu Ser Lys Lys Glu Val Ala Ser Lys Thr
                85                  90                  95

Glu Thr Asn Gln Cys Asp
                100
```

<210> SEQ ID NO 84
<211> LENGTH: 99
<212> TYPE: PRT
<213> ORGANISM: Artificial Sequence
<220> FEATURE:
<223> OTHER INFORMATION: Tat derivative polypeptide

<400> SEQUENCE: 84

```
Met Asn Ala Asp Ser Ile Asp Pro Phe Ala Gly Asn Lys Thr Pro Arg
1               5                   10                  15

Lys Thr Ala Cys Thr Thr Cys Tyr Cys Lys Lys Cys Cys Phe His Cys
            20                  25                  30

Gln Val Cys Phe Thr Arg Lys Gly Leu Gly Ile Ser Tyr Gly Arg Lys
            35                  40                  45

Lys Arg Arg Gln Arg Arg Arg Ala Pro Gln Asp Ser Gln Thr His Gln
    50                  55                  60

Ala Ser Leu Ser Lys Gln Pro Ala Ser Gln Ser Arg Gly Asp Pro Thr
65              70                  75                  80

Gly Pro Thr Glu Ser Lys Lys Lys Val Glu Arg Glu Thr Glu Thr Asp
                85                  90                  95

Pro Phe Asp
```

<210> SEQ ID NO 85
<211> LENGTH: 111
<212> TYPE: PRT
<213> ORGANISM: Artificial Sequence
<220> FEATURE:
<223> OTHER INFORMATION: Tat derivative polypeptide

<400> SEQUENCE: 85

```
Met Asn Ala Asp Ser Ile Asp Pro Phe Ala Gly Asn Lys Thr Pro Arg
1               5                   10                  15

Thr Ala Cys Asn Asn Cys Tyr Cys Lys Lys Cys Cys Phe His Cys Tyr
            20                  25                  30

Ala Cys Phe Leu Arg Lys Gly Leu Gly Ile Thr Tyr His Ala Phe Arg
            35                  40                  45

Thr Arg Arg Lys Lys Ile Ala Ser Ala Asp Arg Ile Pro Val Pro Gln
    50                  55                  60

Gln Ser Ile Ser Ile Arg Gly Arg Asp Ser Gln Thr Thr Gln Glu Ser
65              70                  75                  80

Gln Lys Lys Val Glu Glu Gln Ala Lys Ala Asn Leu Arg Ile Ser Arg
                85                  90                  95
```

```
Lys Asn Leu Gly Asp Glu Thr Arg Gly Pro Val Gly Ala Gly Asn
            100                 105                 110
```

<210> SEQ ID NO 86
<211> LENGTH: 105
<212> TYPE: PRT
<213> ORGANISM: Artificial Sequence
<220> FEATURE:
<223> OTHER INFORMATION: Tat derivative polypeptide

<400> SEQUENCE: 86

```
Met Asn Ala Asp Ser Ile Asp Pro Phe Ala Gly Asn Lys Thr Pro Leu
1               5                   10                  15

Glu Thr Cys Asn Asn Thr Cys Tyr Cys Lys Glu Cys Cys Tyr His Cys
            20                  25                  30

Gln Leu Cys Phe Leu Asn Lys Gly Leu Gly Ile Trp Tyr Asp Arg Lys
        35                  40                  45

Gly Arg Arg Arg Arg Ser Pro Lys Lys Ile Lys Ala His Ser Ser
    50                  55                  60

Ala Ser Asp Lys Ser Ile Ser Thr Arg Thr Arg Asn Ser Gln Pro Glu
65                  70                  75                  80

Glu Lys Gln Lys Lys Thr Leu Glu Thr Thr Leu Gly Thr Asp Cys Gly
                85                  90                  95

Pro Gly Arg Ser His Ile Tyr Ile Ser
            100                 105
```

<210> SEQ ID NO 87
<211> LENGTH: 98
<212> TYPE: PRT
<213> ORGANISM: Artificial Sequence
<220> FEATURE:
<223> OTHER INFORMATION: Tat derivative polypeptide

<400> SEQUENCE: 87

```
Met Asn Ala Asp Ser Ile Asp Pro Phe Ala Gly Asn Lys Thr Pro Thr
1               5                   10                  15

Thr Ala Cys Ser Lys Cys Tyr Cys Lys Met Cys Cys Trp His Cys Gln
            20                  25                  30

Leu Cys Phe Leu Asn Lys Gly Leu Gly Ile Ser Tyr Gly Arg Lys Lys
        35                  40                  45

Arg Lys Arg Arg Arg Gly Thr Pro Gln Ser Arg Gln Asp His Gln Asn
    50                  55                  60

Pro Val Pro Lys Gln Pro Leu Pro Thr Thr Arg Gly Asn Pro Thr Asn
65                  70                  75                  80

Pro Lys Glu Ser Lys Lys Glu Val Ala Ser Lys Thr Glu Thr Asn Gln
                85                  90                  95

Cys Asp
```

<210> SEQ ID NO 88
<211> LENGTH: 104
<212> TYPE: PRT
<213> ORGANISM: Artificial Sequence
<220> FEATURE:
<223> OTHER INFORMATION: Tat derivative polypeptide

<400> SEQUENCE: 88

```
Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
```

```
                20              25              30
Lys Lys Cys Cys Phe His Cys Tyr Ala Cys Phe Leu Arg Lys Gly Leu
            35              40              45
Phe Leu Gln Lys Gly Leu Gly Ile Ser Tyr Arg Ser Tyr Ser Lys Lys
        50              55              60
Thr Lys Pro Asp Thr Thr Ala Ala Ser Arg Asx Leu Gly Arg Val
65              70              75              80
Thr Leu Ser Leu Tyr Leu Ser Arg Thr Thr Ser Thr Thr Trp Lys Arg
            85              90              95
Asp Ser Lys Thr Ala Lys Lys Glu
            100
```

<210> SEQ ID NO 89
<211> LENGTH: 130
<212> TYPE: PRT
<213> ORGANISM: Artificial Sequence
<220> FEATURE:
<223> OTHER INFORMATION: Tat derivative polypeptide

<400> SEQUENCE: 89

```
Met Asp Pro Lys Gly Glu Glu Asp Gln Asp Val Ser His Gln Asp Leu
1               5                   10                  15
Ile Lys Gln Tyr Arg Lys Pro Ala Cys Tyr Cys Arg Ile Pro Ala Cys
                20              25              30
Ile Ala Gly Glu Arg Arg Tyr Gly Thr Cys Ile Tyr Gln Gly Arg Leu
            35              40              45
Trp Ala Phe Cys Cys Phe Leu Arg Lys Gly Leu Gly Ile Thr Tyr His
        50              55              60
Ala Phe Arg Thr Arg Arg Lys Lys Ile Ala Ser Ala Asp Arg Ile Pro
65              70              75              80
Val Pro Gln Gln Ser Ile Ser Ile Arg Gly Arg Asp Ser Gln Thr Thr
            85              90              95
Gln Glu Ser Gln Lys Lys Val Glu Glu Gln Ala Lys Ala Asn Leu Arg
            100             105             110
Ile Ser Arg Lys Asn Leu Gly Asp Glu Thr Arg Gly Pro Val Gly Ala
            115             120             125
Gly Asn
    130
```

<210> SEQ ID NO 90
<211> LENGTH: 132
<212> TYPE: PRT
<213> ORGANISM: Artificial Sequence
<220> FEATURE:
<223> OTHER INFORMATION: Tat derivative polypeptide

<400> SEQUENCE: 90

```
Met Asp Pro Lys Gly Glu Glu Asp Gln Asp Val Ser His Gln Asp Leu
1               5                   10                  15
Ile Lys Gln Tyr Arg Lys Pro Thr Cys Leu Lys Ser Gly Ala Ile Cys
                20              25              30
His Pro Val Phe Cys Pro Arg Arg Tyr Lys Gln Ile Gly Thr Cys Gly
            35              40              45
Leu Pro Gly Thr Lys Cys Cys Phe Leu Arg Lys Gly Leu Gly Ile Thr
        50              55              60
Tyr His Ala Phe Arg Thr Arg Arg Lys Lys Ile Ala Ser Ala Asp Arg
65              70              75              80
```

Ile Pro Val Pro Gln Gln Ser Ile Ser Ile Arg Gly Arg Asp Ser Gln
                85                  90                  95

Thr Thr Gln Glu Ser Gln Lys Lys Val Glu Glu Gln Ala Lys Ala Asn
            100                 105                 110

Leu Arg Ile Ser Arg Lys Asn Leu Gly Asp Glu Thr Arg Gly Pro Val
        115                 120                 125

Gly Ala Gly Asn
    130

<210> SEQ ID NO 91
<211> LENGTH: 87
<212> TYPE: PRT
<213> ORGANISM: Artificial Sequence
<220> FEATURE:
<223> OTHER INFORMATION: Tat derivative polypeptide

<400> SEQUENCE: 91

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Thr Lys Lys Gly Leu
        35                  40                  45

Gly Ile Ser Tyr Gly Arg Lys Lys Arg Arg Pro Ala Arg Thr Ala
    50                  55                  60

Asp Lys Asp Gln Asp Asn Gln Asp Pro Val Ser Lys Gln Ser Leu Ala
65                  70                  75                  80

Gly Thr Arg Ser Gln Gln Glu
                85

<210> SEQ ID NO 92
<211> LENGTH: 141
<212> TYPE: PRT
<213> ORGANISM: Artificial Sequence
<220> FEATURE:
<223> OTHER INFORMATION: Tat derivative polypeptide

<400> SEQUENCE: 92

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Thr Lys Lys Ala Leu
        35                  40                  45

Gly Ile Ser Tyr Gly Arg Lys Arg Arg Gly Arg Lys Ser Ala Gly Asp
    50                  55                  60

Asn Lys Thr His Gln Asp Pro Val Arg Gln Ser Leu Pro Lys Arg
65                  70                  75                  80

Ser Arg Ile Gln Ser Ser Gln Glu Glu Ser Gln Lys Glu Val Glu Thr
                85                  90                  95

Glu Ala Gly Ser Gly Gly Arg Pro Arg Pro Glu Asp Ser Ser Ala Ser
            100                 105                 110

Ser Gly Arg Thr Ser Gly Thr Ser Ser Gly Ser Thr Arg Pro Val
        115                 120                 125

Ser Thr Ser Ser Gly Cys Trp Gly Pro Tyr Ser Lys Pro
    130                 135                 140

<210> SEQ ID NO 93

```
<211> LENGTH: 117
<212> TYPE: PRT
<213> ORGANISM: Artificial Sequence
<220> FEATURE:
<223> OTHER INFORMATION: Tat derivative polypeptide

<400> SEQUENCE: 93

Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Leu Thr Lys Gly Leu
        35                  40                  45

Gly Ile Ser Tyr Gly Arg Lys Arg Lys Arg Arg Arg Ala Thr Ser Pro
    50                  55                  60

Val Pro Gly Leu Ser Ser Lys Asn Pro Ala Arg Lys Gln Gly Arg
65                  70                  75                  80

Asp Thr Leu Phe Phe Leu Leu Arg Ser Leu Ser His Pro Thr Arg Asp
                85                  90                  95

Ser Gln Arg Pro Thr Glu Gln Ala Gln Ala Val Ala Thr Ala Ala Thr
            100                 105                 110

Pro Asp Arg Gln His
        115

<210> SEQ ID NO 94
<211> LENGTH: 136
<212> TYPE: PRT
<213> ORGANISM: Artificial Sequence
<220> FEATURE:
<223> OTHER INFORMATION: Tat derivative polypeptide

<400> SEQUENCE: 94

Met Glu Thr Pro Leu Arg Glu Gln Glu Asn Ser Leu Lys Ser Ser Asn
1               5                   10                  15

Gly Arg Ser Ser Cys Thr Ser Glu Ala Ala Pro Thr Leu Glu Ser
            20                  25                  30

Ala Asn Leu Glu Glu Glu Ile Leu Ser Gln Leu Tyr Arg Pro Leu Glu
        35                  40                  45

Thr Cys Asn Asn Thr Cys Tyr Cys Lys Glu Cys Cys Tyr His Cys Gln
    50                  55                  60

Leu Cys Phe Leu Asn Lys Gly Leu Gly Ile Trp Tyr Asp Arg Lys Gly
65                  70                  75                  80

Arg Arg Arg Arg Ser Pro Lys Lys Ile Lys Ala His Ser Ser Ser Ala
                85                  90                  95

Ser Asp Lys Ser Ile Ser Thr Arg Thr Arg Asn Ser Gln Pro Glu Glu
            100                 105                 110

Lys Gln Lys Lys Thr Leu Glu Thr Thr Leu Gly Thr Asp Cys Gly Pro
        115                 120                 125

Gly Arg Ser His Ile Tyr Ile Ser
    130                 135

<210> SEQ ID NO 95
<211> LENGTH: 108
<212> TYPE: PRT
<213> ORGANISM: Artificial Sequence
<220> FEATURE:
<223> OTHER INFORMATION: Tat derivative polypeptide

<400> SEQUENCE: 95
```

```
Met Asp Pro Lys Gly Glu Glu Asp Gln Asp Val Ser His Gln Asp Leu
1               5                   10                  15

Ile Lys Gln Tyr Arg Lys Pro Arg Thr Ala Cys Asn Asn Cys Tyr Cys
            20                  25                  30

Lys Lys Cys Cys Phe His Cys Tyr Ala Cys Phe Phe Met Lys Lys Gly
            35                  40                  45

Leu Gly Ile Ser Tyr Gly Arg Lys Arg Arg Gln Arg Arg Gly Ala
        50                  55                  60

Ser Lys Ser Asn Gln Asn His Gln Asp Ser Ile Pro Glu Gln Pro Phe
65                  70                  75                  80

Ser Gln Ser Arg Gly Asp Gln Ser Ser Pro Glu Lys Gln Glu Lys Lys
                85                  90                  95

Val Glu Ser Lys Thr Thr Ser Asp Pro Phe Gly Cys
                100                 105
```

<210> SEQ ID NO 96
<211> LENGTH: 18
<212> TYPE: PRT
<213> ORGANISM: Human immunodeficiency virus type 1

<400> SEQUENCE: 96

```
Met Glu Pro Val Asp Ala Asn Leu Glu Ala Trp Lys His Ala Gly Ser
1               5                   10                  15

Gln Pro
```

<210> SEQ ID NO 97
<211> LENGTH: 23
<212> TYPE: PRT
<213> ORGANISM: Simian immunodeficiency virus

<400> SEQUENCE: 97

```
Met Asp Pro Lys Gly Glu Glu Asp Gln Asp Val Ser His Gln Asp Leu
1               5                   10                  15

Ile Lys Gln Tyr Arg Lys Pro
            20
```

<210> SEQ ID NO 98
<211> LENGTH: 28
<212> TYPE: PRT
<213> ORGANISM: Simian immunodeficiency virus

<400> SEQUENCE: 98

```
Met Glu Thr Pro Leu Lys Glu Gln Glu Asn Ser Leu Glu Ser Cys Arg
1               5                   10                  15

Glu His Ser Ser Ser Ile Ser Glu Val Asp Val Pro
            20                  25
```

<210> SEQ ID NO 99
<211> LENGTH: 46
<212> TYPE: PRT
<213> ORGANISM: Simian immunodeficiency virus

<400> SEQUENCE: 99

```
Met Glu Thr Pro Leu Lys Glu Gln Glu Ser Ser Leu Glu Ser Ser Arg
1               5                   10                  15

Glu His Ser Ser Ser Ile Ser Glu Val Asp Ala Asp Thr Pro Glu Ser
            20                  25                  30

Ala Ser Leu Glu Glu Glu Ile Leu Ser Gln Leu Tyr Arg Pro
        35                  40                  45
```

<210> SEQ ID NO 100
<211> LENGTH: 27
<212> TYPE: PRT
<213> ORGANISM: Simian immunodeficiency virus

<400> SEQUENCE: 100

Met Asp Ala Gly Lys Ala Val Ser Asp Lys Lys Glu Gly Asp Val Thr
1               5                   10                  15

Pro Tyr Asp Pro Phe Arg Asp Arg Thr Thr Pro
            20                  25

<210> SEQ ID NO 101
<211> LENGTH: 19
<212> TYPE: PRT
<213> ORGANISM: Simian immunodeficiency virus

<400> SEQUENCE: 101

Met Asp Val Gln Gly Val Gly Leu Glu His Pro Glu Glu Val Ile Leu
1               5                   10                  15

Tyr Asp Pro

<210> SEQ ID NO 102
<211> LENGTH: 22
<212> TYPE: PRT
<213> ORGANISM: Simian immunodeficiency virus

<400> SEQUENCE: 102

Met Asp Lys Gly Glu Glu Glu Arg Thr Val Leu His Gln Asp Leu Ile
1               5                   10                  15

Arg Gln Tyr Lys Lys Pro
            20

<210> SEQ ID NO 103
<211> LENGTH: 22
<212> TYPE: PRT
<213> ORGANISM: Simian immunodeficiency virus

<400> SEQUENCE: 103

Met Asp Gln Glu Gln Glu Ala Arg Pro Gln Val Trp Glu Glu Leu Gln
1               5                   10                  15

Glu Glu Leu His Arg Pro
            20

<210> SEQ ID NO 104
<211> LENGTH: 19
<212> TYPE: PRT
<213> ORGANISM: Simian immunodeficiency virus

<400> SEQUENCE: 104

Met Glu Ser Glu Gly Asp Gly Met Ala Glu Ser Leu Leu Gln Asp Leu
1               5                   10                  15

His Arg Pro

<210> SEQ ID NO 105
<211> LENGTH: 22
<212> TYPE: PRT
<213> ORGANISM: Simian immunodeficiency virus

<400> SEQUENCE: 105

Met Asp Lys Gly Glu Ala Glu Gln Ile Val Ser His Gln Asp Leu Ser
1               5                   10                  15

```
Glu Asp Tyr Gln Lys Pro
            20

<210> SEQ ID NO 106
<211> LENGTH: 20
<212> TYPE: PRT
<213> ORGANISM: Simian immunodeficiency virus

<400> SEQUENCE: 106

Met Asp Lys Glu Glu Pro His Pro Leu Leu Gln Asp Leu His Arg
1               5                   10                  15

Pro Leu Gln Pro
            20

<210> SEQ ID NO 107
<211> LENGTH: 20
<212> TYPE: PRT
<213> ORGANISM: Simian immunodeficiency virus

<400> SEQUENCE: 107

Met Ala Gln Glu Glu Gly Leu Gln Val Trp Glu Glu Leu Gln Glu Glu
1               5                   10                  15

Leu Gln Arg Pro
            20

<210> SEQ ID NO 108
<211> LENGTH: 22
<212> TYPE: PRT
<213> ORGANISM: Simian immunodeficiency virus

<400> SEQUENCE: 108

Met Asp Lys Gly Glu Asp Glu Gln Gly Ala Tyr His Gln Asp Leu Ile
1               5                   10                  15

Glu Gln Leu Lys Ala Pro
            20

<210> SEQ ID NO 109
<211> LENGTH: 19
<212> TYPE: PRT
<213> ORGANISM: Simian immunodeficiency virus

<400> SEQUENCE: 109

Met Asp Val Arg Ala Val Gly Ser Glu Arg Ile Glu Glu Glu Thr Leu
1               5                   10                  15

Tyr Asn Pro

<210> SEQ ID NO 110
<211> LENGTH: 30
<212> TYPE: PRT
<213> ORGANISM: Simian immunodeficiency virus

<400> SEQUENCE: 110

Met Ser Ser Thr Asp Gln Ile Cys Gln Thr Gln Arg Val Pro Pro Ser
1               5                   10                  15

Phe Leu Glu Gly Thr Phe Leu Glu Lys Gly Pro Pro Thr Pro
            20                  25                  30

<210> SEQ ID NO 111
<211> LENGTH: 26
<212> TYPE: PRT
<213> ORGANISM: Simian immunodeficiency virus

<400> SEQUENCE: 111
```

Met Asp Gly Gln Glu Ala Gly Leu Glu Arg Gln Glu Glu Thr Leu
1               5                   10                  15

Tyr Asn Pro Phe Gln Ser Val Glu Thr Pro
            20                  25

<210> SEQ ID NO 112
<211> LENGTH: 28
<212> TYPE: PRT
<213> ORGANISM: Simian immunodeficiency virus

<400> SEQUENCE: 112

Met Ser Thr Gln Gly His Gln Gln Asp Gln Asp Gln Gly Lys Gly Thr
1               5                   10                  15

Leu Glu Glu Ala Tyr Lys Thr Asn Leu Glu Ala Pro
            20                  25

<210> SEQ ID NO 113
<211> LENGTH: 30
<212> TYPE: PRT
<213> ORGANISM: Simian immunodeficiency virus

<400> SEQUENCE: 113

Met Gln Gln Pro Glu Gln Glu Gln His Thr Gln Gln Lys Gln His Leu
1               5                   10                  15

Asp Gln Leu Glu Glu Ile Tyr Lys Glu Ala Ile Thr Asp Pro
            20                  25                  30

<210> SEQ ID NO 114
<211> LENGTH: 46
<212> TYPE: PRT
<213> ORGANISM: Simian immunodeficiency virus

<400> SEQUENCE: 114

Met Glu Thr Pro Leu Lys Glu Gln Glu Ser Ser Leu Arg Ser Ser Ser
1               5                   10                  15

Glu Pro Ser Ser Cys Thr Ser Glu Ala Val Ala Ala Thr Pro Gly Leu
            20                  25                  30

Ala Asn Gln Glu Glu Glu Ile Leu Trp Gln Leu Tyr Arg Pro
        35                  40                  45

<210> SEQ ID NO 115
<211> LENGTH: 21
<212> TYPE: PRT
<213> ORGANISM: Simian immunodeficiency virus

<400> SEQUENCE: 115

Met Gln Pro Leu Gln Asn Arg Pro Asp Leu Gly Glu Glu Ile Leu Ser
1               5                   10                  15

Gln Leu Tyr Arg Pro
            20

<210> SEQ ID NO 116
<211> LENGTH: 33
<212> TYPE: PRT
<213> ORGANISM: Simian immunodeficiency virus

<400> SEQUENCE: 116

Met Glu Pro Ser Gly Lys Glu Asp His Asn Cys Pro Pro Gln Asp Ser
1               5                   10                  15

Gly Gln Glu Glu Ile Asp Tyr Lys Gln Leu Leu Glu Glu Tyr Tyr Gln
            20                  25                  30

Pro

<210> SEQ ID NO 117
<211> LENGTH: 27
<212> TYPE: PRT
<213> ORGANISM: Simian immunodeficiency virus

<400> SEQUENCE: 117

Met Asp Val Gly Glu Val Ala Ser Asp Lys Lys Glu Glu Asp Ile Thr
1               5                   10                  15

His Phe Asp Pro Phe Arg Ala Arg Thr Thr Pro
            20                  25

<210> SEQ ID NO 118
<211> LENGTH: 19
<212> TYPE: PRT
<213> ORGANISM: Simian immunodeficiency virus

<400> SEQUENCE: 118

Met Asp Ala Arg Lys Val Asp Leu Asp Gln Gln Asp Ala Gly Thr His
1               5                   10                  15

Phe Glu Pro

<210> SEQ ID NO 119
<211> LENGTH: 23
<212> TYPE: PRT
<213> ORGANISM: Simian immunodeficiency virus

<400> SEQUENCE: 119

Met Ser Ser Lys Glu Glu Leu Arg Thr Thr Pro Ile Ser Asp Pro Phe
1               5                   10                  15

Gln Glu Glu Gly Arg Gly Pro
            20

<210> SEQ ID NO 120
<211> LENGTH: 21
<212> TYPE: PRT
<213> ORGANISM: Simian immunodeficiency virus

<400> SEQUENCE: 120

Met Asp Pro Ser Val Glu Glu Leu Pro Lys Glu Gln Arg Pro Gly Ala
1               5                   10                  15

Ala Pro Ala Thr Pro
            20

<210> SEQ ID NO 121
<211> LENGTH: 19
<212> TYPE: PRT
<213> ORGANISM: Simian immunodeficiency virus

<400> SEQUENCE: 121

Met Glu Glu Glu Met Asp Leu Phe Gln Gly Arg Gly Arg Gly Glu Ala
1               5                   10                  15

Asn His Pro

<210> SEQ ID NO 122
<211> LENGTH: 15
<212> TYPE: PRT
<213> ORGANISM: Simian immunodeficiency virus

<400> SEQUENCE: 122

Met Asn Ala Asp Ser Ile Asp Pro Phe Ala Gly Asn Lys Thr Pro
1               5                   10                  15

<210> SEQ ID NO 123
<211> LENGTH: 46
<212> TYPE: PRT
<213> ORGANISM: Simian immunodeficiency virus

<400> SEQUENCE: 123

Met Glu Thr Pro Leu Arg Glu Gln Glu Asn Ser Leu Lys Ser Ser Asn
1               5                   10                  15

Gly Arg Ser Ser Cys Thr Ser Glu Ala Ala Pro Thr Leu Glu Ser
            20                  25                  30

Ala Asn Leu Glu Glu Glu Ile Leu Ser Gln Leu Tyr Arg Pro
        35                  40                  45

<210> SEQ ID NO 124
<211> LENGTH: 21
<212> TYPE: PRT
<213> ORGANISM: Human immunodeficiency virus type 1

<400> SEQUENCE: 124

Arg Lys Thr Ala Cys Thr Thr Cys Tyr Cys Lys Lys Cys Cys Phe His
1               5                   10                  15

Cys Gln Val Cys Phe
            20

<210> SEQ ID NO 125
<211> LENGTH: 20
<212> TYPE: PRT
<213> ORGANISM: Human immunodeficiency virus type 1

<400> SEQUENCE: 125

Arg Thr Ala Cys Asn Asn Cys Tyr Cys Lys Lys Cys Cys Phe His Cys
1               5                   10                  15

Tyr Ala Cys Phe
            20

<210> SEQ ID NO 126
<211> LENGTH: 17
<212> TYPE: PRT
<213> ORGANISM: Human immunodeficiency virus type 1

<400> SEQUENCE: 126

Thr Pro Val Ser Cys Leu Arg Lys Gly Gly Arg Cys Trp Asn Arg Cys
1               5                   10                  15

Ile

<210> SEQ ID NO 127
<211> LENGTH: 21
<212> TYPE: PRT
<213> ORGANISM: Human immunodeficiency virus type 2

<400> SEQUENCE: 127

Leu Glu Thr Cys Asn Asn Thr Cys Tyr Cys Lys Glu Cys Cys Tyr His
1               5                   10                  15

Cys Gln Leu Cys Phe
            20

<210> SEQ ID NO 128
<211> LENGTH: 26
<212> TYPE: PRT

```
<213> ORGANISM: Human immunodeficiency virus type 1

<400> SEQUENCE: 128

Arg Thr Ala Cys Asn Asn Cys Tyr Cys L

```
Lys Gln Pro Ala Ser Gln Ser Arg Gly Asp Pro Thr Gly Pro Thr Glu
            35                  40                  45

Ser Lys Lys Val Glu Arg Glu Thr Glu Asp Pro Phe Asp
 50                  55                  60

<210> SEQ ID NO 134
<211> LENGTH: 76
<212> TYPE: PRT
<213> ORGANISM: Simian immunodeficiency virus

<400> SEQUENCE: 134

Leu Arg Lys Gly Leu Gly Ile Thr Tyr His Ala Phe Arg Thr Arg Arg
1               5                   10                  15

Lys Lys Ile Ala Ser Ala Asp Arg Ile Pro Val Pro Gln Gln Ser Ile
            20                  25                  30

Ser Ile Arg Gly Arg Asp Ser Gln Thr Thr Gln Glu Ser Gln Lys Lys
            35                  40                  45

Val Glu Glu Gln Ala Lys Ala Asn Leu Arg Ile Ser Arg Lys Asn Leu
 50                  55                  60

Gly Asp Glu Thr Arg Gly Pro Val Gly Ala Gly Asn
65                  70                  75

<210> SEQ ID NO 135
<211> LENGTH: 85
<212> TYPE: PRT
<213> ORGANISM: Human immunodeficiency virus type 1

<400> SEQUENCE: 135

Gly Asn Thr Arg Gln Ile Gly Ser Cys Gly Val Pro Phe Leu Lys Cys
1               5                   10                  15

Cys Lys Arg Lys Pro Phe Thr Arg Lys Gly Leu Gly Ile Ser Tyr Gly
            20                  25                  30

Arg Lys Lys Arg Arg Gln Arg Arg Ala Pro Gln Asp Ser Gln Thr
            35                  40                  45

His Gln Ala Ser Leu Ser Lys Gln Pro Ala Ser Gln Ser Arg Gly Asp
 50                  55                  60

Pro Thr Gly Pro Thr Glu Ser Lys Lys Val Glu Arg Glu Thr Glu
65                  70                  75                  80

Thr Asp Pro Phe Asp
                85

<210> SEQ ID NO 136
<211> LENGTH: 69
<212> TYPE: PRT
<213> ORGANISM: Human immunodeficiency virus type 2

<400> SEQUENCE: 136

Leu Asn Lys Gly Leu Gly Ile Trp Tyr Asp Arg Lys Gly Arg Arg Arg
1               5                   10                  15

Arg Ser Pro Lys Lys Ile Lys Ala His Ser Ser Ala Ser Asp Lys
            20                  25                  30

Ser Ile Ser Thr Arg Thr Arg Asn Ser Gln Pro Glu Glu Lys Gln Lys
            35                  40                  45

Lys Thr Leu Glu Thr Thr Leu Gly Thr Asp Cys Gly Pro Gly Arg Ser
            50                  55                  60

His Ile Tyr Ile Ser
65
```

```
<210> SEQ ID NO 137
<211> LENGTH: 63
<212> TYPE: PRT
<213> ORGANISM: Simian immunodeficiency virus

<400> SEQUENCE: 137

Leu Gln Lys Gly Leu Gly Ile Asn Tyr Ala Ser Arg Ala Arg Arg
1               5                   10                  15

Arg Ser Lys Glu Glu Asn Lys Ala Asp Lys Phe Pro Val Pro Asn His
            20                  25                  30

Arg Ser Ile Ser Thr Thr Arg Gly Asn Arg Lys Leu Gln Glu Lys Lys
        35                  40                  45

Glu Lys Thr Val Glu Lys Val Ala Thr Ser Thr Thr Ile Gly
    50                  55                  60

<210> SEQ ID NO 138
<211> LENGTH: 76
<212> TYPE: PRT
<213> ORGANISM: Simian immunodeficiency virus

<400> SEQUENCE: 138

Leu Gln Lys Gly Leu Gly Val Thr Tyr His Ala Pro Arg Thr Arg Arg
1               5                   10                  15

Lys Lys Ser Val Gln Pro Asn Arg Leu Ser Gln Gln Asp Gln Ser Ile
            20                  25                  30

Ser Thr Arg Gly Arg Asp Gly Gln Ala Thr Gln Glu Ser Gln Lys Lys
        35                  40                  45

Val Glu Arg Glu Thr Thr Thr Ala Gln Ile Leu Gly Arg Lys Asp Leu
    50                  55                  60

Glu Arg Asp Lys Arg Glu Ala Val Gly Ala Asn Ala
65                  70                  75

<210> SEQ ID NO 139
<211> LENGTH: 30
<212> TYPE: PRT
<213> ORGANISM: Simian immunodeficiency virus

<400> SEQUENCE: 139

His Lys Lys Ala Leu Gly Ile Arg Tyr Tyr Val Pro Arg Pro Arg Arg
1               5                   10                  15

Ala Ser Lys Lys Ile Ser His Asn Gln Val Ser Leu His Asn
            20                  25                  30

<210> SEQ ID NO 140
<211> LENGTH: 67
<212> TYPE: PRT
<213> ORGANISM: Simian immunodeficiency virus

<400> SEQUENCE: 140

His Cys Tyr Ala Cys Phe Leu Gln Lys Gly Leu Gly Ile Thr Tyr His
1               5                   10                  15

Val Ser Arg Ile Arg Arg Pro Lys Lys Asn His Ser Asn His Gln Asn
            20                  25                  30

Leu Val Ser Gln Gln Ser Ile Ser Ala Trp Gly Gly Asn Ser Gln Thr
        35                  40                  45

Thr Gln Glu Glu Lys Thr Lys Ile Pro Ala Ala Ala Glu Thr Ser Arg
    50                  55                  60

Arg Pro Gln
65
```

<210> SEQ ID NO 141
<211> LENGTH: 56
<212> TYPE: PRT
<213> ORGANISM: Simian immunodeficiency virus

<400> SEQUENCE: 141

Gln Lys Gly Leu Gly Val Thr Tyr His Ala Pro Arg Thr Arg Arg Lys
1               5                   10                  15

Lys Ile Arg Ser Leu Asn Leu Ala Pro Leu Gln His Gln Ser Ile Ser
            20                  25                  30

Thr Lys Trp Gly Arg Asp Gly Gln Thr Thr Pro Thr Ser Gln Glu Lys
        35                  40                  45

Val Glu Thr Thr Ala Gly Ser Asn
    50                  55

<210> SEQ ID NO 142
<211> LENGTH: 56
<212> TYPE: PRT
<213> ORGANISM: Simian immunodeficiency virus

<400> SEQUENCE: 142

Leu Gln Lys Gly Leu Gly Val Arg Tyr His Val Ser Arg Lys Arg Arg
1               5                   10                  15

Lys Thr Ser Thr Gln Asp Asn Gln Asp Pro Ile Arg Gln Gln Ser Ile
            20                  25                  30

Ser Thr Val Gln Arg Asn Gly Gln Thr Thr Glu Glu Gly Lys Thr Glu
        35                  40                  45

Val Glu Lys Ala Ala Ala Ala Asn
    50                  55

<210> SEQ ID NO 143
<211> LENGTH: 65
<212> TYPE: PRT
<213> ORGANISM: Simian immunodeficiency virus

<400> SEQUENCE: 143

Thr Gln Lys Gly Leu Gly Ile Ala Tyr Tyr Val Pro Arg Thr Arg Arg
1               5                   10                  15

Thr Val Lys Lys Ile Gln Asn Asn Gln Val Pro Ile His Asn Gln Ser
            20                  25                  30

Ile Ser Thr Trp Thr Arg Asn Ser Gln Ala Glu Lys Lys Ser Gln Thr
        35                  40                  45

Lys Val Gly Gln Ala Ala Thr Ala Asp His Thr Pro Gly Arg Lys Asn
    50                  55                  60

Ser
65

<210> SEQ ID NO 144
<211> LENGTH: 77
<212> TYPE: PRT
<213> ORGANISM: Simian immunodeficiency virus

<400> SEQUENCE: 144

Phe Leu Gln Lys Gly Leu Gly Val Thr Tyr His Ala Pro Arg Ile Arg
1               5                   10                  15

Arg Lys Lys Ile Ala Pro Leu Asp Arg Phe Pro Glu Gln Lys Gln Ser
            20                  25                  30

Ile Ser Thr Arg Gly Arg Asp Ser Gln Thr Thr Gln Lys Gly Gln Glu
        35                  40                  45

```
Lys Val Glu Thr Ser Ala Arg Thr Ala Pro Ser Leu Gly Arg Lys Asn
 50                  55                  60

Leu Ala Gln Gln Ser Gly Arg Ala Thr Gly Ala Ser Asp
 65                  70                  75

<210> SEQ ID NO 145
<211> LENGTH: 63
<212> TYPE: PRT
<213> ORGANISM: Human immunodeficiency virus type 1

<400> SEQUENCE: 145

Leu Asn Lys Gly Leu Gly Ile Ser Tyr Gly Arg Lys Lys Arg Lys Arg
 1               5                  10                  15

Arg Arg Gly Thr Pro Gln Ser Arg Gln Asp His Gln Asn Pro Val Pro
                20                  25                  30

Lys Gln Pro Leu Pro Thr Thr Arg Gly Asn Pro Thr Asn Pro Lys Glu
                35                  40                  45

Ser Lys Lys Glu Val Ala Ser Lys Thr Glu Thr Asn Gln Cys Asp
 50                  55                  60

<210> SEQ ID NO 146
<211> LENGTH: 61
<212> TYPE: PRT
<213> ORGANISM: Simian immunodeficiency virus

<400> SEQUENCE: 146

Leu Arg Lys Gly Leu Phe Leu Gln Lys Gly Leu Gly Ile Ser Tyr Arg
 1               5                  10                  15

Ser Tyr Ser Lys Lys Thr Lys Pro Asp Thr Thr Thr Ala Ala Ser Arg
                20                  25                  30

Asx Leu Gly Arg Val Thr Leu Ser Leu Tyr Leu Ser Arg Thr Thr Ser
                35                  40                  45

Thr Thr Trp Lys Arg Asp Ser Lys Thr Ala Lys Lys Glu
 50                  55                  60

<210> SEQ ID NO 147
<211> LENGTH: 44
<212> TYPE: PRT
<213> ORGANISM: Simian immunodeficiency virus

<400> SEQUENCE: 147

Thr Lys Lys Gly Leu Gly Ile Ser Tyr Gly Arg Lys Lys Arg Arg Arg
 1               5                  10                  15

Pro Ala Arg Thr Ala Asp Lys Asp Gln Asp Asn Gln Asp Pro Val Ser
                20                  25                  30

Lys Gln Ser Leu Ala Gly Thr Arg Ser Gln Gln Glu
                35                  40

<210> SEQ ID NO 148
<211> LENGTH: 98
<212> TYPE: PRT
<213> ORGANISM: Simian immunodeficiency virus

<400> SEQUENCE: 148

Thr Lys Lys Ala Leu Gly Ile Ser Tyr Gly Arg Lys Arg Arg Gly Arg
 1               5                  10                  15

Lys Ser Ala Gly Asp Asn Lys Thr His Gln Asp Pro Val Arg Gln Gln
                20                  25                  30

Ser Leu Pro Lys Arg Ser Arg Ile Gln Ser Ser Gln Glu Glu Ser Gln
```

```
                35                  40                  45
Lys Glu Val Glu Thr Glu Ala Gly Ser Gly Gly Arg Pro Arg Pro Glu
            50                  55                  60

Asp Ser Ser Ala Ser Ser Gly Arg Thr Ser Gly Thr Ser Ser Ser Gly
 65                  70                  75                  80

Ser Thr Arg Pro Val Ser Thr Ser Ser Gly Cys Trp Gly Pro Tyr Ser
                85                  90                  95

Lys Pro

<210> SEQ ID NO 149
<211> LENGTH: 74
<212> TYPE: PRT
<213> ORGANISM: Simian immunodeficiency virus

<400> SEQUENCE: 149

Leu Thr Lys Gly Leu Gly Ile Ser Tyr Gly Arg Lys Arg Lys Arg Arg
 1               5                  10                  15

Arg Ala Thr Ser Pro Val Pro Gly Leu Ser Ser Ser Lys Asn Pro Ala
                20                  25                  30

Arg Lys Gln Gly Arg Asp Thr Leu Phe Phe Leu Leu Arg Ser Leu Ser
            35                  40                  45

His Pro Thr Arg Asp Ser Gln Arg Pro Thr Glu Gln Ala Gln Ala Val
         50                  55                  60

Ala Thr Ala Ala Thr Pro Asp Arg Gln His
 65                  70

<210> SEQ ID NO 150
<211> LENGTH: 71
<212> TYPE: PRT
<213> ORGANISM: Simian immunodeficiency virus

<400> SEQUENCE: 150

His Cys Tyr Ala Cys Phe Phe Met Lys Lys Gly Leu Gly Ile Ser Tyr
 1               5                  10                  15

Gly Arg Lys Lys Arg Arg Gln Arg Arg Gly Ala Ser Lys Ser Asn Gln
                20                  25                  30

Asn His Gln Asp Ser Ile Pro Glu Gln Pro Phe Ser Gln Ser Arg Gly
            35                  40                  45

Asp Gln Ser Ser Pro Glu Lys Gln Glu Lys Lys Val Glu Ser Lys Thr
         50                  55                  60

Thr Ser Asp Pro Phe Gly Cys
 65                  70
```

TREATMENT OF CANCERS WITH IMMUNOSTIMULATORY HIV TAT DERIVATIVE POLYPEPTIDES

CROSS-REFERENCE TO RELATED APPLICATIONS

The present application is a continuation of U.S. patent application Ser. No. 14/505,977 filed Oct. 3, 2014, which claims the benefit under 35 USC § 119(e) to U.S. Provisional Patent Application 61/887,166 filed Oct. 4, 2013, the entire contents of both of which are incorporated by reference herein.

FIELD OF THE INVENTION

The present invention relates to the field of immune-based therapeutic agents for cancer.

BACKGROUND

Immune checkpoints represent inhibitory molecules that result in the inhibition of an effective immune response towards cancer which can result in tumor evasion. Immune checkpoint molecules such as the cytotoxic T-lymphocyte antigen 4 (CTLA-4) and programmed cell death 1 (PD-1) along with programmed cell death ligand 1 (PD-L1) are believed to be contributing to the immune dysfunction that accompanies cancer progression and their therapeutic blockade has shown clinical benefit. Specifically, the engagement of tumor PD-L1 with PD-1 on infiltrating Cytotoxic T lymphocytes (CTL) is believed to be an important mechanism underlying tumor evasion and immune resistance by inducing T-cell anergy, exhaustion, and programmed cell death. Understanding the manipulation of immune checkpoint molecules during the immune response is an important strategy for designing effective immunotherapies for human cancers.

The Human Immunodeficiency Virus (HIV) trans-activator of transcription (Tat) is a variable RNA binding peptide which increases viral RNA transcription and may initiate apoptosis in T4 cells and macrophages and possibly stimulates the over production of alpha interferon. However, the Tat protein isolated from HIV-infected long term non-progressors (LTNP) is different from Tat found in patients who have progressed to Acquired Immunodeficiency Syndrome (AIDS) as a result of their infections. The Tat protein found in LTNP is capable of trans-activating viral RNA; however, this immunostimulatory Tat does not induce apoptosis in T4 cells or macrophages and is not immunosuppressive. Variants of immunostimulatory Tat found in lentiviruses that infect monkey species yet do not result in the development of immunodeficiency and epidemic infection direct monocyte differentiation into dendritic cells (DCs) that stimulate cytotoxic T lymphocyte (CTL) responses. Thus, immunostimulatory Tat may have utility in stimulating an immune response towards human cancers.

Cancers and chronic infections are the most prominent examples of common human diseases that respond to immune-based treatments. Although infections were the first diseases to be controlled by immunization, clinical trials in humans have established that an immune response, particularly of the CTL arm of the immune system, could regress some human melanomas and renal cancers. These observations were broadened by the discovery that DCs, a specific class of antigen-presenting cells (APC), are particularly effective at initiating CTL activity against cancers and other diseases. Technologies that target and activate DCs have yielded some early successes against human cervical pre-malignancies caused by infection with Human Papilloma Virus (HPV) and human lung cancer. In contrast to chemotherapeutic drugs currently used against cancer, agents that provoke a CTL response against cancer potentially are accompanied by few side effects, owing to the great specificity of the immune response.

Efforts to develop immunotherapeutic drugs that treat cancer have been hampered by technical difficulties in targeting and activating DCs to deliver and sustain the required entry signals to the CTLs. Antigen targeting for the induction of a CTL response is a challenge, insofar as natural processing requires that the antigen enter the cytoplasm of the cell in order to bind to the immune system's major histocompatibility complex (MHC) Class I antigen, a prerequisite to CTL activation because the ligand for activating the T cell receptor on CTLs is a complex of antigen and MHC Class I. In almost all cases, protein antigens, even when they are coupled with a DC co-activator, enter exclusively into the alternative MHC Class II antigen presentation pathway that excludes CTL stimulation. This can be overcome, in part, by peptide-based technologies, because peptides bind to MHC Class I that is already on the surface of the DC. However, this technology is non-specific, and most peptides are poor DC activators, which limits their efficacy as treatments for human cancer.

A limited group of biological proteins are known to stimulate a CTL response. Variants and derivatives of the Human Immunodeficiency Virus 1 (HIV-1) trans-activator of transcription (Tat) can stimulate this CTL response. Additional biologics that are currently known to directly trigger a CTL response are based on heat shock proteins (HSP), or on the outer coat protein of certain bacteria. Heat shock proteins have shown limited efficacy in the treatment of certain genital neoplasms related to HPV infection.

SUMMARY OF THE INVENTION

Disclosed herein are derivatives of the Human Immunodeficiency Virus (HIV) trans-activator of transcription (Tat) protein for use as cancer therapeutic agents. Artificial immunostimulatory Tat derivative polypeptides have the potential to treat cancer.

In one embodiment, a trans-activator of transcription (Tat) derivative polypeptide is provided having an amino acid sequence comprising, in the following order: (i) a transcription factor (TF) domain sequence from a human immunodeficiency virus (HIV) or a simian immunodeficiency virus (SIV) Tat protein, (ii) a cysteine-rich domain sequence from SIV, HIV, or a defensin, and (iii) a C-terminal domain sequence from a HIV or SIV Tat protein.

Also disclosed herein is a pharmaceutical composition comprising a Tat derivative polypeptide disclosed herein.

In one embodiment of the Tat derivative polypeptide, the HIV is HIV-1 or HIV-2. In another embodiment, the HIV-1 Tat is from a long-term non-progressor. In another embodiment, the SIV is from a host selected from Table 2. In another embodiment, the defensin is an α-defensin or a β-defensin. In yet another embodiment, the Tat derivative polypeptide further comprises an arginine-rich domain from HIV-1 or HIV-2 Tat.

In another embodiment of the Tat derivative polypeptide, at least one of the amino acids in the TF domain is deleted or substituted with an alanine, an aspartic acid, a glutamic acid, a glycine, a lysine, a glutamine, an arginine, a serine, or a threonine. In another embodiment, the at least one substituted amino acid is a proline.

In certain embodiments, the TF domain comprises an amino acid sequence of one of SEQ ID NOs:96-123. In other embodiments, the cysteine-rich domain comprises an amino acid sequence of one of SEQ ID NOs:124-132. In other embodiments, the C-terminal domain comprises an amino acid sequence of one of SEQ ID NOs:133-150.

In another embodiment, the Tat derivative polypeptide has greater than 85% sequence identity to one of SEQ ID NOs 5-95. In another embodiment, the Tat derivative polypeptide is not one of SEQ ID NOs:2, 3, or 4.

Also disclosed herein is a method of treating cancer comprising administering a therapeutically effective amount of a Tat derivative polypeptide or pharmaceutical composition disclosed herein to a subject in need thereof; and causing cessation of growth of the cancer or regression of the cancer in the subject.

Also disclosed herein is a method of reducing tumor burden in a subject with cancer, the method comprising administering a therapeutically effective amount of a Tat derivative polypeptide or a pharmaceutical composition disclosed herein, to a subject in need thereof; and causing regression of the cancer in the subject.

Also disclosed herein is a method of inhibiting the suppression of an anti-tumor immune response in a subject with cancer, the method comprising administering a therapeutically effective amount of a Tat derivative polypeptide or a pharmaceutical composition disclosed herein to the subject; wherein the administration results in reduction or inhibition of growth of the cancer or in regression of the cancer in the subject.

Also disclosed herein is a method of treating a PD-L1-expressing tumor in a subject with cancer, the method comprising administering a therapeutically effective amount of a Tat derivative polypeptide or a pharmaceutical composition disclosed herein; wherein the administration results in reduction or inhibition of growth of the cancer or in regression of the cancer in the subject.

In one embodiment of the methods, the Tat derivative polypeptide has greater than 85% sequence identity to one of SEQ ID NOs 5-95.

In one embodiment of the methods, the Tat derivative polypeptide is administered in a plurality of doses. In another embodiment of the methods or uses, the administration comprises a repetitive administration cycle wherein each cycle comprises administering a plurality of doses of the Tat derivative polypeptide in a defined time period followed by a rest period and wherein the cycle is repeated a plurality of times. In another embodiment of the methods or uses, the administration comprises a repetitive administration cycle wherein each cycle comprises administering a plurality of doses of the Tat derivative polypeptide in a defined time period followed by a administration of one or a plurality of doses of a therapeutic agent in a defined time period and wherein the cycle is repeated a plurality of times. In another embodiment of the methods or uses, the therapeutic agent is cyclophosphamide.

In another embodiment of the methods, the cancer is adrenocortical carcinoma, anal cancer, appendix cancer, astrocytoma, basal-cell carcinoma, bile duct cancer, bladder cancer, bone cancer, brain cancer, breast cancer, bronchial adenomas/carcinoids, carcinoid tumor, cervical cancer, chronic myeloproliferative disorders, colon cancer, desmoplastic small round cell tumor, endometrial cancer, ependymoma, esophageal cancer, Ewing's sarcoma, germ cell tumors, eye cancer, gallbladder cancer, gastric cancer, gastrointestinal carcinoid tumor, gastrointestinal stromal tumor (GIST), gestational trophoblastic tumor, glioma, gastric carcinoid, head and neck cancer, heart cancer, hepatocellular cancer, Hodgkin's lymphoma, hypopharyngeal cancer, islet cell carcinoma, Kaposi sarcoma, kidney cancer, leukemias, lip and oral cavity cancer, liposarcoma, liver cancer, lung cancer, lymphomas, macroglobulinemia, medulloblastoma, melanoma, merkel cell carcinoma, mesothelioma, mouth cancer, multiple myeloma/plasma cell neoplasm, mycosis fungoides, nasal cavity and paranasal sinus cancer, nasopharyngeal carcinoma, neuroblastoma, oral cancer, oropharyngeal cancer, ovarian cancer, ovarian epithelial cancer, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, prostate cancer, rectal cancer, renal cell carcinoma, retinoblastoma, rhabdomyosarcoma, salivary gland cancer, sarcoma, Sézary syndrome, skin cancer, squamous cell carcinoma, stomach cancer, testicular cancer, throat cancer, thymoma, thyroid cancer, urethral cancer, uterine cancer, uterine sarcoma, vaginal cancer, vulvar cancer, Waldenström macroglobulinemia, or Wilms tumor.

In another embodiment of the methods, at least one pre-treatment tumor from the subject contains at least 5% PD-L1-expressing cells, between 5% and 20% PD-L1-expressing cells, between 5% and 15% PD-L1-expressing cells, or between 5% and 10% PD-L1-expressing cells.

BRIEF DESCRIPTION OF THE DRAWINGS

FIG. 6B depicts mice implanted SC with $2 \times 10^5$ SM1 breast cancer cells and treated SC with Nani-P2 (40 ng) on days 0, 7, 14, and 21. The difference in primary tumor growth between control and Nani-P2 treated SM1 animals was highly statistically significant (p<0.01***).

In FIG. 8A, two groups of 10 BALB/c mice were injected with $1 \times 10^4$ 4 T1 cells in the mammary pad on day 0. One group was dosed with Nani-P2 (40 ng) weekly for three weeks beginning at day 14. A second group was PBS-treated and used as control. Tumor burden was highly significant by day 22 and remained so throughout the duration of the trial (p<0.01). Mice were sacrificed when tumor diameter reached 15 mm, at which time lung metastases were counted (FIG. 8B). Data represent total lung metastases as quantitated by two observers blinded to the treatment protocol (p<0.01).

FIG. 14A depicts IHC staining with PD-L1 antibodies in a PBS control animal. PD-L1 staining was observed in cells with a morphological resemblance to myeloid-derived suppressor cells, tumor-associated macrophage, as well as tumor-associated dendritic cells and fibroblast. FIG. 14B depicts IHC staining in a Nani-P2 treated mouse. FIG. 14C depicts IHC staining of infiltrating CD8+ cytotoxic lymphocytes (CTL) in a PBS control animal. FIG. 14D depicts IHC staining of CD8+ CTL in a Nani-P2 treated mouse.

DETAILED DESCRIPTION

Figure 1:
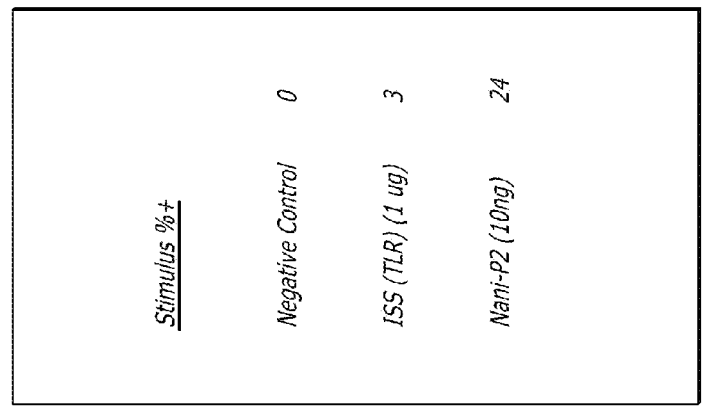
FIG. 1 depicts stimulation of human monocytes with Tat derivatives.
Figure 1:
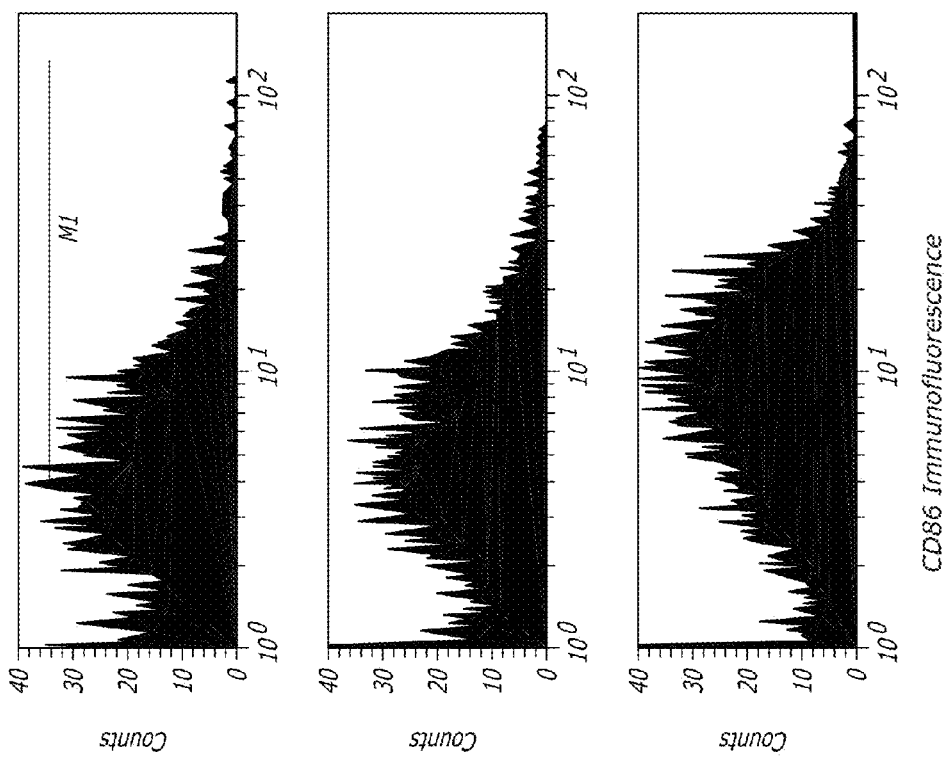

A series of artificial Human Immunodeficiency Virus (HIV) trans-activator of transcription (Tat) protein derivatives has been designed which are active in cancer. The molecules are referred to herein as "Tat derivative polypeptides," "Tat derivatives," or "Precision Immune Stimulants" (PINS) and comprise Tat molecules having modifications to change Tat from being immunosuppressive to immunostimulatory.

Despite a relative abundance of tumor-associated antigens, cancer has proven to be a difficult target for immunotherapeutics. Evidence has accumulated that the refractory state of cancer to immunotherapeutics could derive from immune suppression that accompanies established cancers. Epidemiological studies have shown that women with HIV infection, and even Acquired Immunodeficiency Syndrome (AIDS), were paradoxically protected from developing breast cancer, even in late-stage disease when immunodeficiency is pronounced.

The HIV-Tat protein can repetitively trigger precursor cells of the innate immune lineage into activated antigen presenting cells (APC). These observations have been confirmed in specific reference to the dendritic cell APC, whose activation initiates rounds of HIV replication even in AIDS. Taken together, these data supported the conclusion that Tat had a counter suppressive activity. It is hypothesized that these observations on Tat could be linked to the epidemiological data on breast cancer through the theory that Tat in HIV-infected individuals was chronically stimulating innate immunity thereby restricting breast cancer progression.

Tat Derivative Polypeptides

The HIV Tat protein is a variable RNA binding protein of 86 to 110 amino acids in length that is encoded on two separate exons of the HIV genome. Tat is highly conserved among all human lentiviruses and is essential for viral replication. When lentivirus Tat binds to the TAR (trans-activation responsive) RNA region, transcription (conversion of viral RNA to DNA and then to messenger RNA) levels increase significantly. It has been demonstrated that Tat increases viral RNA transcription, and it has been proposed that Tat may initiate apoptosis (programmed cell death) in T4 cells and macrophages (a key part of the body's immune surveillance system for HIV infection) and may stimulate the over production of α-interferon (α-interferon is a well established immunosuppressive cytokine).

Extracellular Tat's presence early in the course of HIV infection could reduce a patient's immune response, giving the virus an advantage over the host. Furthermore, the direct destruction of T4 cells and induction of α-interferon production could help explain the lack of a robust cellular immune response seen in AIDS patients, as well as accounting for the initial profound immunosuppression.

Based on molecular analysis, the Tat protein (SEQ ID NO:1) includes four distinct domains: (1) the transduction (SH3) domain (amino acids 3-19); (2) the cysteine-rich ligand binding domain (amino acids 22-37); (3) the membrane translocation sequence (amino acids 47-57) and (4) a tail portion encoded by the second exon (amino acids 73-101).

The amino terminal portion of Tat includes a short peptide region from a nuclear transcription factor (TF) typically flanked by proline residues. This region determines, at least in part, how stimulatory or suppressive the Tat polypeptide is for cells of the immune system, particularly innate immune cells such as dendritic cells (DC) and macrophages (antigen-presenting cells or APCs). Consequently, it is predicted that modifications to the TF region can render the polypeptides more active in the therapy of cancer and other chronic diseases.

HIV-1 Tat SH3 binding domain is identical to the sequence found in another TF protein, hairless (hr), that had previously been shown to have immunosuppressive properties in mice. Mice carrying the hr mutation develop an immune dysregulation, now most commonly called "the TH1 to TH2 shift," that is the sine qua non of HIV-infected individuals who are progressing to AIDS. Further analysis established that SH3 binding sequence derived from the hr gene is a nearly invariant feature of Tat isolated from HIV-1, and a very consistent feature of HIV-2.

In contrast, primates infected by certain strains of simian immunodeficiency virus (SIV), a lentivirus closely related to HIV, rarely progress to AIDS, or do so unpredictably. This observation, coupled with the discovery of a putatively immunosuppressive hr TF fragment in immunosuppressive HIV-1 Tat, suggested that some primates could have a different (or no) TF fragment at the amino terminus of SIV Tat. Tat from certain SIV-infected sooty mangabeys with an attenuated course of immunodeficiency has at its amino terminus a fragment from the TF TARA instead of the TF hr.

In general, an immunostimulatory Tat derivative polypeptide for the treatment of cancer comprises at least three regions (domains). The first domain is a derivatized nuclear transcription factor (TF) region of Tat, the second domain is a cysteine-rich region, and the third region is a C-terminal Tat domain. Each of these domains comprises a sequence from a Tat protein from a source including, but not limited to, HIV-1 or HIV-2 infected progressors, long-term non-progressors, long-term survivors, elite controllers, and/or SIV infected non-human primate species. Alternatively, cysteine-rich defensin molecules can be substituted in place for a Tat-derived cysteine-rich domain. In certain embodiments, the cysteine-rich domain from a retrovirus is combined with a TF domain and C-terminal domain from non-human primate Tat sequence. In another embodiment, non-human primate cysteine-rich domain is combined with a TF domain and C-terminal domain from a retrovirus. In yet another embodiment, the sequence comprising a fragment of the region which maintains the immunostimulatory activity of the full length domain. Exemplary retroviruses are SIV, HIV, feline immunodeficiency virus (FIV), bovine immunodeficiency virus (BIV), Herpes Simplex Virus 1, Herpes Simplex Virus 2, or equine infectious anemia virus (EIAV). In one embodiment, the retrovirus is a lentivirus such as HIV or SIV. In another embodiment the HIV is HIV-1 or HIV-2.

Thus disclosed herein are Tat derivative polypeptides comprising an amino acid sequence including a transcription factor (TF) domain, a cysteine-rich domain, and a C-terminal domain in that order, wherein each of the TF domain and the C-terminal domain are from a retrovirus Tat protein, and the cysteine-rich domain is from a retrovirus or a defensin, such as α-defensin or β-defensin. Exemplary non-limiting Tat derivative polypeptides are presented in Table 1. The TF region has a C-terminal proline residue and the cysteine-rich region has a C-terminal phenylalanine. If the native TF sequence does not have a proline residue at the C-terminus, a proline may be inserted at the C-terminus. Exemplary SIV infected non-human primate species are listed in Table 2.

In another embodiment, the modified Tat polypeptide further comprises an arginine-rich domain from a lentiviral Tat protein. The arginine-rich domain is found within the C-terminal region.

The TF domain, cysteine-rich domain, and C-terminal domain sequences are arranged in the Tat derivative polypeptide in that order.

In additional embodiments, one or more amino acids, including but not limited to proline, in the TF domain is deleted or substituted with a conservative amino acid substitution, such as with an alanine, an aspartic acid, a glutamic acid, a glycine, a lysine, a glutamine, an arginine, a serine, or a threonine.

In one embodiment, the TF domain comprises, consists essentially of, or consists of, an amino acid sequence of one of SEQ ID NOs:96-123. In another embodiment, the cysteine-rich domain comprises, consists essentially of, or consists of, an amino acid sequence of one of SEQ ID NOs: 124-132. In another embodiment, the cysteine-rich domain comprises, consists essentially of, or consists of, an amino acid sequence of one of SEQ ID NOs:133-150.

TABLE 1

Exemplary Tat derivative polypeptides

| SEQ ID NO. | Amino Acid Sequence | Source: TF domain* | Source: cysteine-rich domain‡ | Source: C-terminal domain |
|---|---|---|---|---|
| 2 | *MEPVDANLEAWKHAGSQP*RKTACTTCYCKKCCFHCQVCFTRKGLGISYGRKKRRQRRRAPQDSQTHQASLSKQPASQSRGDPTGPTESKKKVERETETDPFD (Nani-P1, MPM1, PIN-1) | HIV-1 | HIV-1 | HIV-1 |

TABLE 1-continued Exemplary Tat derivative polypeptides

| SEQ ID NO. | Amino Acid Sequence | Source TF domain* | Source cysteine-rich domain† | Source C-terminal domain |
|---|---|---|---|---|
| 3 | MDPKGEEDQDVSHQDLIKQYRKPRTACNNC YCKKCCFHCYACFLRKGLGITYHAFRTRRK KIASADRIPVPQQSISIRGRDSQTTQESQK KVEEQAKANLRISRKNLGDETRGPVGAGN (Nani-P2, ASH4, PIN-2) | SIVagmVer | HIV-1 | SIVagmVer |
| 4 | METPLKEQENSLESCREHSSSISEVDVPTP VSCLRKGGRCWNRCIGNTRQIGSCGVPFLK CCKRKPFTRKGLGISYGRKKRRQRRRAPQD SQTHQASLSKQPASQSRGDPTGPTESKKKV ERETETDPFD (Nani-P3, TMPD5, PIN-3) | SIVsmm | Murine βdefensin | HIV-1 |
| 5 | METPLKEQESSLESSREHSSSISEVDADTP ESASLEEEILSQLYRPLETCNNTCYCKECC YHCQLCFLNKGLGIWYDRKGRRRRSPKKIK AHSSSASDKSISTRTRNSQPEEKQKKTLET TLGTDCGPGRSHIYIS | SIVsmm | HIV-2 | HIV-2 |
| 6 | MDAGKAVSDKKEGDVTPYDPFRDRTTPLET CNNTCYCKECCYHCQLCFLNKGLGIWYDRK GRRRRSPKKIKAHSSSASDKSISTRTRNSQ PEEKQKKTLETTLGTDCGPGRSHIYISA | SIVmnd | HIV-2 | HIV-2 |
| 7 | MDVQGVGLEHPEEVILYDPRTACNNCYCKK CCFHCYACFLQKGLGINYASRARRRRSKEE NKADKFPVPNHRSISTTRGNRKLQEKKEKT VEKKVATSTTIG | SIVdeb | HIV-1 | SIVdeb |
| 8 | MDKGEEERTVLHQDLIRQYKKPRTACNNCY CKKCCFHCYACFLRKGLGITYHAFRTRRKK IASADRIPVPQQSISIRGRDSQTTQESQKK VEEQAKANLRISRKNLGDETRGPVGAGN | SIVagmVer | HIV-1 | SIVagmVer |
| 9 | MDPKGEEDQDVSHQDLIKQYRKPRTACNNC YCKKCCFHCYACFHCYACFLQKGLGVTYHA PRTRRKKSVQPNRLSQQDQSISTRGRDGQA TQESQKKVERETTTAQILGRKDLERDKREA VGANA | SIVagmVer | HIV-1 | SIVagmVer |
| 10 | MDQEQEARPQVWEELQEELHRPRTACNNCY CKKCCFHCYACFLRKGLGITYHAFRTRRKK IASADRIPVPQQSISIRGRDSQTTQESQKK VEEQAKANLRISRKNLGDETRGPVGAGN | SIVagmSab | HIV-1 | SIVagmVer |
| 11 | MDPKGEEDQDVSHQDLIKQYRKPRTACNNC YCKKCCFHCYACFHKKALGIRYYVPRPRRA SKKISHNQVSLHN | SIVagmVer | HIV-1 | SIVagmSab |
| 12 | MESEGDGMAESLLQDLHRPRTACNNCYCKK CCFHCYACFLRKGLGITYHAFRTRRKKIAS ADRIPVPQQSISIRGRDSQTTQESQKKVEE QAKANLRISRKNLGDETRGPVGAGN | SIVagmTan | HIV-1 | SIVagmVer |
| 13 | MDPKGEEDQDVSHQDLIKQYRKPRTACNNC YCKKCCFHCYACFHCYACFLQKGLGITYHV SRIRRPKKNHSNHQNLVSQQSISAWGGNSQ TTQEEKTKIPAAAETSRRPQ | SIVagmVer | HIV-1 | SIVagmTan |
| 14 | MDKGEAEQIVSHQDLSEDYQKPRTACNNCY CKKCCFHCYACFLRKGLGITYHAFRTRRKK IASADRIPVPQQSISIRGRDSQTTQESQKK VEEQAKANLRISRKNLGDETRGPVGAGN | SIVagmVer | HIV-1 | SIVagmVer |
| 15 | MDPKGEEDQDVSHQDLIKQYRKPRTACNNC YCKKCCFHCYACFLQKGLGVTYHAPRTRRK KIRSLNLAPLQHQSISTKWGRDGQTTPTSQ EKVETTAGSN | SIVagmVer | HIV-1 | SIVagmVer |

TABLE 1-continued

Exemplary Tat derivative polypeptides

| | | Source | | |
|---|---|---|---|---|
| SEQ ID NO. | Amino Acid Sequence | TF domain* | cysteine-rich domain† | C-terminal domain |
| 16 | MDKEEEPHPLLQDLHRPLQPRTACNNCYCK KCCFHCYACFLRKGLGITYHAFRTRRKKIA SADRIPVPQQSISIRGRDSQTTQESQKKVE EQAKANLRISRKNLGDETRGPVGAGN | SIVagmGri | HIV-1 | SIVagmVer |
| 17 | MDPKGEEDQDVSHQDLIKQYRKPRTACNNC YCKKCCFHCYACFLQKGLGVRYHVSRKRRK TSTQDNQDPIRQQSISTVQRNGQTTEEGKT EVEKAAAAN | SIVagmVer | HIV-1 | SIVagmGri |
| 18 | MAQEEGLQVWEELQEELQRPRTACNNCYCK KCCFHCYACFLRKGLGITYHAFRTRRKKIA SADRIPVPQQSISIRGRDSQTTQESQKKVE EQAKANLRISRKNLGDETRGPVGAGN | SIVagmSab | HIV-1 | SIVagmVer |
| 19 | MDPKGEEDQDVSHQDLIKQYRKPRTACNNC YCKKCCFHCYACFTQKGLGIAYYVPRTRRT VKKIQNNQVPIHNQSISTWTRNSQAEKKSQ TKVGQAATADHTPGRKNS | SIVagmVer | HIV-1 | SIVagmSab |
| 20 | MDKGEDEQGAYHQDLIEQLKAPRTACNNCY CKKCCFHCYACFLRKGLGITYHAFRTRRKK IASADRIPVPQQSISIRGRDSQTTQESQKK VEEQAKANLRISRKNLGDETRGPVGAGN | SIVagmVer | HIV-1 | SIVagmVer |
| 21 | MDPKGEEDQDVSHQDLIKQYRKPRTACNNC YCKKCCFHCYACFFLQKGLGVTYHAPRIRR KKIAPLDRFPEQKQSISTRGRDSQTTQKGQ EKVETSARTAPSLGRKNLAQQSGRATGASD | SIVagmVer | HIV-1 | SIVagmVer |
| 22 | MDVRAVGSERIEEETLYNPRKTACTTCYCK KCCFHCQVCFTRKGLGISYGRKKRRQRRRA PQDSQTHQASLSKQPASQSRGDPTGPTESK KKVERETETDPFD | SIVrcm | HIV-1 | HIV-1 |
| 23 | MDVRAVGSERIEEETLYNPRTACNNCYCKK CCFHCYACFLRKGLGITYHAFRTRRKKIAS ADRIPVPQQSISIRGRDSQTTQESQKKVEE QAKANLRISRKNLGDETRGPVGAGN | SIVrcm | HIV-1 | SIVagmVer |
|

TABLE 1-continued

Exemplary Tat derivative polypeptides

| SEQ ID NO. | Amino Acid Sequence | Source TF domain* | cysteine-rich domain† | C-terminal domain |
|---|---|---|---|---|
| 30 | MDGQEAGLERQEEETLYNPFQSVETP*RKTA CTTCYCKKCCFHCQVCF*TRKGLGISYGRKK RRQRRRAPQDSQTHQASLSKQPASQSRGDP TGPTESKKKVERETETDPFD | SIVagi | HIV-1 | HIV-1 |
| 31 | MDGQEAGLERQEEETLYNPFQSVETP*RTAC NNCYCKKCCFHCYACF*LRKGLGITYHAFRT RRKKIASADRIPVPQQSISIRGRDSQTTQE SQKKVEEQAKANLRISRKNLGDETRGPVGA GN | SIVagi | HIV-1 | SIVagmVer |
| 32 | MDGQEAGLERQEEETLYNPFQSVETP*LETC NNTCYCKECCYHCQLCF*LNKGLGIWYDRKG RRRRSPKKIKAHSSSASDKSISTRTRNSQP EEKQKKTLETTLGTDCGPGRSHIYIS | SIVagi | HIV-2 | HIV-2 |

TABLE 1-continued

Exemplary Tat derivative polypeptides

| SEQ ID NO. | Amino Acid Sequence | Source TF domain* | Source cysteine-rich domain† | Source C-terminal domain |
|---|---|---|---|---|
| 43 | METPLKEQESSLRSSSEPSSCTSEAVAATP GLANQEEEILWQLYRPRTACNNCYCKKCCF HCYACFLRKGLGITYHAFRTRRKKIASADR IPVPQQSISIRGRDSQTTQESQKKVEEQAK ANLRISRKNLGDETRGPVGAGN | SIVstm | HIV-1 | SIVagmVer |
| 44 | METPLKEQESSLRSSSEPSSCTSEAVAATP GLANQEEEILWQLYRPLETCNNTCYCKECC YHCQLCFLNKGLGIWYDRKGRRRRSPKKIK AHSSSASDKSISTRTRNSQPEEKQKKTLET TLGTDCGPGRSHIYIS | SIVstm | HIV-2 | HIV-2 |
| 45 | METPLKEQESSLRSSSEPSSCTSEAVAATP GLANQEEEILWQLYRPTTACSKCYCKMCCW HCQLCFLNKGLGISYGRKKRKRRRGTPQSR QDHQNPVPKQPLPTTRGNPTNPKESKKEVA SKTETNQCD | SIVstm | HIV-1 | HIV-1 |
| 46 | MDKGEEERTVLHQDLIRQYKKPRKTACTTC YCKKCCFHCQVCFTRKGLGISYGRKKRRQR RRAPQDSQTHQASLSKQPASQSRGDPTGPT ESKKKVERETETDPFD | SIVagmVer | HIV-1 | HIV-1 |
| 47 | MDKGEEERTVLHQDLIRQYKKPRTACNNCY CKKCCFHCYACFLRKGLGITYHAFRTRRKK IASADRIPVPQQSISIRGRDSQTTQESQKK VEEQAKANLRISRKNLGDETRGPVGAGN | SIVagmVer | HIV-1 | SIVagmVer |
| 48 | MDKGEEERTVLHQDLIRQYKKPLETCNNTC YCKECCYHCQLCFLNKGLGIWYDRKGRRRR SPKKIKAHSSSASDKSISTRTRNSQPEEKQ KKTLETTLGTDCGPGRSHIYIS | SIVagmVer | HIV-2 | HIV-2 |
| 49 | MDKGEEERTVLHQDLIRQYKKPTTACSKCY CKMCCWHCQLCFLNKGLGISYGRKKRKRRR GTPQSRQDHQNPVPKQPLPTTRGNPTNPKE SKKEVASKTETNQCD | SIVagmVer | HIV-1 | HIV-1 |
| 50 | MQPLQNRPDLGEEILSQLYRPRKTACTTCY CKKCCFHCQVCFTRKGLGISYGRKKRRQRR RAPQDSQTHQASLSKQPASQSRGDPTGPTE SKKKVERETETDPFD | SIVmac | HIV-1 | HIV-1 |
| 51 | MQPLQNRPDLGEEILSQLYRPRTACNNCYC KKCCFHCYACFLRKGLGITYHAFRTRRKKI ASADRIPVPQQSISIRGRDSQTTQESQKKV EEQAKANLRISRKNLGDETRGPVGAGN | SIVmac | HIV-1 | SIVagmVer |
| 52 | MQPLQNRPDLGEEILSQLYRPLETCNNTCY CKECCYHCQLCFLNKGLGIWYDRKGRRRRS PKKIKAHSSSASDKSISTRTRNSQPEEKQK KTLETTLGTDCGPGRSHIYIS | SIVmac | HIV-2 | HIV-2 |
| 53 | MQPLQNRPDLGEEILSQLYRPTTACSKCYC KMCCWHCQLCFLNKGLGISYGRKKRKRRRG TPQSRQDHQNPVPKQPLPTTRGNPTNPKES KKEVASKTETNQCD | SIVmac | HIV-1 | HIV-1 |
| 54 | METPLKEQESSLESSREHSSSISEVDADTP ESASLEEEILSQLYRPRKTACTTCYCKKCC FHCQVCFTRKGLGISYGRKKRRQRRRAPQD SQTHQASLSKQPASQSRGDPTGPTESKKKV ERETETDPFD | SIVsmm | HIV-1 | HIV-1 |
| 55 | METPLKEQESSLESSREHSSSISEVDADTP ESASLEEEILSQLYRPRTACNNCYCKKCCF HCYACFLRKGLGITYHAFRTRRKKIASADR IPVPQQSISIRGRDSQTTQESQKKVEEQAK ANLRISRKNLGDETRGPVGAGN | SIVsmm | HIV-1 | SIVagmVer |

TABLE 1-continued

Exemplary Tat derivative polypeptides

| SEQ ID NO. | Amino Acid Sequence | Source TF domain* | cysteine-rich domain† | C-terminal domain |
|---|---|---|---|---|
| 56 | METPLKEQESSLESSREHSSSISEVDADTP ESASLEEEILSQLYRPTTACSKCYCKMCCW HCQLCFLNKGLGISYGRKKRKRRRGTPQSR QDHQNPVPKQPLPTTRGNPTNPKESKKEVA SKTETNQCD | SIVsmm | HIV-1 | HIV-1 |
| 57 | MDAGKAVSDKKEGDVTPYDPFRDRTTPRKT ACTTCYCKKCCFHCQVCFTRKGLGISYGRK KRRQRRRAPQDSQTHQASLSKQPASQSRGD PTGPTESKKKVERETETDPFD | SIVmnd | HIV-1 | HIV-1 |
| 58 | MDAGKAVSDKKEGDVTPYDPFRDRTTPRTA CNNCYCKKCCFHCYACFLRKGLGITYHAFR TRRKKIASADRIPVPQQSISIRGRDSQTTQ ESQKKVEEQAKANLRISRKNLGDETRGPVG AGN | SIVmnd | HIV-1 | HIV-1 |
| 59 | MDAGKAVSDKKEGDVTPYDPFRDRTTPTTA CSKCYCKMCCWHCQLCFLNKGLGISYGRKK RKRRRGTPQSRQDHQNPVPKQPLPTTRGNP TNPKESKKEVASKTETNQCD | SIVmnd | HIV-1 | HIV-1 |
| 60 | MEPSGKEDHNCPPQDSGQEEIDYKQLLEEY YQPRKTACTTCYCKKCCFHCQVCFTRKGLG ISYGRKKRRQRRRAPQDSQTHQASLSKQPA SQSRGDPTGPTESKKKVERETETDPFD | SIVmnd | HIV-1 | HIV-1 |
|

TABLE 1-continued

Exemplary Tat derivative polypeptides

| SEQ ID NO. | Amino Acid Sequence | Source TF domain* | cysteine-rich domain† | C-terminal domain |
|---|---|---|---|---|
| 69 | MDARKVDLDQQDAGTHFEPRTACNNCYCKK CCFHCYACFLRKGLGITYHAFRTRRKKIAS ADRIPVPQQSISIRGRDSQTTQESQKKVEE QAKANLRISRKNLGDETRGPVGAGN | SIVdrl | HIV-1 | SIVagmVer |
| 70 | MDARKVDLDQQDAGTHFEPLETCNNTCYCK ECCYHCQLCFLNKGLGIWYDRKGRRRRSPK KIKAHSSSASDKSISTRTRNSQPEEKQKKT LETTLGTDCGPGRSHIYIS | SIVdrl | HIV-2 | HIV-2 |
| 71 | MDARKVDLDQQDAGTHFEPTTACSKCYCKM CCWHCQLCFLNKGLGISYGRKKRKRRRGTP QSRQDHQNPVPKQPLPTTRGNPTNPKESKK EVASKTETNQCD | SIVdrl | HIV-1 | HIV-1 |
| 72 | MSSKEELRTTPISDPFQEEGRGPRKTACTT CYCKKCCFHCQVCFTRKGLGISYGRKKRRQ RRRAPQDSQTHQASLSKQPASQSRGDPTGP TESKKKVERETETDPFD | SIVtal | HIV-1 | HIV-1 |
| 73 | MSSKEELRTTPISDPFQEEGRGPRTACNNC YCKKCCFHCYACFLRKGLGITYHAFRTRRK KIASADRIPVPQQSISIRGRDSQTTQESQK KVEEQAKANLRISRKNLGDETRGPVGAGN | SIVtal | HIV-1 | SIVagmVer |
| 74 | MSSKEELRTTPISDPFQEEGRGPLETCNNT CYCKECCYHCQLCFLNKGLGIWYDRKGRRR RSPKKIKAHSSSASDKSISTRTRNSQPEEK QKKTLETTLGTDCGPGRSHIYIS | SIVt TABLE 1-continued Exemplary Tat derivative polypeptides

| SEQ ID NO. | Amino Acid Sequence | Source TF domain* | cysteine-rich domain† | C-terminal domain |
|---|---|---|---|---|
| | QSRQDHQNPVPKQPLPTTRGNPTNPKESKK EVASKTETNQCD | | | |
| 84 | *MNADSIDPFAGNKTP*<u>RKTACTTCYCKKCCF HCQVCF</u>TRKGLGISYGRKKRRQRRRAPQDS QTHQASLSKQPASQSRGDPTGPTESKKKVE RETETDPFD | SIVden | HIV-1 | HIV-1 |
| 85 | *MNADSIDPFAGNKTP*<u>RTACNNCYCKKCCFH CYACF</u>LRKGLGITYHAFRTRRKKIASADRI PVPQQSISIRGRDSQTTQESQKKVEEQAKA NLRISRKNLGDETRGPVGAGN | SIVden | HIV-1 | SIVagmVer |
| 86 | *MNADSIDPFAGNKTP*<u>LETCNNTCYCKECCY HCQLCF</u>LNKGLGIWYDRKGRRRRSPKKIKA HSSSASDKSISTRTRNSQPEEKQKKTLETT LGTDCGPGRSHIYIS | SIVden | HIV-2 | HIV-2 |
| 87 | *MNADSIDPFAGNKTP*<u>TTACSKCYCKMCCWH CQLCF</u>LNKGLGISYGRKKRKRRRGTPQSRQ DHQNPVPKQPLPTTRGNPTNPKESKKEVAS KTETNQCD | SIVden | HIV-1 | HIV-1 |
| 88 | *MDPKGEEDQDVSHQDLIKQYRKP*<u>RTACNNC YCKKCCFHCYACF</u>LRKGLFLQKGLGISYRS YSKKKTKPDTTTAASRBLGRVTLSLYLSRTT STTWKRDSKTAKKE | SIVagmVer | HIV-1 | SIVwrc |
| 89 | *MDPKGEEDQDVSHQDLIKQYRKP*<u>ACYCRIP ACIAGERRYGTCIYQGRLWAFCCF</u>LRKGLG ITYHAFRTRRKKIASADRIPVPQQSISIRG RDSQTTQESQKKVEEQAKANLRISRKNLGD ETRGPVGAGN | SIVagmVer | HAD1 αdefensin | SIVagmVer |
| 90 | *MDPKGEEDQDVSHQDLIKQYRKP*<u>TCLKSGA ICHPVFCPRRYKQIGTCGLPGTKCCF</u>LRKG LGITYHAFRTRRKKIASADRIPVPQQSISI RGRDSQTTQESQKKVEEQAKANLRISRKNL GDETRGPVGAGN | SIVagmVer | HBD2 βdefensin | SIVagmVer |
| 91 | *MDPKGEEDQDVSHQDLIKQYRKP*<u>RTACNNC YCKKCCFHCYACF</u>TKKGLGISYGRKKRRRP ARTADKDQDNQDPVSKQSLAGTRSQQE | SIVagmVer | HIV-1 | SIVgor |
| 92 | *MDPKGEEDQDVSHQDLIKQYRKP*<u>RTACNNC YCKKCCFHCYACF</u>TKKALGISYGRKRRGRK SAGDNKTHQDPVRQQSLPKRSRIQSSQEES QKEVETEAGSGGRPRPEDSSASSGRTSGTS SSGSTRPVSTSSGCWGPYSKP | SIVagmVer | HIV-1 | SIVcpzPts |
| 93 | *MDPKGEEDQDVSHQDLIKQYRKP*<u>RTACNNC YCKKCCFHCYACF</u>LTKGLGISYGRKRKRRR ATSPVPGLSSSKNPARKQGRDTLFFLLRSL SHPTRDSQRPTEQAQAVATAATPDRQH | SIVagmVer | HIV-1 | SIVmon |
| 94 | *METPLREQENSLKSSNGRSSCTSEAAAPTL ESANLEEEILSQLYRP*<u>LETCNNTCYCKECC YHCQLCF</u>LNKGLGIWYDRKGRRRRSPKKIK AHSSSASDKSISTRTRNSQPEEKQKKTLET TLGTDCGPGRSHIYIS | SIVmne | HIV-2 | HIV-2 |
| 95 | *MDPKGEEDQDVSHQDLIKQYRKP*<u>RTACNNC YCKKCCFHCYACF</u>FMKKGLGISYGRKKRRQ RRGASKSNQNHQDSIPEQPFSQSRGDQSSP EKQEKKVESKTTSDPFGC | SIVagmVer | HIV-1 | SIVcpzPtt |

*TF region is italicized
†Cysteine-rich region is underlined

TABLE 2

SIV strain abbreviations useful in Tat derivative peptides

| SIV host designation | SIV Host Species | Latin designation |
|---|---|---|
| SIVagmVer | (African Green Monkey) Vervet | *Chlorocebus pygetythrus* |
| SIVagmGri | (African Green Monkey) Grivet | *Chlorocebus aethiops* |
| SIVagmTan | (African Green Monkey) *Tantalus* | *Chlorocebus tantalus* |
| SIVagmSab | (African Green Monkey) *Sabeus* | *Chlorocebus sabaeus* |
| SIVrcm | Red-capped Mangabey | *Cercocebus torquatus torquatus* |
| SIVsyk | Sykes Monkey | *Cercopithecus albogularis* |
| SIVagi | Agile Mangabey | *Cercocebus agilis* |
| SIVsun | Sun-tailed Monkey | *Cercopithecus solatus* |
| SIVlho | L'Hoests Monkey | *Cercopithecus lhoesti* |
| SIVstm | Stump-tail Macaque | *Macaca arctoides* |
| SIVmac | Macaque | *Macaca mulatta* |
| SIVsmm | Sooty mangabey monkey | *Cercocebus atys atys* |
| SIVmnd | Mandrill | *Mandrillus sphinx* |
| SIVdrl | Drill Monkey | *Mandrillus leucophaeus* |
| SIVtal | Talapoin Monkey | *Miopithecus talapoin* |
| SIVmus | Mustached Monkey | *Cercopithecus cephus* |
| SIVdeb | De Brazza's Monkey | *Cercopithecus neglectus* |
| SIVden | Dent's Monkey | *Cercopithecus denti* |
| SIVmon | Mona Monkey | *Cercopithecus mona* |
| SIVgor | Gorilla | *Gorilla gorilla* |
| SIVwrc | Western Red Colobus | *Procolobus verus* |
| SIVcpzPtt | *Pan Troglodytes Troglodytes* | *Pan troglodytes troglodytes* |
| SIVcpzPts | *Pan Troglodytes Schweinfurthi* | *Pan troglodytes schweinfurthii* |
| SIVmne | Pig-tail Macaque | *Macaca nemestrina* |
| SIVasc | Red-tailed Guenon | *Cercopithecus ascanius schmidti* |
| SIVbab | Yellow Baboon | *Papio* spp. |
| SIVblc | Bioko Black Colobus Monkey | *Cercopithecus satanas satanas* |
| SIVbkm | Black Mangabey | *Lophocebus aterrimus* |
| SIVblu | Blue Monkey | *Cercopithecus mitis* |
| SIVcol | Colobus Monkey | *Colobus guereza* |
| SIVolc | Oilye Colobus Monkey | *procolobus verus* |
| SIVgsn | Greater Spot-nosed Monkey | *Cercopithecus nictitans* |
| SIVkrc | Kibale Red Colobus Moneky | *Procolobus [Piliocolobus] rufomitratus tephrosceles* |
| SIVpat | Patas Monkey | *Erythrocebus patas* |
| SIVpre | Preussis Monkey | *Cercopithecus preussi* |
| SIVreg | Red-eared Guenon | *Cercopithecus erythrotis erythrotis* |
| SIVtrc | Tshuapa Red Colobus | *Piliocolobus tholloni* |
| SIVwcm | White-crowned Mangabey | *Cercocebus torquatus lunulatus* |
| SIVwol | Wolf's Monkey | *Cercopithecus woffi* |

In additional embodiments, disclosed herein is the use of conservatively modified variants of the Tat derivative polypeptides. The variants described herein maintain the immunostimulating activity of the parent or source Tat derivative polypeptide.

As used herein the term "conservatively modified variants" refers to variant peptides which have the same or similar biological activity of the original peptides. For example, conservative amino acid changes may be made, which, although they alter the primary sequence of the protein or peptide, do not alter its function. A conservative variant has at least one amino acid substituted by another amino acid or an amino acid analog that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative substitution can be assessed by a variety of factors, such as, e.g., the physical properties of the amino acid being substituted (Table 3) or how the original amino acid would tolerate a substitution (Table 4). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 3

Amino Acid Properties

| Property | Amino Acids |
|---|---|
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 4

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russel, Amino Acid Properties and Consequences of Substitutions, pp. 289-316, In Bioinformatics for Geneticists, (eds Michael R. Barnes, Ian C. Gray, Wiley, 2003).

In one embodiment, a Tat derivative polypeptide is a peptide disclosed in Table 1. In certain embodiments, the Tat derivative is not one of SEQ ID NOs. 2, 3 or 4. A Tat derivative polypeptide can also comprise conservative variants of a Tat derivative polypeptide. In an embodiment, a conservative variant of a Tat derivative polypeptide is a conservative variant of a Tat derivative polypeptide disclosed herein. In aspects of this embodiment, a conservative variant of a Tat derivative polypeptide can be, for example, an amino acid sequence having at least 50%, 55%, 60%, 65%, 70%, 75%, at least 80%, at least 85%, at least 90%, at least 95%, at least 97%, at least 98%, or at least 99% amino acid sequence identity to a Tat derivative polypeptide. In other aspects of this embodiment, a conservative variant of a Tat derivative polypeptide can be, for example, an amino acid sequence having at most 50%, 55%, 60%, 65%, 70%, 75%, at most 80%, at most 85%, at most 90%, at most 95%, at most 97%, at most 98%, or at most 99% amino acid sequence identity to a Tat derivative polypeptide.

Therefore, disclosed herein are amino acid sequences 85%, 90%, 95%, 98%, 99% or 100% identical to the Tat derivatives disclosed in SEQ ID NOs. 5-95.

In other aspects of this embodiment, a conservative variant of a Tat derivative polypeptide can be, for example, a Tat derivative polypeptide having 1, 2, 3, 4, 5, 6, 7, 8, 9, 10, 11, 12, 13, 14, 15, 20, 25, 30 or more conservative substitutions in the amino acid sequence of a Tat derivative polypeptide. In other aspects of this embodiment, a conservative variant of a Tat derivative polypeptide can be, for example, an amino acid sequence having at least 1, at least 2, at least 3, at least 4, at least 5, at least 6, at least 7, at least 8, at least 9, at least 10, at least 11, at least 12, at least 13, at least 14, at least 15, at least 20, or at least 25 conservative substitutions in the amino acid sequence of a Tat derivative polypeptide. In yet other aspects of this embodiment, a conservative variant of a Tat derivative polypeptide can be, for example, an amino acid sequence having at most 1, at most 2, at most 3, at most 4, at most 5, at most 6, at most 7, at most 8, at most 9, at most 10, at most 11, at most 12, at most 13, at most 14, at most 15, at most 20, at most 25, or at most 30 conservative substitutions in the amino acid sequence of a Tat derivative polypeptide.

Modifications (which do not normally alter primary sequence) include in vivo, or in vitro chemical derivatization of polypeptides, e.g., acetylation or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides disclosed herein are not limited to products of any of the specific exemplary processes listed herein.

As used herein, amino acid sequences which are substantially the same typically share more than 95% amino acid identity. It is recognized, however, that proteins (and DNA or mRNA encoding such proteins) containing less than the above-described level of identity arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad Sci. USA 89:10915 (1992). Algorithms conveniently employed for this purpose are widely available (see, for example, Needleman and Wunsch in J. Mol. Bio. 48:443 (1970).

In addition to substantially full length polypeptides, the present disclosure also provides for biologically active fragments of the Tat derivative polypeptides. The term "biologically active fragment" refers to fragments of the Tat derivative polypeptides which have immunostimulatory activity.

Furthermore, the peptides disclosed herein can self-associate into multimers, including but not limited to, dimers, trimers, and tetramers, in addition to existing in the monomer form. Multimerization of peptides can occur spontaneously or can be facilitated by subjecting the peptides to conditions conducive to multimerization. These conditions are known to persons of ordinary skill in peptide chemistry. The compositions disclosed herein can include monomers or multimers of the peptides, or a mixture of monomers and multimers.

The following expression systems are suitable for use in expressing the disclosed Tat derivatives: mammalian cell expression systems such as, but not limited to, Chinese Hamster Ovary (CHO), COS cells (fibroblast-like cells from African green monkey kidney tissue), bovine cells, murine cells, human embryonic kidney cells, or baby hamster kidney cells; insect cell expression systems such as, but not limited to, Bac-to-Bac expression system, baculovirus expression system, and DES expression systems; yeast expression systems: and *E. coli* expression systems including, but not limited to, pET, pSUMO and GST expression systems. In another embodiment, the Tat derivatives are expressed with a histadine (poly histidine) tag useful for isolation of the polypeptide. Histidine tag purification systems are known to persons of ordinary skill in the art.

"Therapeutically effective amount" is intended to qualify the amount required to achieve a therapeutic effect. As used herein, the term "therapeutically effective amount" is synonymous with "therapeutically effective dose" and when used in reference to treating cancer means the most beneficial dose of a composition disclosed herein necessary to achieve the desired therapeutic effect and includes a dose sufficient to reduce tumor size, inhibit growth of a tumor, or cause regression of a tumor.

Override of Immune Checkpoints

Immune checkpoints, such as cytotoxic T-lymphocyte antigen 4 (CTLA-4) and programmed death 1 (PD-1) expressed on tumor-specific T cells, lead to compromised activation and suppressed effector functions such as proliferation, cytokine secretion, and tumor cell lysis. Specifically modulating these receptors with immune checkpoint inhibitors is a new approach in cancer immunotherapy.

An important negative co-stimulatory signal regulating T cell activation is provided by PD-1 (also known as CD279), and its ligand binding partners PD-L1 (also known as B7-H1 and CD274) and PD-L2 (also known as B7-DC and CD273). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). Thus far, the only identified ligands for PD-1 are PD-L1 and PD-L2.

The immunosuppressive nature of the tumor microenvironment is helpful to explain the immune dysfunction that accompanies cancer progression. The PD-1/PD-L1 signaling pathway is one emerging model for immune evasion at the tumor site and represents an important checkpoint and barrier for an effective immune response.

The presence of PD-L1 in the tumor site is considered to facilitate immune evasion as a result of an active tumor-mediated process for reprogramming host cells present in the tumor microenvironment. The engagement of PD-L1 with its PD-1 receptor on the surface infiltrating T-cells may induce their programmed cell death, anergy, and exhaustion. Induction of PD-L1 in the tumor microenvironment may serve as a "molecular shield" to protect the tumor from a cell-mediated immune response.

The refractory state of cancers to immunotherapeutics may be a consequence of immunosuppression that accompanies disease progression in established cancers. The Tat derivative polypeptides disclosed herein elicit antitumor immune responses by triggering monocyte-derived dendritic cells to stimulate the CD8+ CTL and override PD-L1 immunosuppression. Thus, the PD-1/PD-L1 immunosuppressive signaling pathway may provide a potential mechanism by which breast tumors evade host tumor immunity and therefore Tat derivative polypeptides can impact solid tumor progression by induction of tumor infiltrating CD8+ CTLs in the face of PD-L1 immunosuppression.

Modulating of signaling through PD-L1, thereby preventing PD-L1 from sending a negative co-stimulatory signal to T-cells is likely to enhance immunity in response to infection (e.g., acute and chronic) and tumor immunity. In addition, the Tat derivative polypeptides disclosed herein may be combined with antagonists of other components of PD-1: PD-L1 signaling, for example, antagonist anti-PD-1 and anti-PD-L2 antibodies.

Additionally, agents that modulate immune checkpoints that can be used for immunotherapeutic treatment regimens for cancer in combination with the disclosed Tat derivative polypeptides include, but are not limited to, CTLA-4, PD-1, PD-L1, PD-L2, B7-H3, B7-H4, LAG-3, TIM-3, and GITR, and their respective ligands.

Use of Tat Derivative Polypeptides

The disclosed Tat derivatives are immune-stimulating polypeptides which are useful in many types of cancers. In one embodiment, the Tat derivatives are useful in treating a type of cancer including, but not limited to, adrenocortical carcinoma, anal cancer, appendix cancer, astrocytoma, basal-cell carcinoma, bile duct cancer, bladder cancer, bone cancer, brain cancer, breast cancer, bronchial adenomas/carcinoids, carcinoid tumor, cervical cancer, chronic myeloproliferative disorders, colon cancer, desmoplastic small round cell tumor, endometrial cancer, ependymoma, esophageal cancer, Ewing's sarcoma, germ cell tumors, eye cancer, gallbladder cancer, gastric cancer, gastrointestinal carcinoid tumor, gastrointestinal stromal tumor (GIST), gestational trophoblastic tumor, glioma, gastric carcinoid, head and neck cancer, heart cancer, hepatocellular cancer, Hodgkin's lymphoma, hypopharyngeal cancer, islet cell carcinoma, Kaposi sarcoma, kidney cancer, leukemias, lip and oral cavity cancer, liposarcoma, liver cancer, lung cancer, lymphomas, macroglobulinemia, medulloblastoma, melanoma, merkel cell carcinoma, mesothelioma, mouth cancer, multiple myeloma/plasma cell neoplasm, mycosis fungoides, nasal cavity and paranasal sinus cancer, nasopharyngeal carcinoma, neuroblastoma, oral cancer, oropharyngeal cancer, ovarian cancer, ovarian epithelial cancer, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, prostate cancer, rectal cancer, renal cell carcinoma, retinoblastoma, rhabdomyosarcoma, salivary gland cancer, sarcoma, Sézary syndrome, skin cancer, squamous cell carcinoma, stomach cancer, testicular cancer, throat cancer, thymoma, thyroid cancer, urethral cancer, uterine cancer, uterine sarcoma, vaginal cancer, vulvar cancer, Waldenström macroglobulinemia, and Wilms tumor.

In another embodiment, the cancer is breast cancer. In yet another embodiment, the cancer is ovarian cancer. In yet another embodiment, the cancer is prostate cancer. In yet another embodiment, the cancer is lung cancer. In yet another embodiment, the cancer is malignant melanoma.

While the disclosed Tat derivatives are countersuppressive agents with "stand alone" efficacy in cancer, these observations moreover support the prospect that the Tat derivatives can synergize with other countersuppressive anti-cancer therapeutics currently in clinical development that may have a restricted effect in the face of advanced tumor burden and accompanying severe immunosuppression.

Expression and presence of PD-L1 by tumors and invading immune cells may be used to predict response to therapy and/or prognosis of disease. Therefore, in one embodiment disclosed herein, a subject is selected for treatment with a Tat derivative polypeptide based on expression of PD-L1 in their tumor tissue. In certain embodiments, the tumor tissue is evaluated for PD-L1 expression before the subject is treated with any cancer therapy. In another embodiment, the tumor tissue is evaluated for PD-L1 expression before the subject is treated with a Tat derivative polypeptide disclosed herein.

Expression of PD-L1 may be determined by an immunological analysis of tumor tissue such as, but not limited to, immunohistochemistry, immunoassay (ELISA, ELISPOT, radioimmunoassay), protein microarrays, flow cytometry, quantitative immunofluorescence, and surface plasmon resonance. Non immunological assays such as quantitative polymerase chain reaction (qPCR), and determination of messenger RNA can also be used.

Thus, in some embodiments, a patient is selected for treatment with the Tat derivative polypeptide if the pre-treatment tumor contains more than 5% PD-L1-expressing cells, more than 6% PD-L1-expressing cells, more than 7% PD-L1-expressing cells, more than 8% PD-L1-expressing cells, more than 9% PD-L1-expressing cells, more than 10% PD-L1-expressing cells, more than 11% PD-L1-expressing cells, more than 12% PD-L1-expressing cells, more than 13% PD-L1-expressing cells, more than 14% PD-L1-expressing cells, more than 16% PD-L1-expressing cells, more than 18% PD-L1-expressing cells, or more than 20% PD-L1-expressing cells.

Pharmaceutical Compositions

The present disclosure is also directed to pharmaceutical compositions comprising the above-described Tat derivative polypeptides. Dosages and desired drug concentrations of the disclosed pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. In one embodiment, the disease is present. In another embodiment, the life of a cell or an individual is prolonged due to the methods described herein.

The above-described Tat derivative polypeptides can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal, intrabuccal, intravenous, subcutaneous, intramuscular and pulmonary administration can be made without undue experimentation by means well known in the art, for example with an inert diluent or with an pharmaceutically acceptable carrier. For the purpose of therapeutic administration, the pharmaceutical compositions may be incorporated with excipients and used in the form of tablets, troches, capsules, elixirs, suspensions, solutions, syrups, and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing polysorbate 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Compositions comprising such carriers are formulated by well known conventional methods.

The Tat derivative polypeptide compositions can easily be administered parenterally such as for example, by intravenous, intramuscular, intrathecal, or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The Tat derivative polypeptide compositions of the present disclosure may be administered in a therapeutically effective amount, according to an appropriate dosing regimen. As understood by a skilled artisan, the exact amount required may vary from subject to subject, depending on the subject's species, age and general condition, the severity of the infection, the particular agent(s) and the mode of administration. In some embodiments, about 0.001 mg/kg to about 50 mg/kg, of the composition based on the subject's body weight is administered, one or more times a day, to obtain the desired therapeutic effect. In other embodiments, about 1 mg/kg to about 25 mg/kg, of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately.

In another embodiment, repetitive, or frequent, dosing of the disclosed Tat derivatives is contemplated that could run ahead of tachyphylaxis, as well as reverse the immunosuppressive tide established during cancer progression. Frequent dosing is one procedure used for example in allergy therapy that can support immunological tolerance to an agent. Once the Tat derivative can be used to regain immunoreactivity to a tumor, then other immunotherapeutics that have lost benefit due to advanced disease could potentially regain efficacy. In a second protocol, chemotherapeutic regimens are used that could release a shower of tumor antigens in alternation with Tat derivative immunotherapy. As advanced stage human cancers are often multiply drug resistant, radiotherapy could be a practical alternative in human trials.

The number of repeated doses of the Tat derivative polypeptides can be established by the medical professional based on the response of the patient to the doses. In one embodiment, the Tat derivative polypeptides is administered once every three days for 3 doses in a ten day period. This administration scheme is then repeated for a plurality of cycles. The present disclosure envisions a variety of different administration schemes wherein the Tat derivative polypeptides is administered multiple times within a selected time frame and then the administration scheme is repeated for a plurality of cycles. In another embodiment, administration of the Tat derivative polypeptides can be alternated with administration of one or more other anti-cancer, immunomodulatory, or immunosuppressive agents. In one embodiment, the immunosuppressive agent is cyclophosphamide.

Furthermore, treatment with the Tat derivative polypeptides can be combined with other cancer therapies such as surgery, radiation therapy, or chemotherapy. Chemotherapeutic agents include alkylating agents such nitrogen mustards, nitrosoureas, tetrazines, aziridines, cisplatins, and derivatives; anti-metabolites such as anti-folates, fluoropyrimidines, deoxynucleoside analogues, and thiopurines; antimicrotubule agents such as vinca alkaloids and taxanes; topoisomerase inhibitors such as camptothecin, irinotecan, topotecan, novobiocin, merbarone, and aclarubicin; cytotoxic antibiotics such as anthracyclines, actinomycin, bleomycin, plicamycin, and mitomycin.

Effects of Tat Derivative Polypeptides in Breast Cancer

Animal trials with recombinantly-produced Tat protein derivatives in three different widely accepted murine models of breast cancer, 4T1, SM1, and TS/A, provided support that Tat derivatives are active in suppressing primary breast cancer growth in mice. Moreover, one derivative, Nani-P2, significantly inhibited the development of spontaneous 4T1 lung metastases and increased survival compared with control mice. Significantly, increased levels of IFN-γ production accompanied treatment of murine breast cancers with Tat derivatives. In studies when 4T1 breast cancers were seeded for fourteen days prior to the initiation of treatment, the Tat derivatives were equally as effective as when given at the time of tumor implantation when assessed by primary tumor growth, survival, and reduction in metastatic lung burden when compared to PBS-treated controls.

Synthetic Tat derivatives are immunostimulatory to APCs, have substantial activity against primary as well as established cancers in three widely-used murine mammary carcinoma models. In particular, one of the derivatives, Nani-P2, produced a dose- and route-dependant impact on primary tumor growth, lung metastasis formation, and survival in the aggressive Her2(−) 4T1 breast cancer model. Decreased lung metastases correlate with improved survival, because lung metastasis is the leading cause of mortality in advanced breast cancer. Importantly, mice bearing established 4T1 breast tumors treated intravenously with Nani-P2 protein had highly significant tumor growth inhibition and survival benefits that extended out at least 36 days past the last dosing. In limited cases, total remissions were apparently observed that were more frequent with the less aggressive (SM1) and/or somewhat more immunogenic (TS/A) breast tumors. Delaying the administration of Nani-P2 post tumor implant had little negative effect on 4T1 tumor growth suppression, insofar as therapy (SC) initiated on day 0 after tumor cell injection shrank tumor burden on average 53%, while SC therapy begun on day 13, when tumor growth already averaged about 5 mm in diameter, decreased tumor burden on average 52% at its maximal effect. Taken together, these observations indicated that the Tat derivatives can favorably impact advanced and Her2(−) human breast cancers in humans.

The studies reported here used a protocol of three or four approximately weekly doses of Tat derivative given either IV or SC, with IV administration proving most efficacious for increasing survival and for reducing metastases. No toxicity was observed in over 250 mice given these compositions. The sensitivity of breast cancer to the Tat derivatives contrasts favorably when compared to the dose response curve of HERCEPTIN® (Genentech), where 4-8 mg/kg is standard therapy. It is estimated that Tat derivatives will be up to 100-fold more bioactive in humans than mice, meaning that even lower doses associated with even less risk of toxicity could likely prove successful.

Figure 5A:
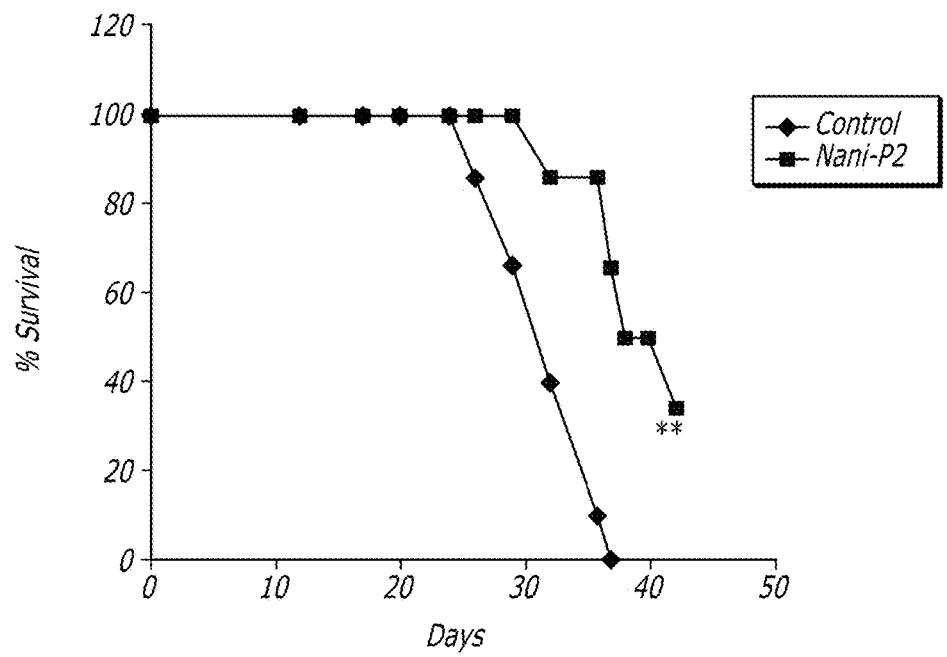
FIGS. 5A and 5B depict a Kaplan-Meier survival curve of Nani-P2 treatment of mice bearing 4T1 breast tumors. Mice were injected SC with $1 \times 10^4$ 4 T1 cells in the mammary pad at day 0. Treatment was started at day 0 with four doses of Nani-P2 (40 ng) administered SC. At day 42, the treatment group had statistically significant better survival over controls () (FIG. 5A). In one group, therapy was delayed until day 13, at which time a series of three doses of Nani-P2 (40 ng) were administered weekly either intravenous (IV), SC into the draining lymph nodes, or intratumoral (IT) (FIG. 5B). The survival benefit of IV Nani-P2 was highly statistically significant at day 47 (), while the survival benefit of SC Nani-P2 was also statistically significant (*).

Established herein is that the Tat derivatives activate the INF-γ arm of the anti-cancer T cell immune response (FIG. 5). Baseline levels of INF-γ secreted by splenocytes from mice treated with Nani-P2 are 8-fold higher than that from control mice treated with PBS. IFN-γ secretion in response to Tat derivative treatment in vivo could be additionally augmented (up to 53x) in vitro by innate immune agonists GM-CSF and IL-4, while splenocytes from control mice remain suppressed even after attempts to co-stimulate with high-dose GM-CSF and/or IL4.

A more immunogenic breast cancer model (SM1) and/or a breast tumor with an immunodominant epitope (TS/A) have a relatively high regression rate after Tat derivative therapy, while the "non-immunogenic" 4T1 model is more refractory. This is consistent with a model that immune suppression is a dominant factor in breast cancer progression, and in fact may be contributory to breast cancer invasiveness. This model is supported by the observation that 4T1 expresses several common breast cancer antigens, including lactadherin and androgen binding protein, at high levels against which the immune response is apparently fully suppressed absent Tat derivative-induced countersuppression.

Example 1

In Vitro Activity of Tat Derivatives

Figure 2:
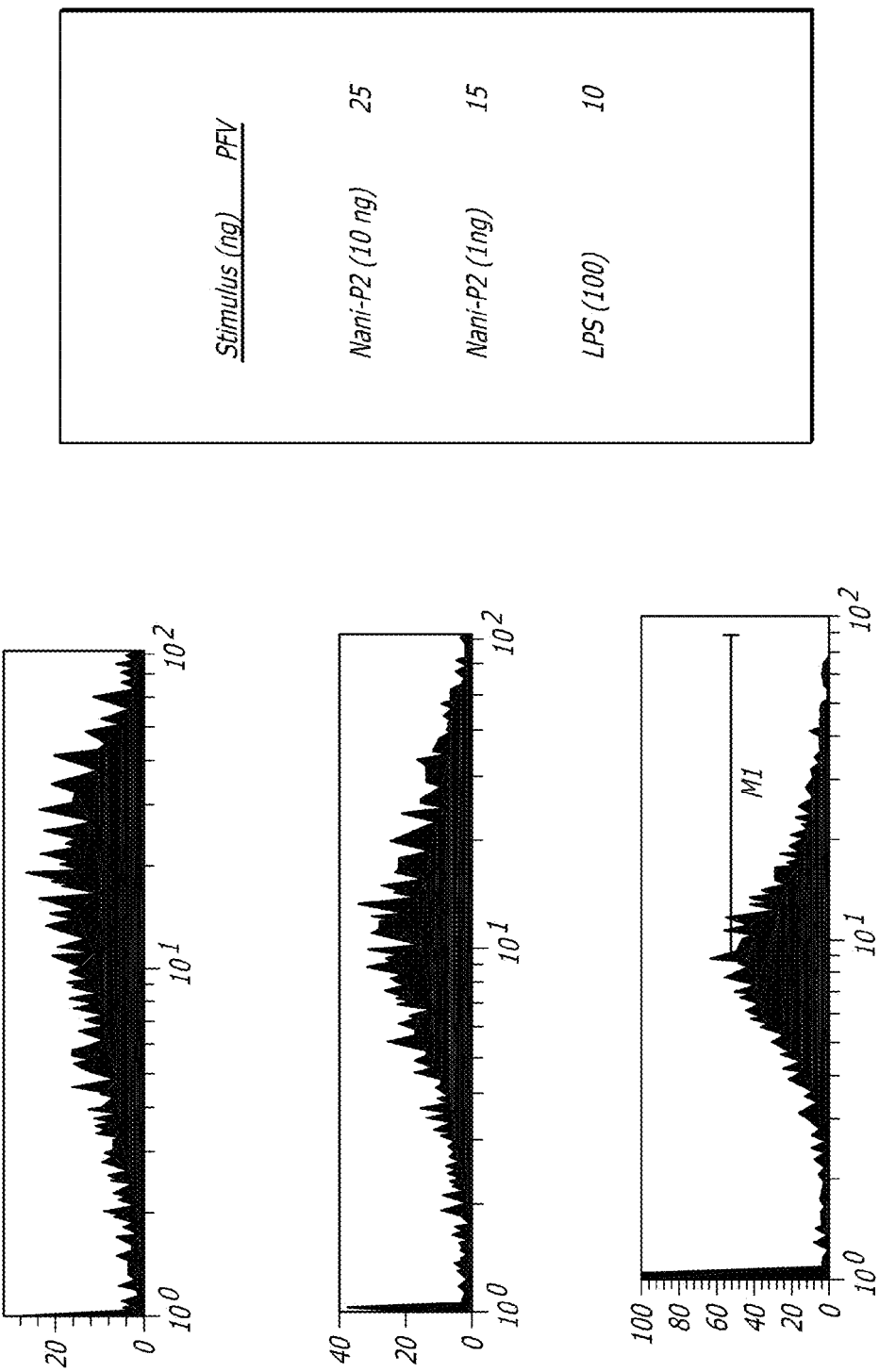
FIG. 2 depicts a dose-response curve of stimulation of human monocytes with Tat derivatives.

Human monocytes were cultured for 24-48 hours with a Tat derivative (Nani-P2), an immunostimulatory sequence (ISS) of a toll-like receptor (TLR) (FIG. 1), or lipopolysaccharide (LPS) (FIG. 2) and the cells were then washed and stained with fluorescent-labeled CD86. The Tat derivative stimulated higher expression of CD86 than either ISS (TLR) or LPS.

Example 2

Evaluation of Tat Derivatives in Mouse Models of Breast Cancer

Materials and Methods

Animals.

Female BALB/c mice 6 to 8 weeks old were purchased from the Jackson Laboratory (Bar Harbor, Nebr.). Mice were acclimated for at least 1 week before use. Mice were kept in pathogen-free conditions at the Animal Maintenance Facility of the Columbia University of Medical Center and all experiments were approved by the Institutional Animal Care and Use Committee of Columbia University of Medical Center.

Cell Lines.

4T1 cells, a 6-thioguanine-resistant cell line derived from a BALB/c spontaneous mammary carcinoma was obtained from ATCC; TS/A, a murine adenocarcinoma cell line was provided by Dr. Sandra Demaria (Demaria S. et al. Clin Cancer Res. 11:728-34, 2005); and SM1, the BALB/C-derived mammary carcinoma was kindly was provided by Dr. James Allison, University of California, Berkeley. All tumor cell lines were cultured in DMEM, supplemented with 2 mM L-glutamine, 10 mM HEPES, 150 units/ml penicillin/streptomycin, 10% heat-inactivated FCS (Invitrogen), 50 µM 2-mercaptoethanol (Sigma), and 50 mg/L gentamicin (Lanza).

Tumor Challenge and Treatment.

BALB/c mice were injected (SC) with $1\times10^4$ 4 T1, $1\times10^5$ TS/A or $2\times10^5$ SM1 cells, respectively, in the left mammary pad on day 0. Immunotherapy was performed by directly injecting a Tat derivative into the right flank at 0, 7, 12, and 17 days after establishment of tumors. The control group received PBS injection. In some experiments, when all of the mice had an established measurable tumor (3-5 mm diameter at 14 days after tumor injection), the animals were randomly assigned to various treatment groups as indicated. Tumor burden (tumor volume) was measured and recorded three times weekly. Animals were sacrificed when tumors reached a volume of 15 mm in diameter and the tumors harvested and weighed.

Detection of Lung Metastases.

Lungs were examined for 4T1 metastases as previously described (Pulaski B. et al. Cancer Res. 60:2710-2715, 2000). Primary 4T1 tumors that have been established for 2-3 weeks in BALB/c mice metastasize to the lungs in a very large majority of animals. Briefly, mice were sacrificed according to IACUC guidelines established at the start of the trials, the lungs were removed, and tumor nodules on the surface of the lungs were enumerated with the naked eye by two independent investigators blinded to the treatment protocols.

ELISA Analysis of IFN-γ Production by Immune Spleen Cells.

Splenocyte secretion of IFN-γ was assessed by an OptEIA™ ELISA kit (BD Biosciences). Briefly, spleen cells ($1\times10^5$/well) from 4T1 tumor-bearing mice were cultured with or without $5\times10^3$/well mitomycin C (50 µg/ml)-treated 4T1 cells (used to provide tumor antigens) in DMEM at a 20:1 E:T (effector:tumor) ratio with IL-2 (50 ng/mL) and GM-CSF (100 ng/ml) in 96-well plates. Supernatants were collected after 72 hr and kept frozen at −80° C. until analysis without loss of activity. IFN-γ was measured in cell-free supernatants of duplicate wells by ELISA according to the manufacturer's instructions. Tumor-specific IFN-γ production was calculated by subtracting the background values measured in supernatants of spleen cells cultured with medium alone and optical density (OD) values were converted to pg/ml amounts of IFN-γ using a recombinant IFN-γ standard curve. Stimulation index (SI) was calculated as the ratio of IFN-γ in stimulated versus control cultures.

Statistical Analysis.

Data were statistically analyzed using Student's t-test (Graph Pad Prism version 5; GraphPad). Data from animal survival experiments were statistically analyzed using log-rank test (Graph Pad Prism version 5).

Results

The therapeutic effect of systemic administration of synthetic, Tat-derived compositions in murine models of breast cancer was investigated. To compare the relative protection conferred by a small panel of different derivatives against primary breast tumor growth, female BALB/c mice were injected with $1\times10^4$ 4 T1 breast tumor cells SC into the mammary pad, and then treated with 400 ng partially-purified Tat derivatives at day 0, 7, 14, and 21 (SC injection in PBS) into the draining axillary lymph nodes.

Figure 3A:
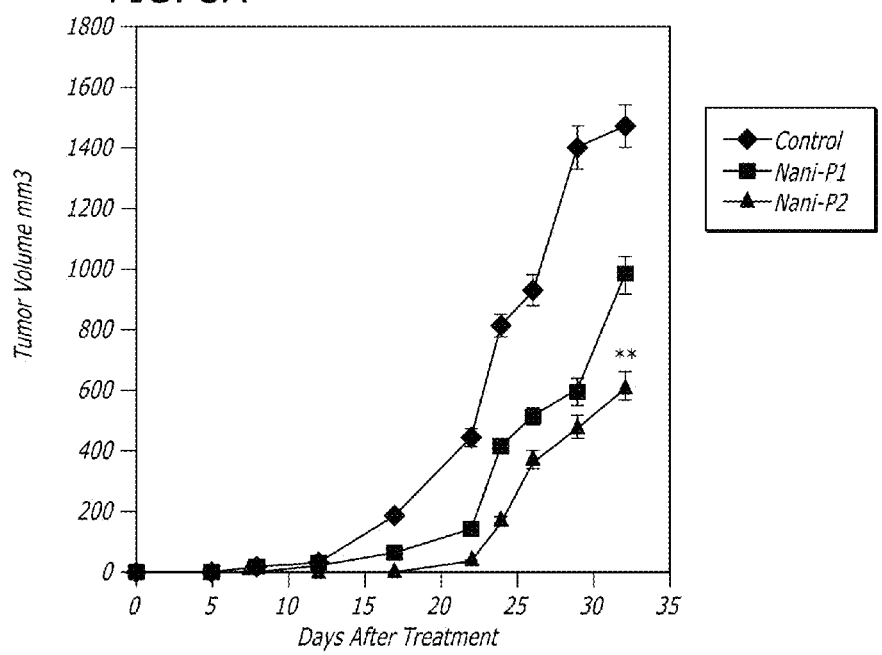
FIGS. 3A and 3B depict the effect of therapy with Tat derivatives on 4T1 tumor growth in vitro. BALB/c mice injected with $1 \times 10^4$ 4 T1 tumor cells were treated with Nani-P1 or Nani-P2 (400 ng, subcutaneous [SC]) (FIG. 3A) or Nani-P3 (400 ng or 2 μg, SC) (FIG. 3B) on days 0, 7, 14 and 21 after injection of tumor cells. The control group was treated with PBS. Data represents mean tumor volume; bars±SE. Each group contained 10 mice. From day 15, the differences between the control group and groups treated with Nani-P1 or Nani-P2 were significant ($p<0.05$). The differences between control and Nani-P2 or Nani-P2 was highly significant starting at day 22 ($p<0.01$). There was no difference between Nani-P3 (either dose) and controls.
Figure 3B:
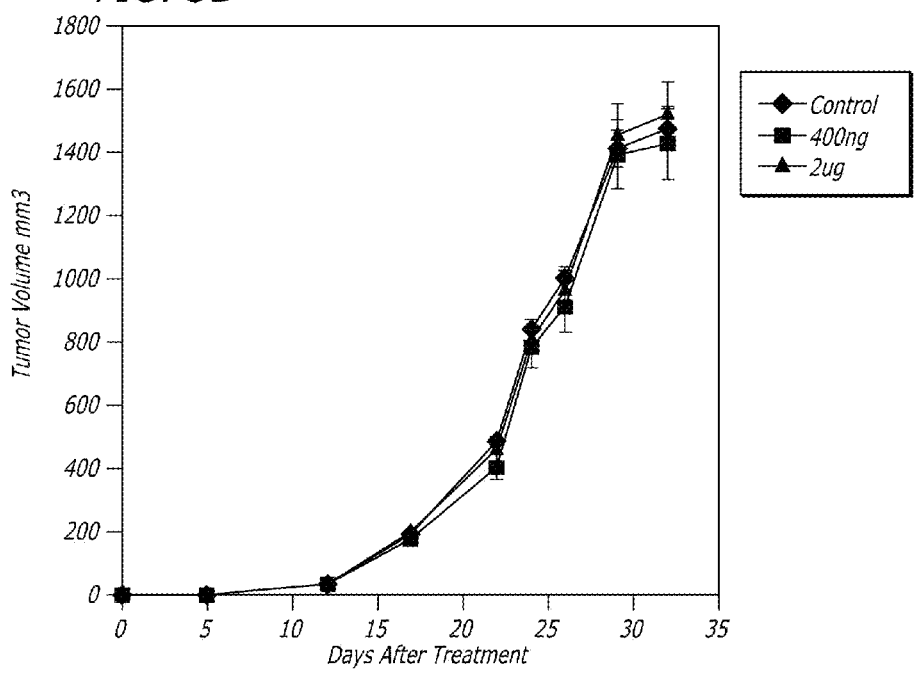

Two of the derivatives, Nani-P1 and Nani-P2, significantly reduced tumor burden when compared to control mice receiving PBS injections alone, with this difference first becoming apparent at 15 days after tumor implantation (FIG. 3A, day 15 p<0.05). By contrast a third derivative, Nani-P3, produced and partially purified with the same protocol as the others, was less effective at suppressing 4T1 primary tumor growth even at five-fold higher doses (2 µg, FIG. 3B) or for extending survival (not shown). These results effectively ruled out that contaminants in preparation contributed to anti-tumor efficacy, particularly insofar as subsequent trials were performed with highly purified (>95% pure) materials at much lower doses. The efficacy of Nani-P2 was significantly more sustained than Nani-P1, so that at day 21 (the final dosing), the difference in primary tumor burden between Nani-P2 and Nani-P1-treated tumors became 18 mm$^3$ and was highly statistically significant (p<0.01). This effect persisted throughout the remainder of this trial despite no further therapy.

Figure 4:
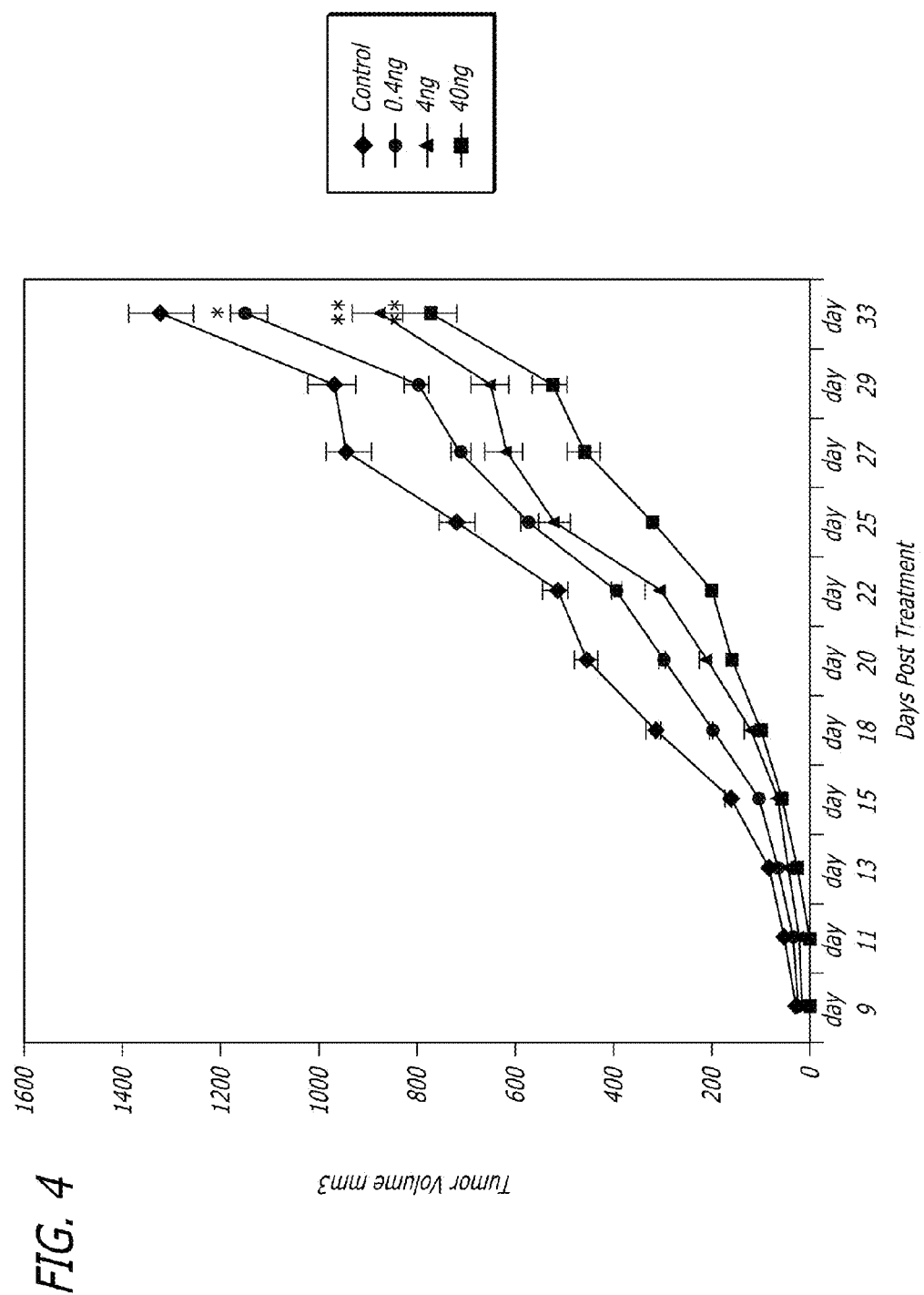
FIG. 4 depicts a dose response curve for the effects of purified Nani-P2 on 4T1 breast tumor growth in vivo. Four groups of ten BALB/c mice each were implanted with $1 \times 10^4$ 4 T1 cells. Three groups were given escalating doses of 0.4 ng, 4 ng, and 40 ng per mouse, respectively, in the left flank four times over 21 days. The fourth, control group was injected in the left flank with PBS. Data represent mean tumor volume. The differences between the control group and 0.4 ng dose was significant ($p<0.5*$), and the difference between control and 4 ng or 40 ng Nani-P2 treated groups was highly significant ($p<0.1$, $p<0.01$).

The breast tumor growth inhibitory effect of highly-purified Nani-P2 on 4T1 tumors was dose-dependent, with significant effects apparent following the SC administration of as little as 0.4 ng of compound (FIG. 4). Increasing the dose of Nani-P2, administered SC in the draining axillary flank, by logarithmic increments from 0.4 ng to 40 ng per dose progressively inhibited 4T1 breast tumor growth. The more robust 4T1 growth inhibition at higher doses of Nani-P2 between 0.4 ng to 40 ng was statistically significant ($p<0.01$), while increasing the dose to 400 ng and even 2 µg resulted in no further anti-tumor efficacy (data not shown). Importantly, no toxicity was observed following the SC or IV administration of 40 ng of Nani-P2 in multiple trials using multiple dosing schedules. A dose of 40 ng Nani-P2 was selected for further study.

To determine whether Nani-P2 treatment could extend survival in addition to shrinking primary tumors in mice, treatment protocols using various dosing schedules and routes (SC, IV or IT) of administration of 40 ng Nani-P2 were performed. Cohorts of ten mice per group were followed for length of survival, as assessed by use of the Kaplan-Meier product limit method. As per Columbia University Medical Center Animal Facility regulations, each mouse was euthanized at a mean tumor diameter of approximately 15 mm, or earlier if the mouse became moribund, making one of these two outcomes the defining criteria for fatality.

In the first trial evaluating Nani-P2, SC treatment was initiated simultaneously to tumor implant. The median survival time for control (PBS treated) mice was 30 days and 100% fatality occurred by day 36. With Nani-P2 administration (4 doses over 21 days), 35% of treated mice were still alive at day 48 ($p<0.001$, FIG. 5A) at which point all of the mice were sacrificed due to primary tumor burden.

Figure 5B:
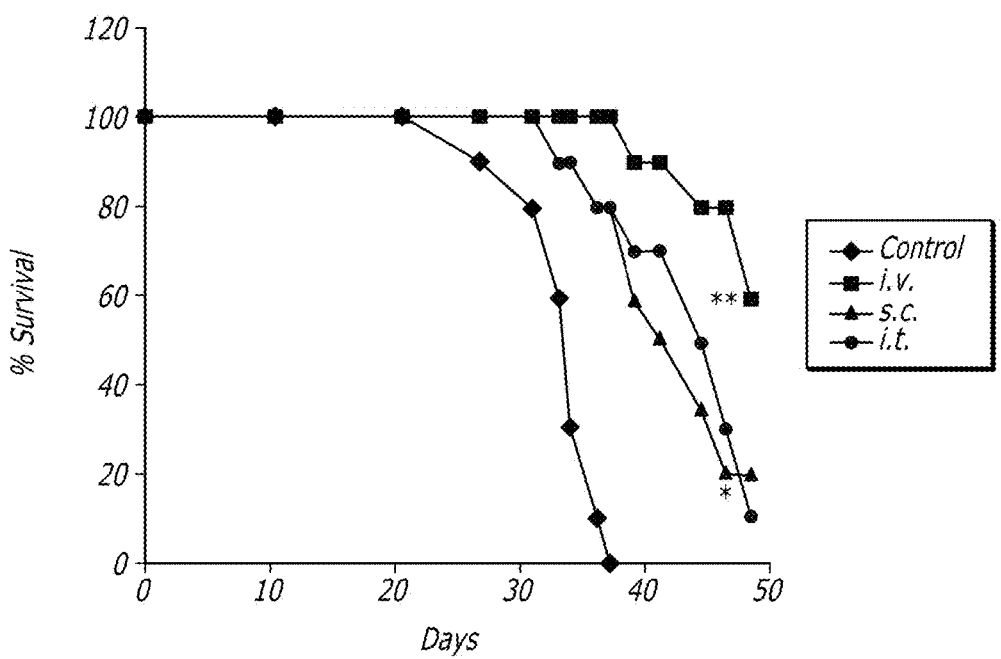

In a second survival trial, the tumors were allowed to become established for fourteen days to better assess efficacy in metastatic disease, after which three cycles of Nani-P2 therapy were administered weekly by one of several routes (SC, IV or IT) to compare relative efficacy for each route of dosing (FIG. 5B). Similar to the previous trial, median survival of control (PBS-treated SC) mice was 32 days, with 100% fatality by day 36. Survival was extended by the IV administration of Nani-P2 ($p<0.005$, FIG. 5B) with 60% survival at day 47, compared with 20% survival of SC treated mice at day 47 ($p<0.05$). Intratumoral administration of compound was slightly inferior to SC administration.

Figure 6A:
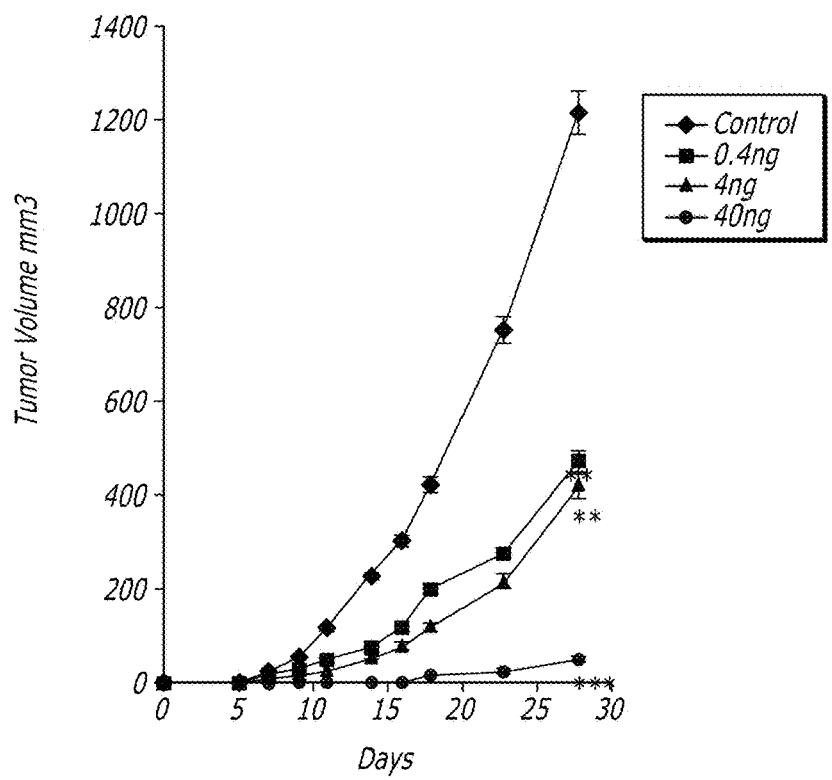
FIGS. 6A and 6B depict the anti-tumor activity of Nani-P2 in TS/A and SM1 breast carcinoma models. Mice were implanted SC with $1 \times 10^5$ TS/A breast cancer cells (FIG. 6A) and treated with escalating doses of SC Nani-P2 (0.4, 4, and 40 ng). Even at the lowest dose, the primary anti-cancer difference was highly significant (p<0.01), while the 40 ng dose was also highly significant (p<0.01*).
Figure 6B:
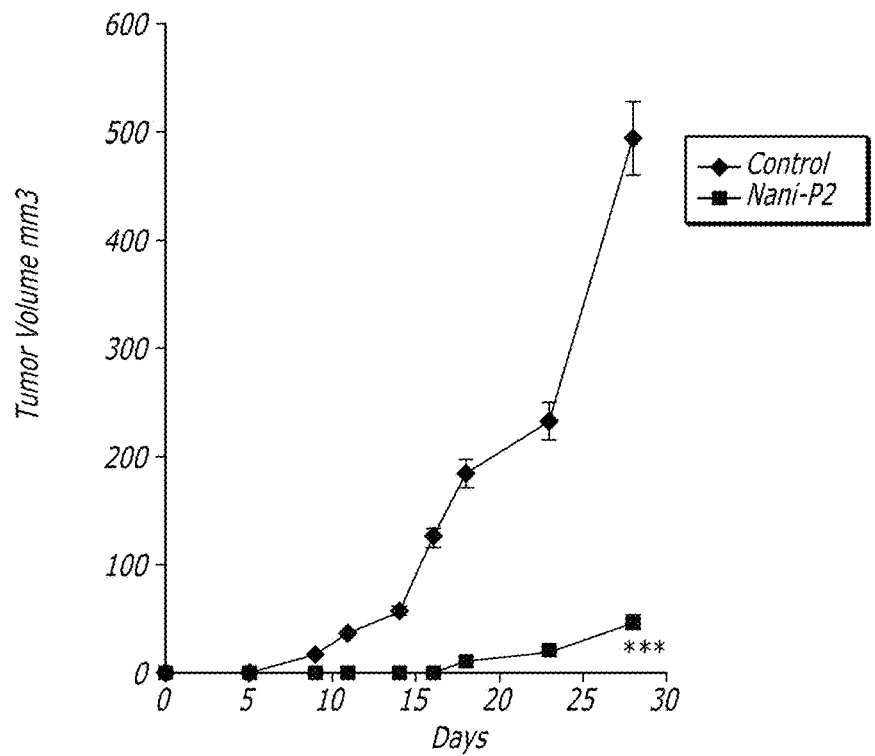

The 4T1 murine mammary tumor model was chosen for study because it is an aggressive and rapidly invasive tumor; it is routinely metastatic at fourteen days post-implant by which time it is difficult to treat. To learn whether the efficacy of Nani-P2 could extend to other murine breast tumor models, two additional mammary tumors, TS/A and SM1 were studied (FIG. 6). TS/A primary tumors were approximately as aggressive as 4T1, reaching a tumor volume of 15 mm at 30 days (FIG. 6A). However, the TS/A tumors were considerably more responsive to Nani-P2 treatment, with an approximate 50% suppression of growth after treatment with 0.4 ng Nani-P2, and a 40% total remission rate at 30 days.

The SM1 mammary carcinoma model (FIG. 6B) is initially less aggressive as a primary tumor, and deaths appear to be through mechanisms other than metastatic disease. By day 30 of treatment, SM1 tumors reached a mean volume approximately 33% smaller than either TS/A or 4T1. This indicated a heightened sensitivity of the SM1 tumor to Nani-P2 immunotherapy as compared to 4T1, such that tumor growth was suppressed in 100% of animals for 16 days, and 40% of animals remained in remission even at 28 days following implant and fully one week after termination of the regimen.

Figure 7:
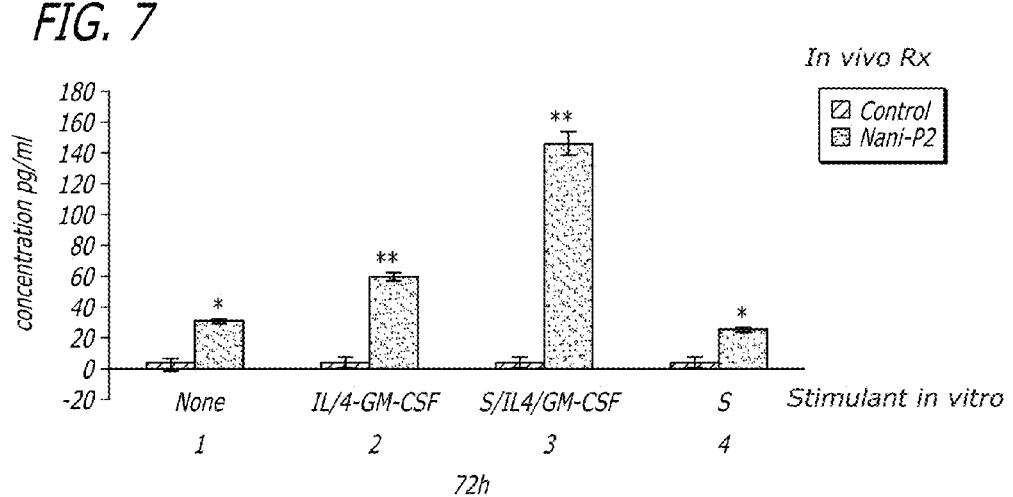
FIG. 7 depicts INF-γ production from spleen cells of mice bearing 4T1 breast tumors. BALB/c mice were injected SC with $1 \times 10^4$ 4 T1 cells. Control animals received weekly injections of PBS, while the Nani-P2 treatment comprised once weekly SC injections (40 ng) initiated at day 0 and continued for 4 weeks. On day 33, when control mice were at end stage, the mice were sacrificed, the spleens harvested and frozen as single cell suspensions until time of assay. Spleen cells ($2 \times 10^5$) and $1 \times 10^4$ mitomycin C-treated (50 μg/ml for 30 min) 4T1 stimulator cells (S) were plated into 96-well plates. After 72 hr of stimulation, the supernatants were collected, and IFN-γ concentration was determined using a commercial IFN-γ ELISA kit. IFN-γ production was significantly (p<0.05*) higher in cultures of spleen cells from Nani-P2-treated mice under all conditions of in vitro culture. 1: no restimulation; 2: IL-4 (50 ng/ml)/GM-CSF (100 mg/ml); 3: stimulator cells/IL-4/GM-CSF; 4: stimulator cells only. Addition of in vitro agonists IL-4 and GM-CSF (2 and 3) induced highly significant increases in IFN-γ production (p<0.01**).

To determine whether cytotoxic T-lymphocytes play a role in tumor rejection induced by Nani-P2 therapy, an IFN-γ ELISA assay (FIG. 7) was performed to compare spleen cells of 4T1 tumor-bearing mice treated either without (Control) or with Nani-P2 (FIG. 7). Spleens were removed under sterile conditions and prepared as described elsewhere (duPre'S. et al. Exp. Mol. Path. 85:174-188, 2008). Briefly, spleens were homogenized and splenocytes, as a rich source of systemic cytolytic T cells and APCs, were co-cultured with mitomycin C-treated 4T1 stimulator cells to induce recall immune responses. Control wells were cultured with medium alone.

IFN-γ concentrations, a standard surrogate for CTL activation, were quantitated by commercial ELISA (BD Biosciences). IFN-γ production was significantly higher ($p<0.01**$) in cultures of spleen cells taken from Nani-P2-treated BALB/c mice under all conditions of assay. IFN-γ activity in Nani-P2-treated, but not in control, animals could be enhanced by the addition of IL-4 and GM-CSF ($p<0.05$) under conditions shown to promote DC differentiation, and could be even further augmented if tumor stimulators were added back at the initiation of culture (stimulation index=53 vs control, 3S+IL4+GM-CSF) demonstrating the potency of Nani-P2 in synergy with other CTL agonists.

Figure 8A:
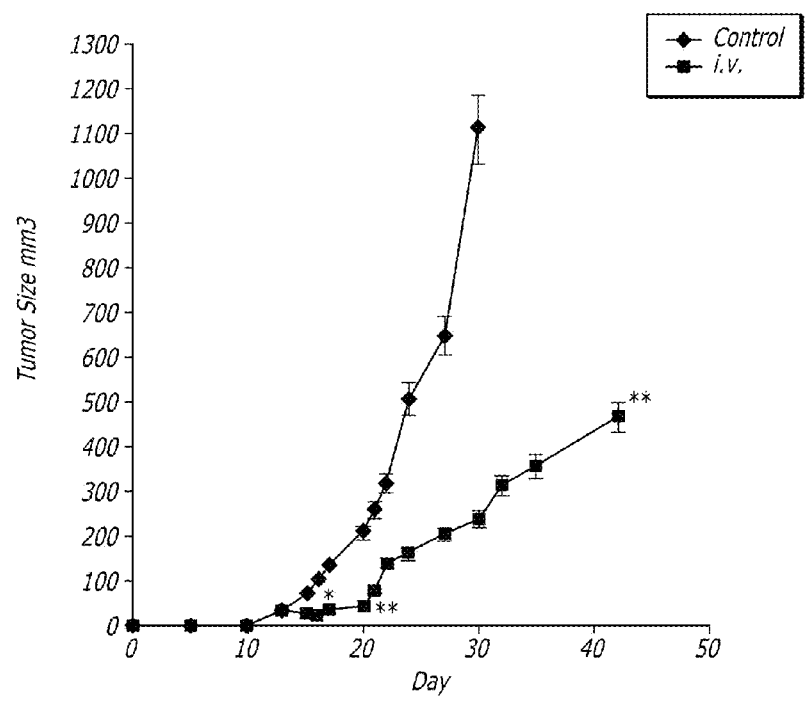
FIGS. 8A and 8B depict regression of established 4T1 breast tumors and inhibition of lung metastasis by Nani-P2 treatment.
Figure 8B:
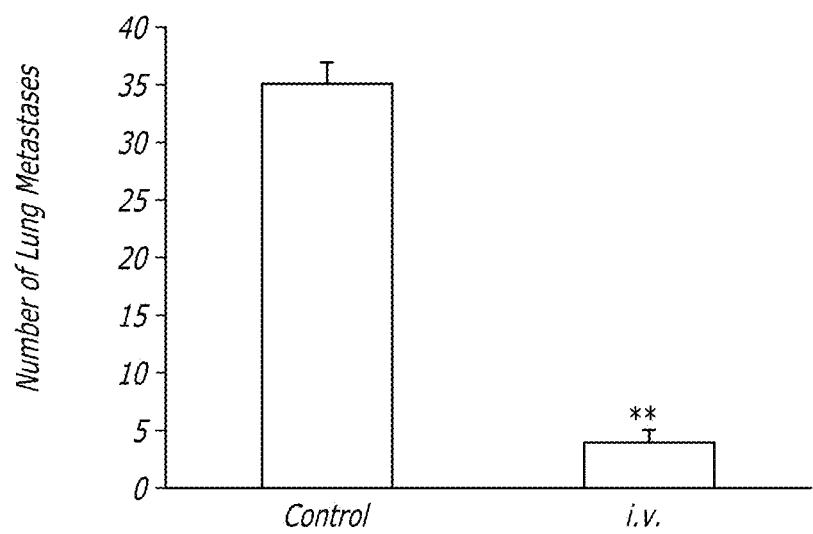
Figure 9:
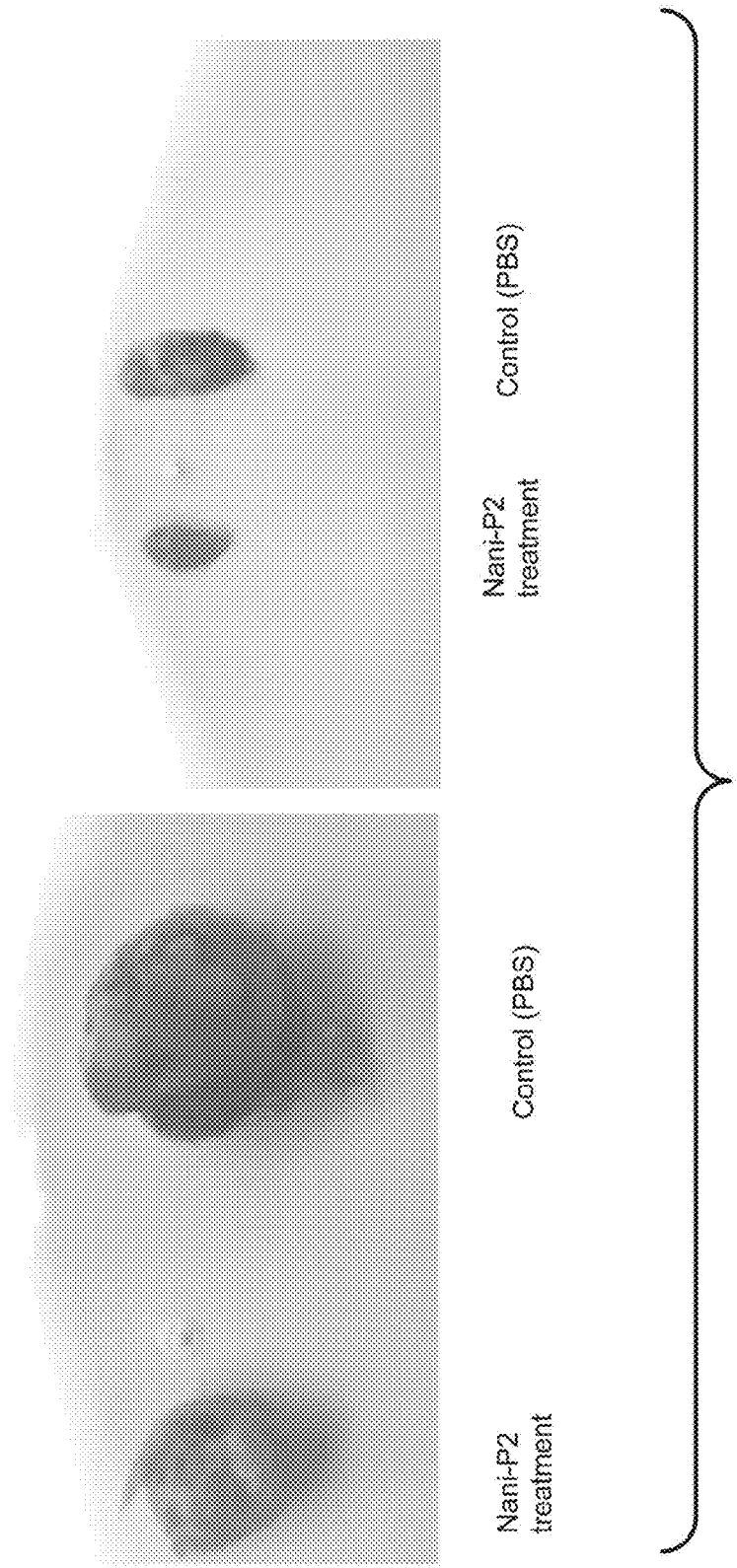
FIG. 9 depicts 4T1 tumor growth and lung metastasis in BALB/c mice. Two groups of 10 BALB/c mice were implanted subcutaneously (SC) with either $1 \times 10^4$ 4 T1 cells, mice injected IV with 40 ng Nani-P2 or PBS. On day 28 of treatment, the mice were killed and the lungs and tumor were removed, and tumor nodules were counted by eye. Photographs of the tumors and lungs, which were representative of 10 mice, are shown. Whitish tumor lesions can be observed on the surface of the lungs. Three experiments yielded similar results.

To further investigate the efficacy of Nani-P2 against established and metastatic breast cancer, 4T1 cells were injected SC in the abdominal mammary gland of mice and treatment was delayed until such time that the tumors had metastasized to the lungs and averaged 3.5 mm in size (FIG. 8A, day 13), corresponding to a 2.4 cm or stage T2 human breast tumor. Mice were followed for tumor growth (FIG. 8A) and lung metastases (FIG. 8B). At necropsy, animals that had received Nani-P2 treatment showed a dramatic reduction in the visible number of lung metastases when compared against controls (FIG. 9). The average number of grossly visible tumor nodules in the lungs of mice treated IV with Nani-P2 was seven, compared to the PBS-control group, which had an average of 35.3 ($p<0.01**$). This corresponded to a less aggressive appearance of primary tumor, as well as lung metastases that were on average much smaller in size (FIG. 8B).

Figure 10:
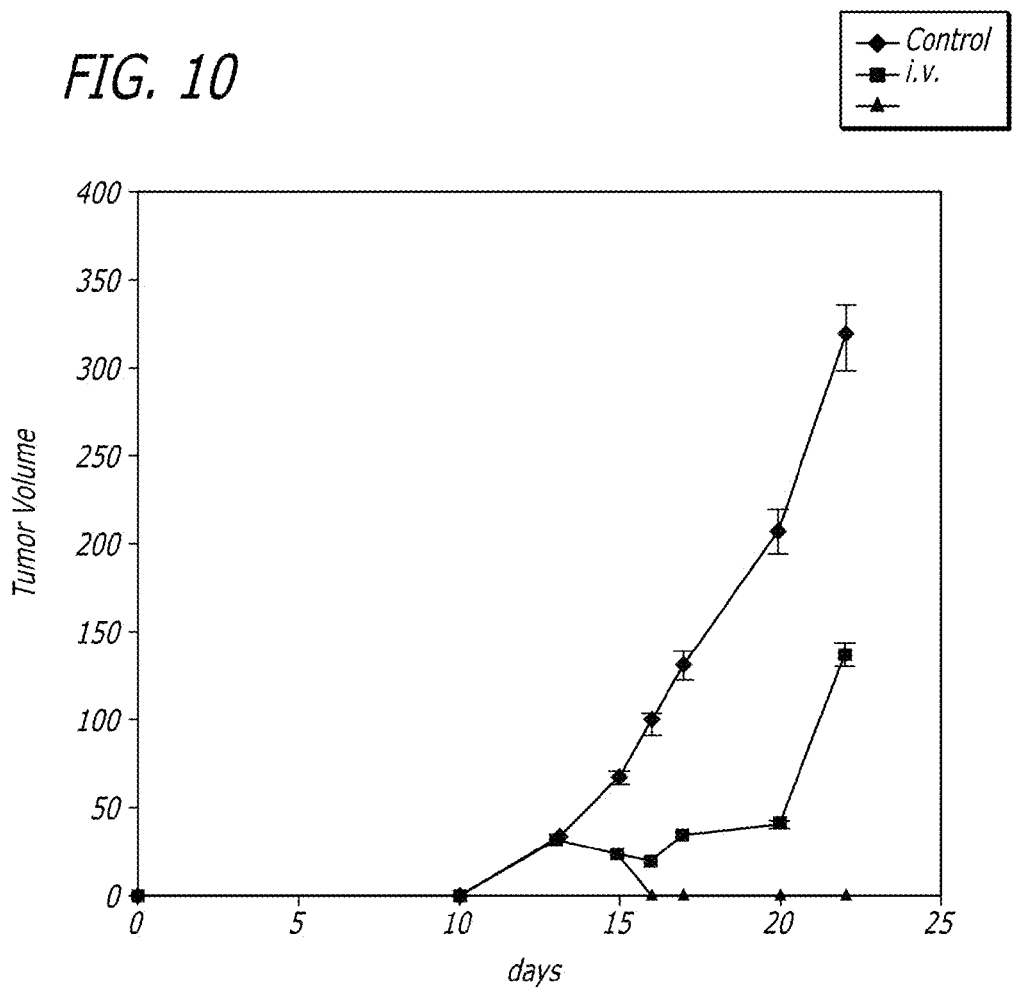
FIG. 10 depicts Nani-P2 treatment-induced regression of established 4T1 breast tumors. One of 10 mice underwent a complete remission and remained disease-free over 50 days, at which point the study was terminated. Two groups of 10 BALB/c mice were injected with $1 \times 10^4$4 T1 cells in the mammary pad on day 0. One group was dosed with Nani-P2 (40 ng) per mouse IV weekly over three weeks beginning at day 14 and the other group was treated with PBS and served as control. The difference in primary tumor growth between control and Nani-P2-treated groups was highly significant (p<0.01**).

Nani-P2 efficacy in the setting of pre-established, aggressive 4T1 breast cancer is clearly and significantly proven by comparing primary tumor burden in intravenously-treated animals (40 ng IV Nani-P2) against control (PBS-treated) animals (at day 18 $p<0.01$, FIG. 10). This statistically significant benefit in primary tumor suppression (FIG. 10) remained throughout the duration of the trial lasting 50 days ($p<0.01$) even though only three weekly doses of Tat derivative polypeptide were administered between days 14 and 28. Moreover 7/10 mice demonstrated regression of tumor at the initial treatment of tumor on day 14. This translated into a very highly statistically significant benefit to survival ($p<0.005**$, and see FIG. 5B). Remarkably, one animal underwent a complete remission and remained disease-free at 50 days, at which point the study was terminated, supporting the inference that this animal had been rendered apparently tumor-free.

Example 3

Repeated Dosing Therapy of Tat Derivatives and Cyclophosphamide

Four groups of 10 BALB/c mice were implanted with $1 \times 10^4$ 4 T1 cells SC into the mammary fat pad. Treatment was initiated when tumor diameters reached 4-5 mm, on day 10. Control mice were injected IV with PBS at 3 days intervals, while alternating treatment mice received 3 doses of drug every 3 days in rotating 10 day cycles. Tumor burden (tumor size $mm^3$) was calculated using a standard formula. CY (cyclophosphamide alone) mice were injected IP weekly with 80 mg/kg per mouse beginning on day 10. Cy/Nani-P2 (cyclophosphamide first followed by Nani-P2) mice were first injected IP with cyclophosphamide (80 mg/kg) at 3 days intervals for three doses starting at day 10 and then injected IV with Nani-P2 (40 ng) at 3 days intervals for three doses in rotation. The cycle of 3 doses of CY followed by 3 doses of Nani-P2 was repeated until day 50. Nani-P2/CY (Nani-P2 first followed by cyclophosphamide) mice were first injected IV with Nani-P2 (40 ng) at 3 day intervals for 3 doses starting on day 10 and then injected i.p. with cyclophosphamide at 3 day intervals in rotation. The cycle of 3 doses of Nani-P2 followed by 3 doses of CY was repeated until day 50.

Figure 11:
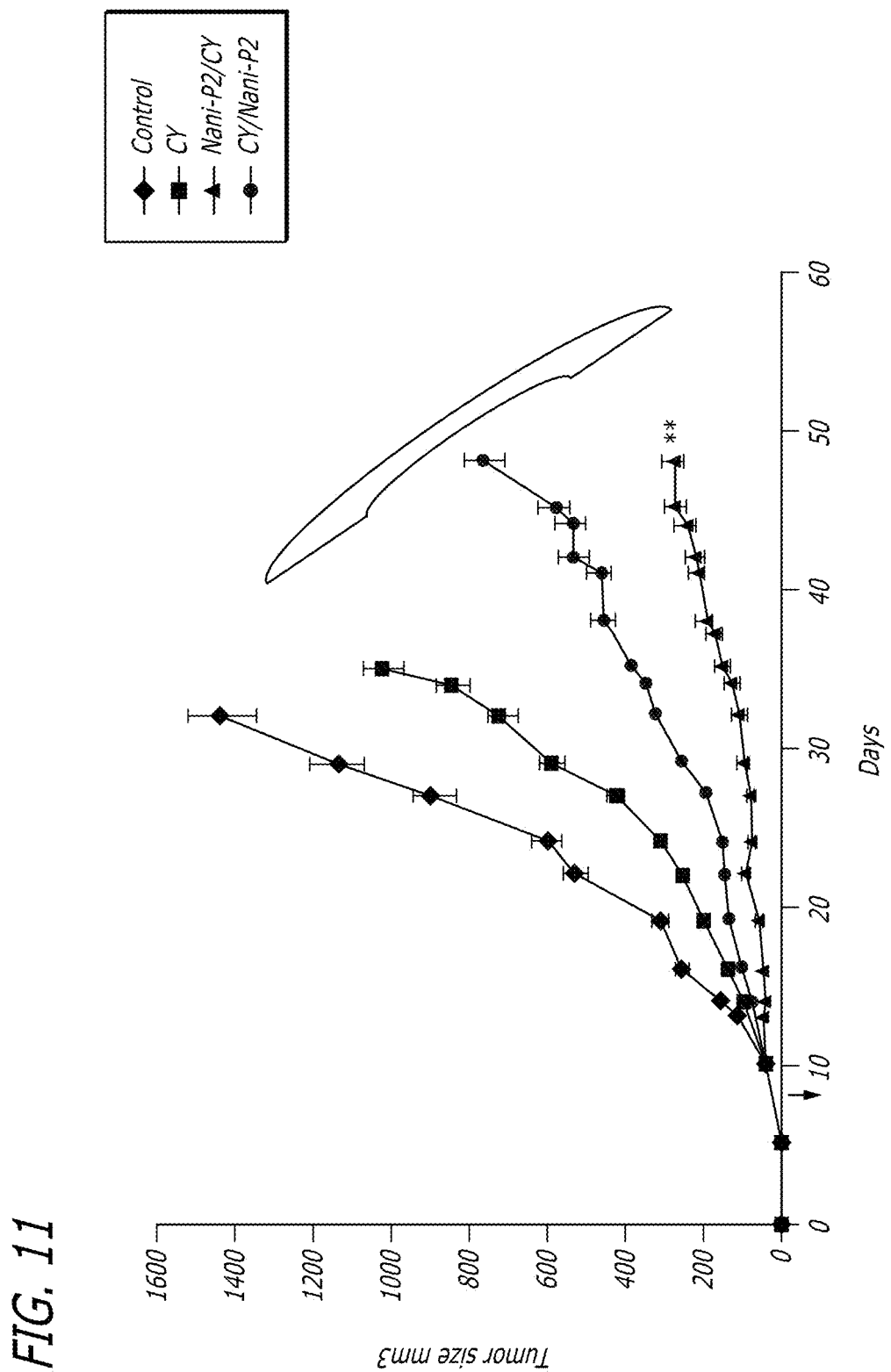
FIG. 11 depicts tumor growth after therapy with repeated doses of Nani-P2 and cyclophosphamide.

The decreased tumor burden in the Nani-P2/CY group compared to the CY group is very highly statistically significant (FIG. 11, p=0.003077).

Figure 12:
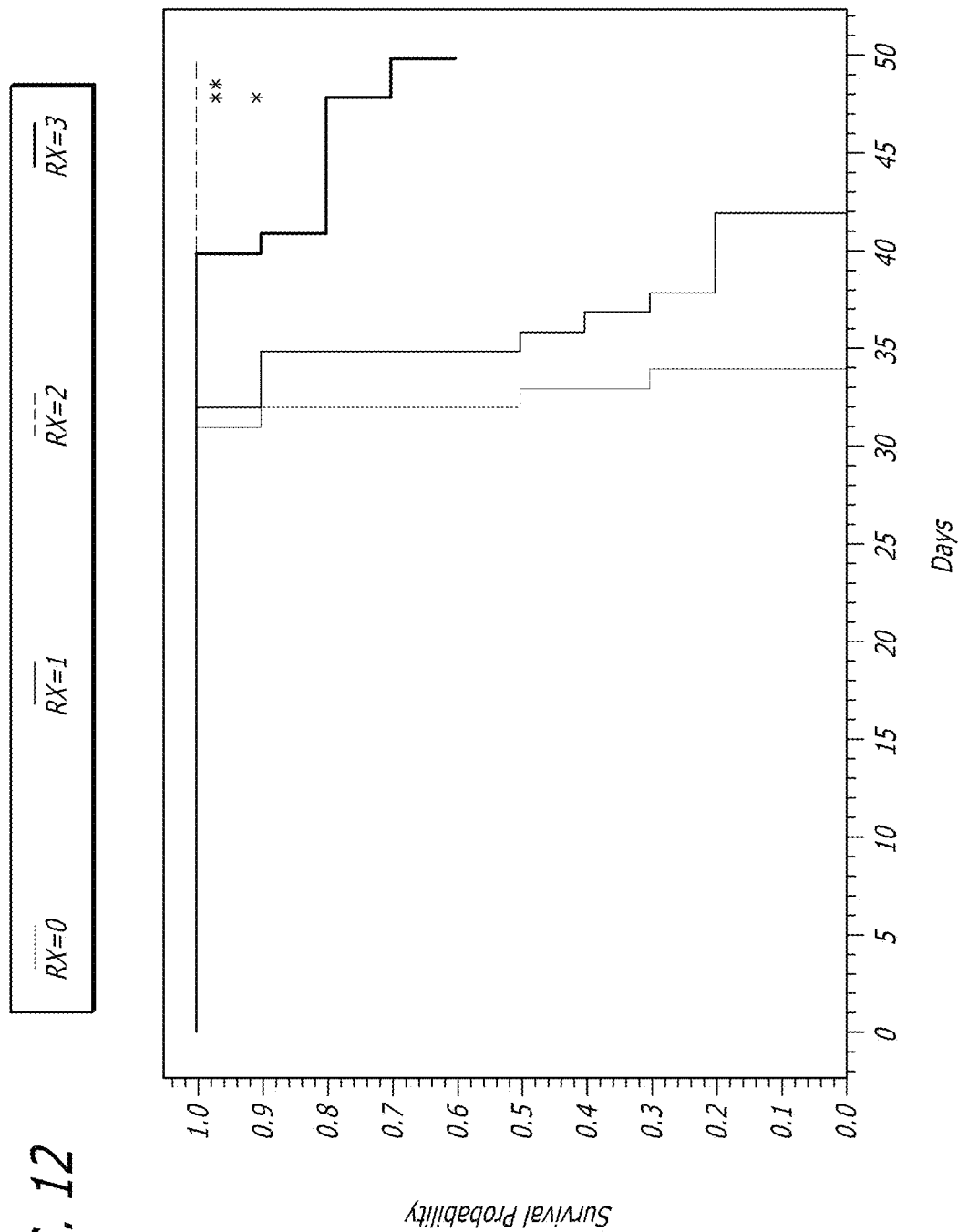
FIG. 12 depicts the survival benefit of repeated doses of Nani-P2 and cyclophosphamide vs. weekly cyclophosphamide.

The survival benefit of Nani-P2 bolus treatment alternating with cyclophosphamide vs. weekly cyclophosphamide is highly statistically significant (FIG. 12, p=0.0001). The Nani-P2 cohort has 3/10 mice in total remission and 9/10 mice in partial remission at day 50 (not shown), while 10/10 cyclophosphamide treated mice were dead by day 42.

Example 4

Presence of Splenic CD8+ CTL in Mice Receiving Nani-P2

The spleen is a major lymphoid organ and site where antigen presenting cells display captured tumor associated antigens to stimulate cytotoxic T-cell responses. Tumor specific CTLs will migrate to the site of infection and lyse the target cell.

Female BALB/c mice were inoculated in the mammary fat pad with syngeneic and highly metastatic 4T1 breast cancer cells to model Stage IV human breast cancer. Nani-P2 immunotherapy was initiated 7 days after tumor cell inoculation. Tumors were assessed by caliper measurements throughout the study and resected on Day 29/30. Immunohistochemical staining (IHC) and CD8 was performed on formalin-fixed, paraffin embedded specimens of resected spleen tissue.

Figure 13A:
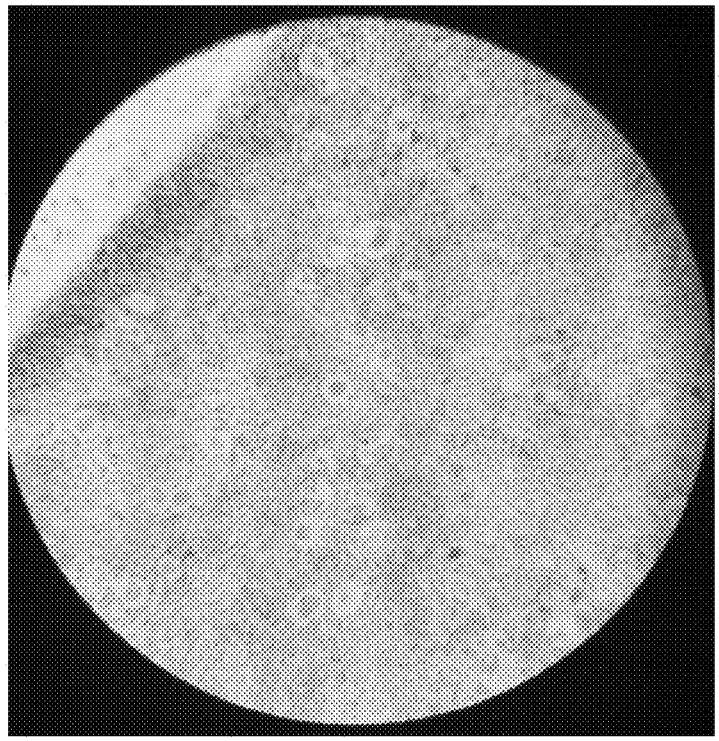
FIG. 13A-B depicts immunohistochemical (IHC) staining of CD8+ cells in spleen tissue from a mouse with 4T1 mammary carcinoma treated with PBS (Control, FIG. 13A) or Nani-P2 (FIG. 13B).
Figure 13B:
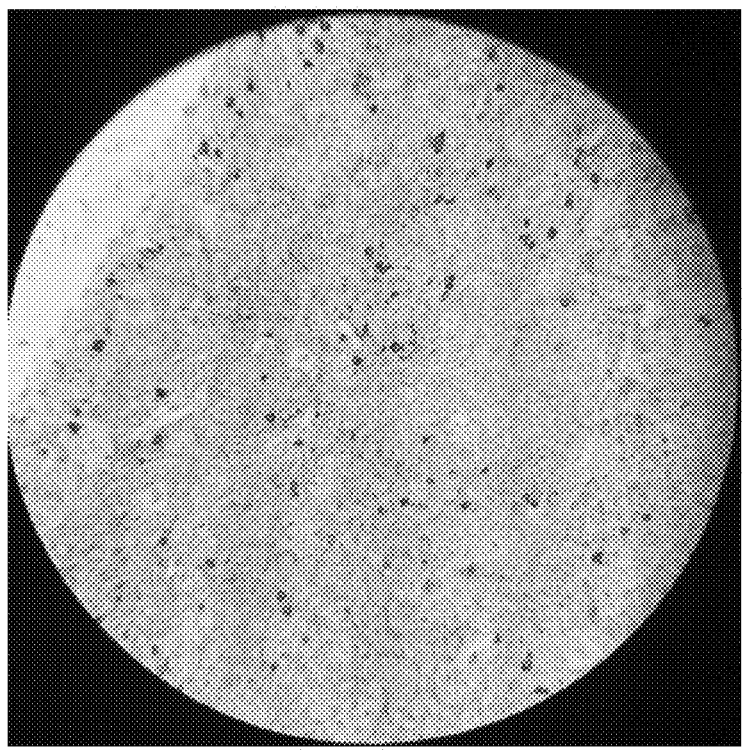

As depicted in FIG. 13, IHC staining reveals increased populations of splenic mouse CD8+ cells following treatment with Tat derivatives (FIG. 13B) versus no treatment (PBS, FIG. 13A)).

Example 5

Induction of 4T1 Breast Tumor Infiltrating CD8+ Cytotoxic T-Lymphocytes by Nani-P2 in the Presence of PD-L1

The refractory state of cancers to immunotherapeutics may be a consequence of immunosuppression that accompanies disease progression in established cancers. In the tumor microenvironment, expression of a programmed cell death receptor-ligand-1 (PD-L1) has been implicated as a marker of disease progression, poor prognosis, and impairment of host tumor immunity by suppressing the function of tumor infiltrating CD8+ cytotoxic T-lymphocytes (CTL). Therefore, the presence of PD-L1 in various tumor types represents a major barrier for developing effective immunotherapeutics.

The Tat derivative polypeptides disclosed herein elicit antitumor immune responses by triggering monocyte-derived dendritic cells to stimulate the CD8+ CTL and override PD-L1 immunosuppression. Thus, the PD-1/PD-L1 immunosuppressive signaling pathway may provide a potential mechanism by which 4T1 tumors evade host tumor immunity and therefore Tat derivative polypeptides can impact solid tumor progression by induction of tumor infiltrating CD8+ CTLs in the face of PD-L1 immunosuppression.

Female BALB/c mice were inoculated in the mammary fat pad with syngeneic and highly metastatic 4T1 breast cancer cells to model Stage IV human breast cancer. Nani-P2 immunotherapy was initiated 7 days after tumor cell inoculation. Tumors were assessed by caliper measurements throughout the study and resected on Day 29/30. Immunohistochemical staining (IHC) for PD-L1 and CD8 was performed on formalin-fixed, paraffin embedded specimens of primary 4T1 tumors.

Figure 14A:
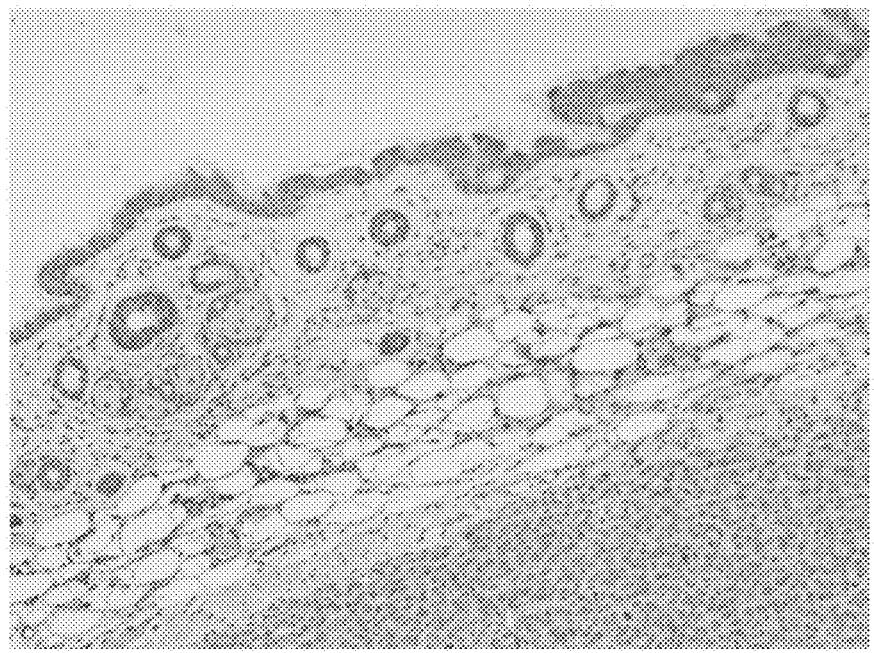
FIGS. 14A-14D depict IHC staining of primary 4T1 breast tumors for PD-L1 and CD8.
Figure 14B:
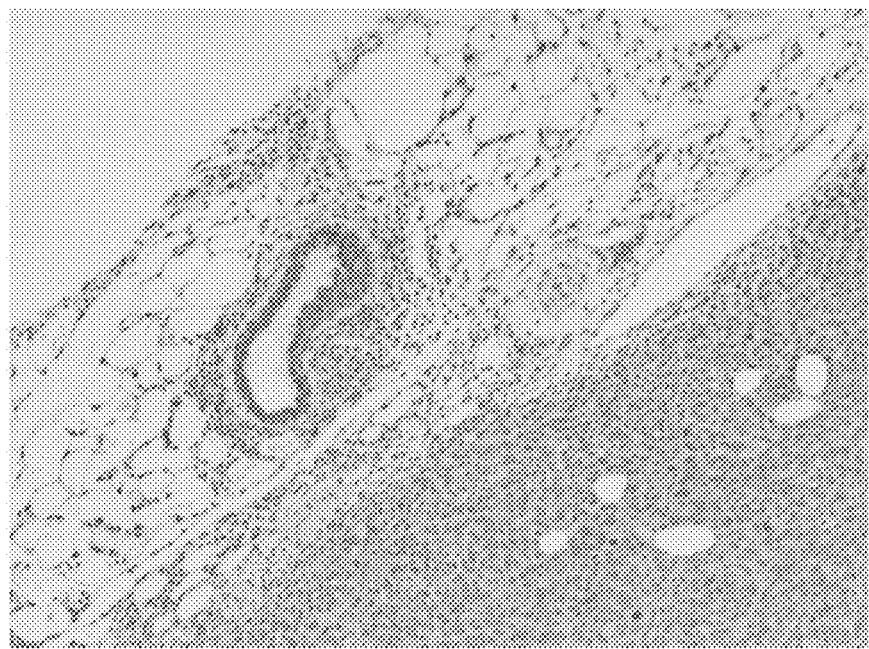
Figure 14C:
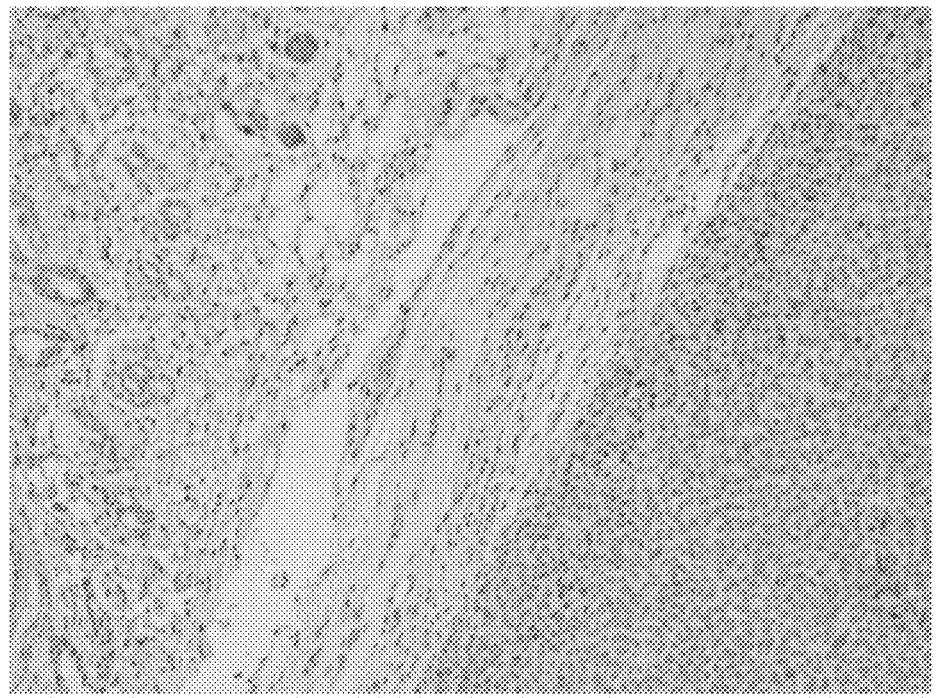
Figure 14D:
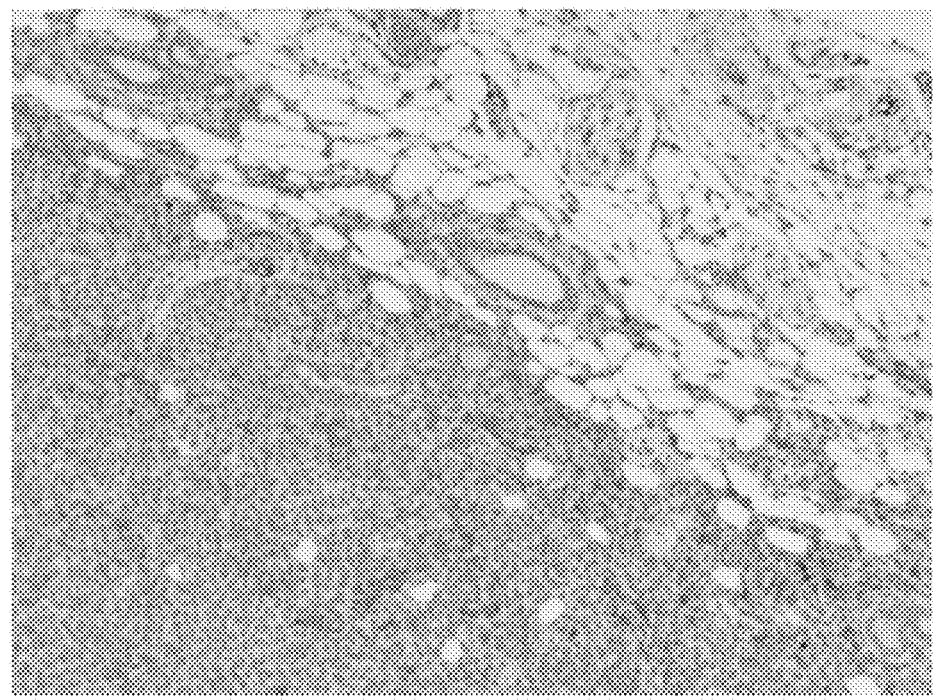

As depicted in FIG. 14, PD-L1 expression is reduced in animals receiving Nani-P2 treatment (FIG. 14B) versus controls (FIG. 14A). PD-L1 staining was observed in cells with a morphological resemblance to myeloid-derived suppressor cells, tumor-associated macrophage, as well as tumor-associated dendritic cells and fibroblast. PD-L1 reduction is based on in vivo tumor measurement data in Nani-P2 treated vs. control, combined with less PD-L1 staining intensity. Tumor edge containing majority of PD-L1 staining is largely absent in Nani-P2 treated as compared to control. Very few cells stained positive for CD8+ CTLs in the PBS control (FIG. 14C) while infiltrating CD8+ CTL advancing around tumor edge in PIN-2 treated mice (FIG. 14D).

Immunostaining of established primary 4T1 breast tumors in mice administered PIN-2 as compared to PBS control, revealed a significant increase in the population of tumor infiltrating CD8+ CTL. The presence of PD-L1 at the tumor edge may contribute to tumor malignancy and escape from immune surveillance by acting as a molecular shield to inhibit CTL-activity by engaging in the PD-1/PD-L1 signaling pathway. Tumor-infiltrating CD8+ CTLs appear to localize near the tumor edge in Nani-P2 treated mice, where as these CTLs are largely absent in tumor edges of PBS control. Since PD-L1 is a marker associated with disease progression, malignancy, and poor prognosis, the inverse correlation of tumor PD-L1 and CD8+ CTL can be explained based on the antitumor CTL response observed with PIN-2 treatment.

In conclusion, (i) reduced PD-L1 presence near the tumor edge was observed with PIN-2 treatment; (ii) CD8+ CTLs contribute to anti-tumor immune response observed PIN-2 treated mice; (iii) CD8+ CTL infiltration of PD-L1+ primary breast tumors suggests PINS override immunosuppressive mechanisms used by cancer as a barrier (immune checkpoint) to a successful antitumor immune response; (iv) positive detection of PD-L1 by IHC in established 4T1 primary breast tumors suggests a role exerted by the immunosuppressive PD-1/PD-L1 axis as an important mechanism for tumor evasion; (v) the Tat derivative polypeptides disclosed herein have the capability to override the PD-1/PD-L1 pathway in breast tumors expressing PD-L1; and (vi) administration of at derivative polypeptides disclosed herein reverses the immunosuppressive tide established during tumor progression and re-establishes immunoreactivity.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A polypeptide having an amino acid sequence comprising, in the following order:
   (i) the amino acid sequence of a transcription factor (TF) domain of a human immunodeficiency virus (HIV) or a simian immunodeficiency virus (SIV) trans-activator of transcription (Tat) protein,
   (ii) the amino acid sequence of a cysteine-rich sequence of SIV, HIV, or a defensin, and
   (iii) the amino acid sequence of a C-terminal domain of HIV or SIV Tat protein;
   wherein the polypeptide is not SEQ ID NO: 2, 3, or 4, and wherein the amino acid sequences of (i), (ii), and (iii) are not all from the same source.

2. The polypeptide of claim 1, wherein the HIV is HIV-1 or HIV-2.

3. The polypeptide of claim 1, wherein the HIV-1 Tat is from a long-term non-progressor.

4. The polypeptide of claim 1, wherein the SIV is from a host selected from Table 2.

5. The polypeptide of claim 1, wherein the defensin is an α-defensin or a β-defensin.

6. The polypeptide of claim 1, further comprising an amino acid sequence derived from an arginine-rich domain of HIV-1 or HIV-2 Tat.

7. The polypeptide of claim 1, wherein at least one of the amino acids in the TF domain is deleted or substituted with an alanine, an aspartic acid, a glutamic acid, a glycine, a lysine, a glutamine, an arginine, a serine, or a threonine.

8. The polypeptide of claim 7, wherein the at least one substituted amino acid is a proline.

9. The polypeptide of claim 1, wherein the TF domain comprises an amino acid sequence of one of SEQ ID NOs:96-123.

10. The polypeptide of claim 1, wherein the cysteine-rich domain comprises an amino acid sequence of one of SEQ ID NOs:124-132.

11. The polypeptide of claim 1, wherein the C-terminal domain comprises an amino acid sequence of one of SEQ ID NOs:133-150.

12. The polypeptide of claim 1, having greater than 85% sequence identity to one of SEQ ID NOs 5-95.

13. A pharmaceutical composition comprising a polypeptide according to claim 1.

14. A method of treating cancer comprising:
administering a therapeutically effective amount of the pharmaceutical composition of claim 13, to a subject in need thereof; and
causing cessation of growth of the cancer or regression of the cancer in the subject.

15. The method of claim 14, wherein the polypeptide is administered in a plurality of doses.

16. The method of claim 14, wherein the administering step comprises a repetitive administration cycle wherein each cycle comprises administering a plurality of doses of the Tat derivative polypeptide in a defined time period followed by a rest period and wherein the cycle is repeated a plurality of times.

17. The method of claim 14, wherein the administering step comprises a repetitive administration cycle wherein each cycle comprises administering a plurality of doses of the Tat derivative polypeptide in a defined time period followed by a administration of one or a plurality of doses of a therapeutic agent in a defined time period and wherein the cycle is repeated a plurality of times.

18. The method or use of claim 17, wherein the therapeutic agent is cyclophosphamide.

19. A method of inhibiting the suppression of an anti-tumor immune response in a subject with cancer, the method comprising:
administering a therapeutically effective amount of the polypeptide of claim 1, or the pharmaceutical composition of claim 13, to the subject; wherein the administration results in reduction or inhibition of growth of the cancer or in regression of the cancer in the subject.

20. The method of claim 19, wherein at least one pre-treatment tumor from the subject contains at least 5% PD-L1-expressing cells.

* * * * *